(12) United States Patent
Taveras et al.

(10) Patent No.: US 6,878,709 B2
(45) Date of Patent: Apr. 12, 2005

(54) 3,4-DI-SUBSTITUTED PYRIDAZINEDIONES AS CXC CHEMOKINE RECEPTOR ANTAGONISTS

(75) Inventors: Arthur G. Taveras, Denville, NJ (US); Michael Dwyer, Scotch Plains, NJ (US); Jianping Chao, Summit, NJ (US); John J. Baldwin, Gwynedd Valley, PA (US); J. Robert Merritt, Ewing, NJ (US); Ge Li, Shanghai (CN); Jianhua Chao, Pompton Lakes, NJ (US); Younong Yu, Piscataway, NJ (US)

(73) Assignees: Schering Corporation, Kenilworth, NJ (US); Pharmacopeia Drug Discovery, Inc., Princeton, NJ (US)

( * ) Notice: Subject to any disclaimer, the term of this patent is extended or adjusted under 35 U.S.C. 154(b) by 0 days.

(21) Appl. No.: 10/335,789

(22) Filed: Jan. 2, 2003

(65) Prior Publication Data

US 2004/0063709 A1 Apr. 1, 2004

Related U.S. Application Data

(60) Provisional application No. 60/346,248, filed on Jan. 4, 2002.

(51) Int. Cl.$^7$ ...................... A61K 31/50; A61K 31/501; C07D 237/22; C07D 405/12; C07D 409/12
(52) U.S. Cl. ............. 514/247; 514/252.01; 514/252.05; 544/238; 544/240
(58) Field of Search ................................. 544/238, 240; 514/247, 252.01, 252.05

(56) References Cited

U.S. PATENT DOCUMENTS

| | | |
|---|---|---|
| 4,170,588 A | 10/1979 | Hegenberg et al. |
| 4,639,523 A | 1/1987 | Nohara et al. |
| 5,206,252 A | 4/1993 | Butera et al. |
| 5,354,763 A | 10/1994 | Butera et al. |
| 5,397,790 A | 3/1995 | Butera et al. |
| 5,401,753 A | 3/1995 | Butera et al. |
| 5,403,853 A | 4/1995 | Butera et al. |
| 5,466,712 A | 11/1995 | Butera et al. |
| 5,506,252 A | 4/1996 | Butera et al. |
| 5,532,245 A | 7/1996 | Butera et al. |
| 5,840,764 A | 11/1998 | Quagliato et al. |
| 6,300,325 B1 | 10/2001 | Widdowson et al. |
| 6,376,555 B1 | 4/2002 | Butera et al. |
| 6,420,396 B1 | 7/2002 | Albers et al. |
| 2001/0018447 A1 | 8/2001 | Widdowson et al. |

FOREIGN PATENT DOCUMENTS

| | | |
|---|---|---|
| DE | 33 09 655 A1 | 9/1984 |
| EP | 0 099 121 A2 | 1/1984 |
| EP | 0 275 997 A | 7/1988 |
| EP | 0 376 079 A | 7/1990 |
| EP | 0 796 243 B1 | 1/1999 |
| GB | 1186096 | 4/1970 |
| WO | WO 94/29277 | 12/1994 |
| WO | WO 95/14005 | 5/1995 |
| WO | WO 96/14300 | 5/1996 |
| WO | WO 96/15103 | 5/1996 |
| WO | WO 98/33763 | 8/1998 |
| WO | WO 00/20378 | 4/2000 |
| WO | WO 00/21927 A | 4/2000 |
| WO | WO 00/35855 | 6/2000 |
| WO | WO 00/35864 | 6/2000 |
| WO | WO 00/73260 A1 | 12/2000 |
| WO | WO 01/29000 A2 | 4/2001 |
| WO | WO 01/64208 A1 | 9/2001 |
| WO | WO 01/64691 A1 | 9/2001 |
| WO | WO 01/68569 A2 | 9/2001 |
| WO | WO 01/92202 A1 | 12/2001 |
| WO | WO 02/057230 | 7/2002 |
| WO | WO 02/067919 | 9/2002 |
| WO | WO 02/076926 A | 10/2002 |
| WO | WO 02/083624 A1 | 10/2002 |
| WO | WO 03/057676 A1 | 7/2003 |
| WO | WO 03/080053 A1 | 10/2003 |

OTHER PUBLICATIONS

Karady, Sandor, et al., "1,2,5–Thiadiazole–1–Oxides.I.Synthesis and Reactions of Alkoxy and Alkylthio Analogs," *Heterocycles* 16(9):1561–4 (1981).

Martinez, Ana, et al., "Synthesis of nonsymmetrically 3,4–disubstituted 1,2,5–thiadiazole dioxides," *Journal of Heterocyclic Chemistry* 35(2):297–300 (1998).

Neuse, Eberhard W., et al., "Poly(squaryl amides)" *Polymer* 15:339–45 (1974).

Patent Abstracts of Japan, vol. 018, No. 361 (c–1222), Jul. 7, 1994 and JP 06 092915A, Apr. 5, 1994 abstract.

Schostarez, Heinrich J., et al., "Cyanoguanidine bioisosteres in potassium channel openers: evaluation 3,4–disubstituted–1,2,5–thiadiazole–1–oxides," *Bioorganic & Medicinal Chemistry Letters* 6(18):2187–92 (1996).

(Continued)

*Primary Examiner*—Emily Bernhardt
(74) *Attorney, Agent, or Firm*—Henry C. Jeanette

(57) ABSTRACT

Disclosed are compounds of the formula (I)

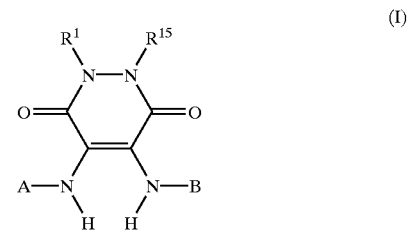

or a pharmaceutically acceptable salt or solvate thereof. The compounds are useful for the treatment of chemokine-mediated diseases such as acute and chronic inflammatory disorders and cancer.

4 Claims, No Drawings

OTHER PUBLICATIONS

Wen, Richard Y., et al. "The Chemistry of 1,2,5–Thiadiazoles. II.3,5–Disubstituted Derivatives of 1,2,5–Thiadiazole, 1,1–Dioxide," *J. Org. Chem.* 40(19):2743–8 (1975).

Zhou, Hai–Bing, et al., "Design, synthesis and structure of new chiral squaric acid monoaminoalcohls and diaminoalcohols and their use as catalysts in asymmetric reduction of ketones and diketones," *Tetrahedron* 57:9325–9333 (2001).

U.S. Pub. No. 2003/0204085 [Oct. 30, 2003] for Serial No. 10/208,426 filed Jul. 30, 2002.

U.S. Pub. No. 2004/0034229 [Feb. 19, 2004] for Serial No. 10/269,775 filed Oct. 11, 2002.

U.S. Appl. No. 10/335,789, filed Jan. 2, 2003.

U.S. Appl. No. 10/390,078, filed Mar. 17, 2003.

U.S. Appl. No. 10/630,258, filed Jul. 30, 2003.

U.S. Appl. No. 10/680,393, filed Oct. 7, 2003.

PCT International Search Report dated May 22, 2003 for corresponding PCT Application No. PCT/US03/00299.

esp#cenet Document, "1,2,5–Thiadiazole–1–oxides and 1,1–dioxides, process for their preparation and their use as medicaments" (for DE3309655 which is attached to said esp document).

Chemical Abstract 66:18527 for Maahs, Guenther, et al., "Syntheses and derivatives of squaric acid," *Angewandte Chemie* 78:(20):927–31 (1966) (which is attached to said abstract).

Chemical Abstract 87:134383 for Augustin Manfred, et al., "Disubstitution in 2,3–dichloromaleimides" *Zeitschrift Fuer Chemie* 17(6):215–216 (1977) (which is attached to said abstract).

Chemical Abstract No. 87:151727 for Ebrhardt, Heinz, et al., "Amides and thloamides of squaric acid: syntheses and reactions," *Chemische Berichte* 110(7):2506–23 (1977) (which is attached to said abstract).

Chemical Abstract 102:24633 for Stegelmeier, Hartmut, et al., "1,2,5–Thiadiazole–1–oxide and 1,1–dioxides and their use as pharmaceuticals" (for DE3309655 which is attached to said abstract).

Chemical Abstract 104:129517 for Gruenefeld, Johann, et al., "Reactions of squaric acid with carbodiimides," *Archiv der Pharmazie* 318(12):1062–70 (1985) (which is attached to said abstract).

Chemical Abstract No. 122:160745 for Tillack, Annegret, et al., "Assymmetric catalysis. IV. Hydrosilylation of acetophenone with pyrroline–2,5–dione modified [Rh(COD)C1]2 catalyst," *Journal of Organometallic Chemistry* 482:85–91 (1994) (which is attached to said abstract).

Chemical Abstract No. 125:300482 for Chen, Yizhao, et al., "Reaction of dibutyl oxosquarate with aromatic primary amines," *Sichuan Daxue Xuebao, Ziran Kexueban* 33(2):182–186 (1996) (which is attached to said abstract).

Chemical Abstract No. 130:222994 for Chen, Yi–Zhao, et al., "Synthesis of asymmetric aryl–substituted amides of squaric acid and asymmetric isosquarylium amides," *Hechen Huaxue* 6(4):383–392 (1998) (which is attached to said abstract).

Butera, John A., et al., "Design and SAR of Novel Potassium Channel Openers Targeted to Urge Urinary Incontinence. 1. N–Cyanoguanidine Bioisoteres Possessing in Vivo Bladder Selectivity," *J. Med. Chem.* 43:1187–1202 (2000).

Davis, Peter D., et al., "Inhibitors of protein kinase C 1,2,3–Bisarylmaleimides," *J. Med. Chem.* 35:177–184 (1992).

Hanaineh–Abdelnour, Leila, et al., "Some synthetic applications of 2,3–Dichloro–N–phenylmaleimide: A Novel Synthesis of 2–Phenylpyrrolo[3,4–b]quinoxaline–1,3–diones. 1," *Tetrahedron* 55:11859–11870 (1999).

Hoffman, Jacob M., et al., "Conformational Requirements of Histamine H2–Receptor Inhibitors: A Structure–Activity Study of Phenylene Analogues Related to Cimetidine and Tiotidine," *Journal of Medicinal Chemistry* 26(2):140–44 (1983).

3,4-DI-SUBSTITUTED PYRIDAZINEDIONES AS CXC CHEMOKINE RECEPTOR ANTAGONISTS

REFERENCE TO RELATED APPLICATION

This application claims the benefit of U.S. Provisional Application Ser. No. 60/346,248 filed Jan. 4, 2002.

FIELD OF THE INVENTION

This invention relates to novel substituted pyridazinedione compounds, pharmaceutical compositions containing the compounds, and the use of the compounds in treating CXC chemokine-mediated diseases.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Lett. 307, 97 (1992); Miller et al., Crit. Rev. Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines including IL-8, GROα, GROβ, GROγ, NAP-2, and ENA-78 (Strieter et al. 1995 JBC 270 p. 27348–57) have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possible CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin Cancer Res 6 p. 2104–2119) and poor prognosis (Yoneda et. al. 1998 J Nat Cancer Inst 90 p. 447–454). Chemokines are potent-chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tutor. Inhibitors of CXCR2 or dual inhibitors' of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J Clin Invest 97 p. 2792–2802), ENA-78 (Arenberg et al. 1998 J Clin Invest 102 p. 465–472), and GROα (Haghnegahdar et al. J. Leukoc Biology 2000 67 p. 53–62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and t-cell subsets into the inflammatory site and growth of tumors) would benefit by compounds that are inhibitors of IL-8 receptor binding.

SUMMARY OF THE INVENTION

The invention provides novel compounds represented by the formula (I):

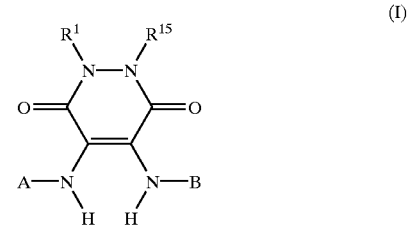

(I)

pharmaceutically acceptable salts, solvates, isomers or prodrugs thereof, wherein:

$R^1$ and $R^{15}$ are the same or different and each is independently selected from the group consisting of:
a) H,
b) aryl,
c) heteroaryl,
d) alkyl,
e) arylalkyl,
f) heteroarylalkyl,
g) cycloalkyl,
h) heterocycloalkyl,
i) cycloalkylalkyl and
j) heterocycloalkylalkyl,
wherein said aryl, heteroaryl, alkyl, arylalkyl, heteroarylalkyl, cycloalkyl, heterocycloalkyl, cycloalkylalkyl, and heterocycloalkylalkyl groups are optionally substituted with one or more substituents selected from the group consisting of:
a) halogen,
b) $CF_3$,
c) $COR^{13}$,
d) OH,
e) $NR^{13}R^{14}$, f) $NO_2$,
g) cyano,
h) $SO_2OR^{13}$,
i) —Si(alkyl),
j) —Si(aryl)
k) $CO_2R^{13}$
l) $CONR^{13}R^{14}$,
m) $SO_2NR^{13}R^{14}$,
n) $SO_2R^{13}$,
o) —$OR^{13}$,
p) —O(C=O)$R^{13}$,
q) —O(C=O)$NR^{13}R^{14}$,
r) —$NR^{13}COR^{14}$, and
s) —$NR^{13}CO_2R^{14}$;
A is selected from the group consisting of:
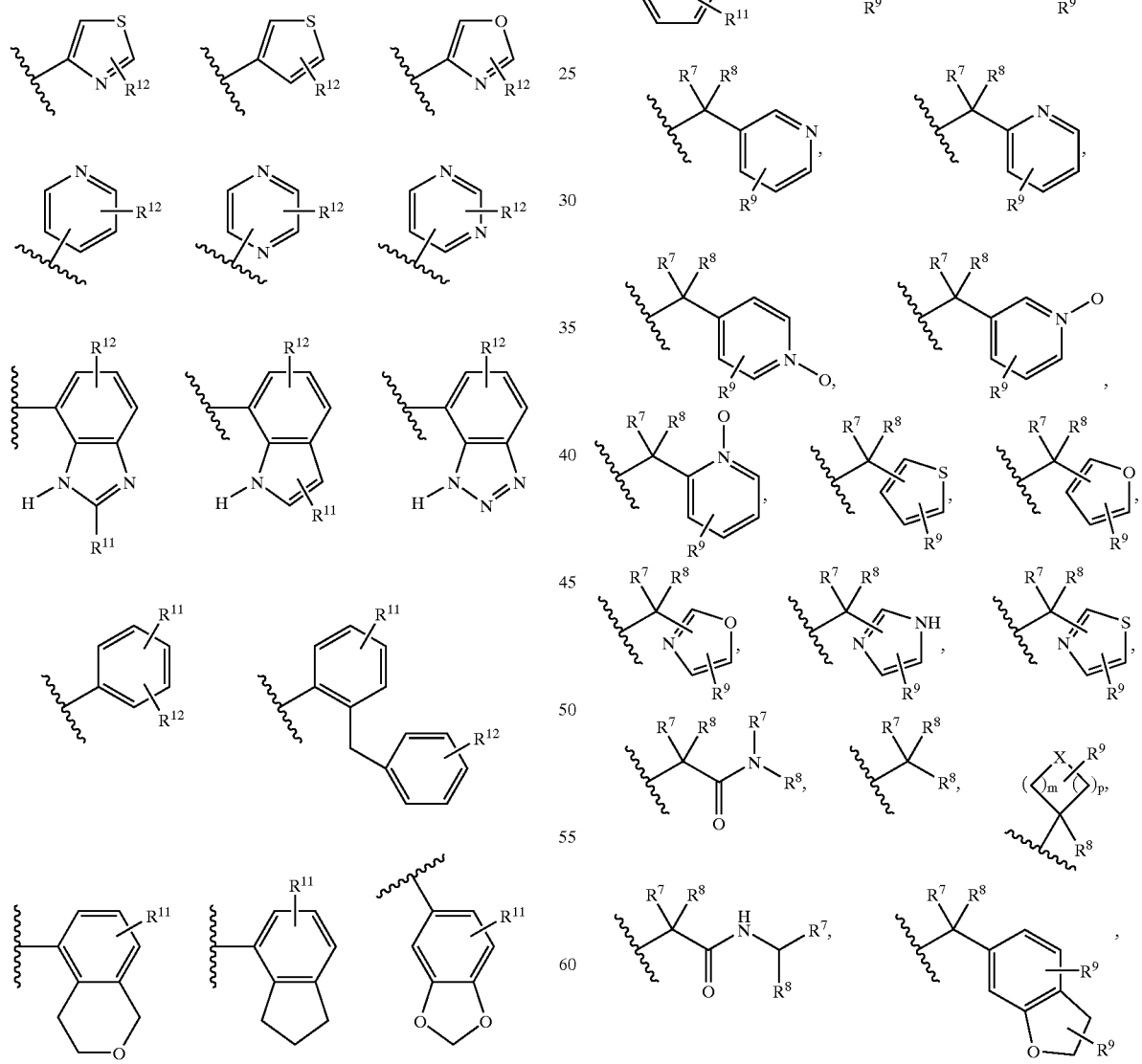

-continued
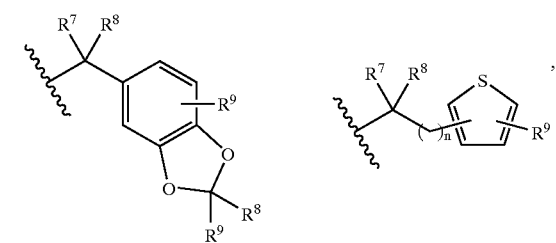
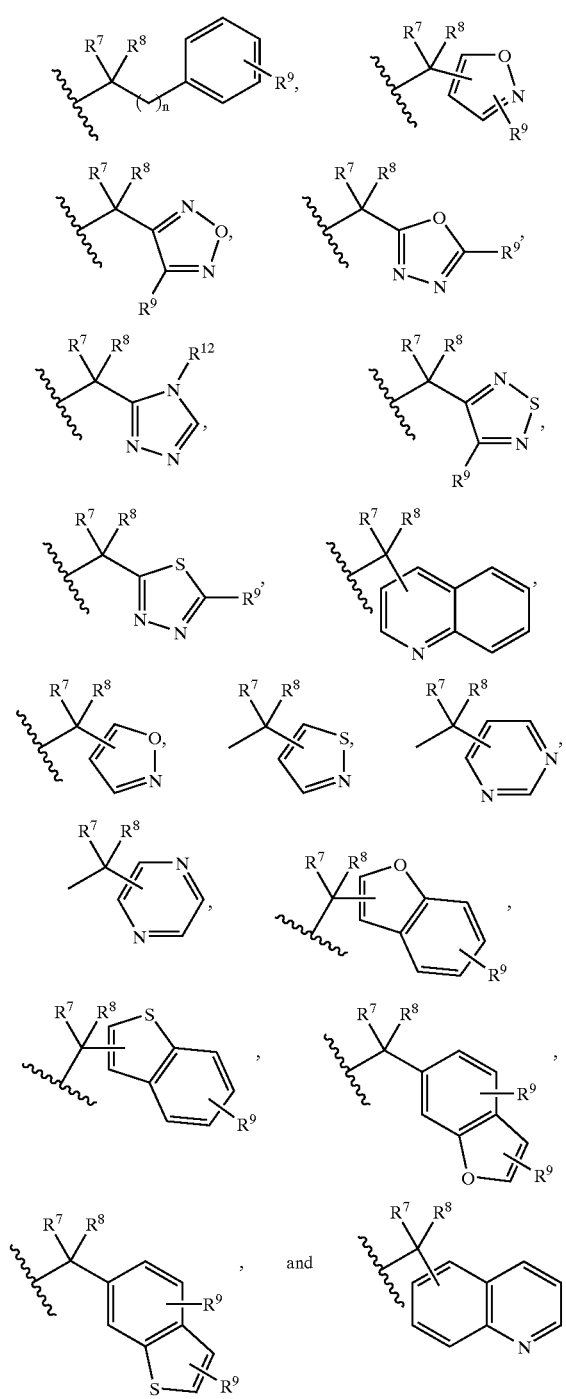
B is selected from the group consisting of:
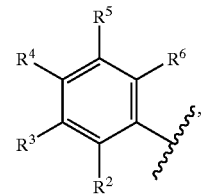
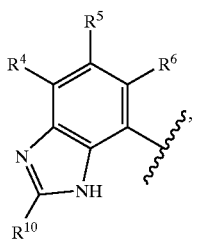
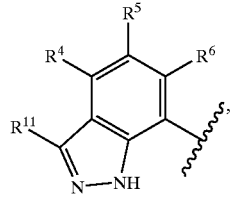
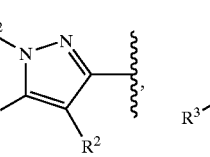
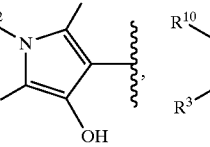
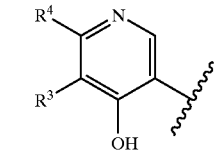
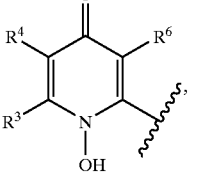
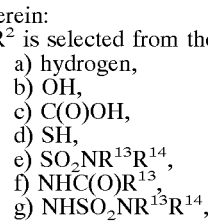
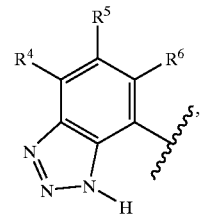
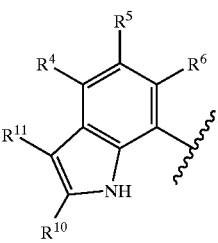
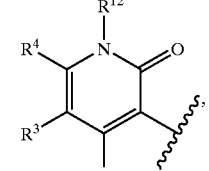
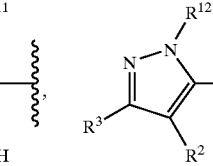
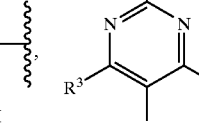
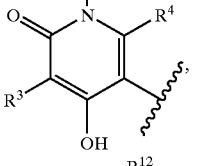
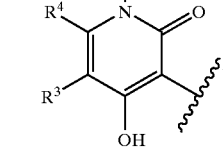
and
wherein:
$R^2$ is selected from the group consisting of:
 a) hydrogen,
 b) OH,
 c) C(O)OH,
 d) SH,
 e) $SO_2NR^{13}R^{14}$,
 f) $NHC(O)R^{13}$,
 g) $NHSO_2NR^{13}R^{14}$, h) $NR^{13}R^{14}$,
i) $NHSO_2R^{13}$,
j) $C(O)NR^{13}R^{14}$,
k) $C(O)NHOR^{13}$,
l) $C(O)NR^{13}OH$,
m) $OC(O)R^{13}$ and
n) an optionally substituted heterocyclic acidic functional group, with the proviso that if $R^2$ is $SO_2NR^{13}R^{14}$, then at least one of $R^{13}$ and $R^{14}$ must be hydrogen;

$R^3$ and $R^4$ are the same or different and each is independently selected from the group consisting of:
a) hydrogen,
b) halogen,
c) alkyl,
d) alkoxy,
e) OH,
f) $CF_3$,
g) $OCF_3$,
h) $NO_2$,
i) $C(O)R^{13}$,
j) $C(O)OR^{13}$,
k) $C(O)NR^{13}R^{14}$,
l) $SO_{(t)}NR^{13}R^{14}$,
m) $SO_{(t)}R^{13}$,
n) $C(O)NR^{13}OR^{14}$,
o)

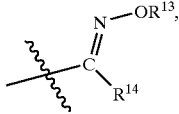

p) cyano,
q) aryl and
r) heteroaryl,
wherein said aryl or heteroaryl group is optionally substituted with one or more $R^9$ group;

$R^5$ and $R^6$ are the same or different and each is independently selected from the group consisting of
a) hydrogen,
b) halogen,
c) alkyl,
d) alkoxy,
e) $CF_3$,
f) $OCF_3$,
g) $NO_2$,
h) $C(O)R^{13}$,
i) $C(O)OR^{13}$,
j) $C(O)NR^{13}R^{14}$,
k) $SO_{(t)}NR^{13}R^{14}$,
l) $C(O)NR^{13}OR^{14}$,
m) cyano,
n) aryl and
o) heteroaryl,
wherein said aryl or heteroaryl group is optionally substituted with one or more $R^9$ group;

$R^7$ and $R^8$ are the same or different and each is independently selected from the group consisting of
a) H,
b) alkyl,
c) aryl,
d) heteroaryl,
e) arylalkyl,
f) heteroarylalkyl,
g) cycloalkyl, h) cycloalkylalkyl,
i) $CO_2R^{13}$,
j) $CONR^{13}R^{14}$,
k) fluoroalkyl,
l) alkynyl,
m) alkenyl,
n) alkynylalkyl,
o) alkenylalkyl and
p) cycloalkenyl,
wherein said alkyl, aryl, heteroaryl, arylalkyl, heteroarylalkyl, cycloalkyl, cycloalkylalkyl, fluoroalkyl, alkynyl, alkenyl, alkynylalkyl, alkenylalkyl, and cycloalkenyl groups are optionally substituted with one or more substituents selected from the group consisting of:
a) halogen,
b) $CF_3$,
c) $COR^{13}$,
d) OH,
e) $NR^{13}R^{14}$,
f) $NO_2$,
g) cyano,
h) $SO_2OR^{13}$,
i) —Si(alkyl),
j) —Si(aryl),
k) $(R^{13})_2R^{14}Si$,
l) $CO_2R^{13}$,
m) $C(O)NR^{13}R^{14}$,
n) $SO_2NR^{13}R^{14}$,
o) $SO_2R^{13}$,
p) —$OR^{13}$,
q) —$O(C=O)R^{13}$,
r) —$O(C=O)NR^{13}R^{14}$,
s) —$NR^{13}C(O)R^{14}$ and
t) —$NR^{13}CO_2R^{14}$;

$R^9$ is selected from the group consisting of:
a) $R^{13}$;
b) halogen;
c) —$CF_3$;
d) —$COR^{13}$;
e) —$OR^{13}$;
f) —$NR^{13}R^{14}$;
g) —$NO_2$;
h) cyano;
i) —$SO_2R^{13}$;
j) —$SO_2NR^{13}R^{14}$;
k) —$NR^{13}COR^{14}$;
l) —$CONR^{13}R^{14}$;
m) —$NR^{13}CO_2R^{14}$;
n) $CO_2R^{13}$, and
o)

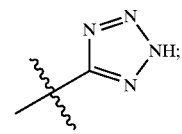

$R^{10}$ and $R^{11}$ are the same or different and each is independently selected from the group consisting of:
a) hydrogen,
b) halogen,
c) $CF_3$,
d) $OCF_3$,
e) $NR^{13}R^{14}$,
f) $NR^{13}C(O)NR^{13}R^{14}$, g) OH,
h) C(O)OR$^{13}$,
i) SH,
j) SO$_{(t)}$NR$^{13}$R$^{14}$,
k) SO$_2$R$^{13}$,
l) NHC(O)R$^{13}$,
m) NHSO$_2$NR$^{13}$R$^{14}$,
n) NHSO$_2$R$^{13}$,
o) C(O)NR$^{13}$R$^{14}$,
p) C(O)NRO$^{13}$OR$^{14}$,
q) OC(O)R$^{13}$ and
r) cyano;

R$^{12}$ is selected from the group consisting of:
 a) hydrogen,
 b) OC(O)R$^{13}$,
 c) aryl,
 d) heteroaryl,
 e) arylalkyl,
 f) cycloalkyl,
 g) alkyl,
 h) cycloalkylalkyl and
 i) heteroarylalkyl,
wherein said aryl, heteroaryl, arylalkyl, cycloalkyl, alkyl, cycloalkylalkyl and heteroarylalkyl group are optionally substituted with one or more R$^9$ group;

R$^{13}$ and R$^{14}$ are the same or different and each is independently selected from the group consisting of:
 a) H,
 b) alkyl,
 c) aryl,
 d) heteroaryl,
 e) arylalkyl,
 f) heteroarylalkyl,
 g) cycloalkyl,
 h) cycloalkylalkyl and
 i) fluoroalkyl,
 wherein said alkyl, aryl, heteroaryl, arylalkyl, heteroarylalkyl, cycloalkyl, cycloalkylalkyl, and fluoroalkyl group are optionally substituted with one or more substituents selected from the group consisting of:
  a) alkyl,
  b) aryl,
  c) arylalkyl,
  d) fluoroalkyl,
  e) cycloalkyl,
  f) cycloalkylalkyl,
  g) heteroaryl,
  h) heteroarylalkyl,
  i) amino,
  j) carbonyl and
  k) halogen; or R$^{13}$ and R$^{14}$ when taken together with the atoms to which they are attached form a 3 to 7 membered heterocyclic ring, wherein when the ring formed is a 6 or 7 membered heterocyclic ring said ring optionally contains one to two additional heteroatoms independently selected from the group consisting of O, S and N, and wherein said heterocyclic ring is optionally substituted with one or more substituents selected from the group consisting of:
  a) alkyl,
  b) aryl,
  c) arylalkyl,
  d) fluoroalkyl,
  e) cycloalkyl,
  f) cycloalkylalkyl,
  g) heteroaryl,
  h) heteroarylalkyl,
  i) amino,
  j) carbonyl and
  k) halogen;

n is 0–6;
m is 1–5;
p is 0–4 and
t is 1 or 2.

Another aspect of the invention is a pharmaceutical composition comprising the compound of formula (I) in combination or association with a pharmaceutically acceptable carrier or diluent.

Another aspect of the invention is a method of treating an α-chemokine mediated disease in a patient (e.g., a mammal such as a human being) in need of such treatment comprising administering to said patient a therapeutically effective amount of the compound of formula (I) or a pharmaceutically acceptable salt or solvate thereof.

Another aspect of the invention is a method of treating a chemokine-mediated disease in a patient in need of such treatment, wherein the chemokine binds to a CXCR2 and/or CXCR1 receptor in said patient (e.g., a mammal, such as a human being), said method comprising administering to said patient a therapeutically effective amount of a compound of formula (I) or a pharmaceutically acceptable salt or solvate thereof.

Another aspect of the invention is a method of treating a chemokine mediated disease in a patient in need of said treatment wherein the chemokine binds to a CXC receptor in said patient (e.g., a mammal, such as a human being), said method comprising administering to said patient a therapeutically effective amount of the compound of formula (I) or a pharmaceutically acceptable salt or solvate thereof.

Examples of chemokine mediated diseases include psoriasis, atopic dermatitis, asthma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis or thrombosis, alzheimer's disease, graft vs. host reaction, allograft rejections and malaria. Angiogenic ocular disease (e.g., ocular inflammation (e.g., Uveitis), retinopathy of prematurity, diabetic retinopathy, macular degeneration with the wet type preferred and corneal neovascularization) is another example of a chemokine mediated diseases.

Another aspect of the invention is a method of treating cancer in a patient in need of such treatment comprising administering to said patient a therapeutically effective amount of the compound of formula (I) or a pharmaceutically acceptable salt or solvate thereof.

Another aspect of the invention is a method of treating cancer in a patient in need of such treatment comprising administering to said patient a therapeutically effective amount of the compound of formula (I) or a pharmaceutically acceptable salt or solvate thereof, and administering a therapeutically effective amount of at least one known anti-cancer agent and/or radiation therapy.

Another aspect of the invention is a method of treating cancer in a patient in need of such treatment comprising administering to said patient a therapeutically effective amount of the compound of formula (I) or a pharmaceutically acceptable salt or solvate thereof, and administering a therapeutically effective amount of at least one known anti-cancer agent and/or radiation therapy, wherein said anti-cancer agent is selected from the group consisting of alkylating agents, antimetabolites, natural products and their derivatives, hormones, anti-hormones, anti-angiogenic agents and steroids (including synthetic analogs), and synthetics.

Another aspect of the invention is a method of inhibiting angiogenesis in a patient in need of such inhibition comprising administering to said patient an angiogenesis-inhibiting amount of the compound of formula (I) or a pharmaceutically acceptable salt or solvate thereof.

Another aspect of the invention is a method of inhibiting angiogenesis in a patient in need of such inhibition comprising administering to said patient an angiogenesis-inhibiting amount of the compound of formula (I) or a pharmaceutically acceptable salt or solvate thereof, and administering at least one known anti-angiogenesis compound.

Another aspect of the invention is a method of inhibiting angiogenesis in a patient in need of such inhibition comprising administering to said patient an angiogenesis-inhibiting amount of the compound of formula (I) or a pharmaceutically acceptable salt or solvate thereof, and administering at least one known anti-angiogenesis compound, wherein said anti-angiogenesis compound is selected from the group consisting of Marmastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, VEGF receptor kinase inhibitors, docetaxel (e.g., Taxotere), and paclitaxel (e.g., Taxol).

Another aspect of the invention is a method of treating a disease in a patient in need of such treatment, said disease selected from the group consisting of gingivitis, respiratory viruses, herpes viruses, hepatitis viruses, HIV, Kaposi's sarcoma associated virus and atherosclerosis comprising administering to said patient a therapeutically effective amount of the compound of formula (I) or a pharmaceutically acceptable salt or solvate thereof.

Another aspect of the invention is a method of treating an angiogenic ocular disease in a patient in need of such treatment comprising administering to said patient a therapeutically effective amount of the compound of formula (I) or a pharmaceutically acceptable salt or solvate thereof. Another aspect of the invention is a method of treating an angiogenic ocular disease in a patient in need of such treatment comprising administering to said patient a therapeutically effective amount of the compound of formula (I) or a pharmaceutically acceptable salt or solvate thereof, wherein said angiogenic ocular disease is selected from the group consisting of ocular inflammation (e.g., Uveitis), retinopathy of prematurity, diabetic retinopathy, macular degeneration with the wet type preferred and corneal neovascularization.

Another aspect of the invention is a method of treating cancer in a patient in need of such treatment comprising administering to said patient a therapeutically effective amount of the compound of formula (I) or a pharmaceutically acceptable salt or solvate thereof, and wherein said cancer being treated is selected from the group consisting of melanoma, gastric carcinoma or non-small cell lung carcinoma. Another aspect of the invention is a method of treating cancer in a patient in need of such treatment comprising administering to said patient a therapeutically effective amount of the compound of formula (I) or a pharmaceutically acceptable salt or solvate thereof, and administering at least one known anti-cancer agent and/or radiation therapy, and wherein said cancer being treated is selected from the group consisting of melanoma, gastric carcinoma or non-small cell lung carcinoma.

Another aspect of the invention is a method of treating cancer in a patient in need of such treatment comprising administering to said patient a therapeutically effective amount of the compound of formula (I) or a pharmaceutically acceptable salt or solvate thereof, and administering at least one known anti-cancer agent and/or radiation therapy, wherein said cancer being treated is selected from the group consisting of melanoma, gastric carcinoma or non-small cell lung carcinoma, and wherein said anti-cancer agent is selected from the group consisting of alkylating agents, antimetabolites, natural products and their derivatives, hormones, anti-hormones, anti-angiogenic agents and steroids (including synthetic analogs), and synthetics.

Another aspect of the invention is a method of treating cancer in a patient in need of such treatment comprising administering to said patient a therapeutically effective amount of the compound of formula (I) or a pharmaceutically acceptable salt or solvate thereof, and administering at least one known anti-cancer agent and/or radiation therapy, wherein said cancer being treated is selected from the group consisting of melanoma, gastric carcinoma or non-small cell lung carcinoma, wherein said anti-cancer agent is selected from the group consisting of alkylating agents, antimetabolites, natural products and their derivatives, hormones, anti-hormones, anti-angiogenic agents and steroids (including synthetic analogs), and synthetics, and wherein said anti-angiogenic agent is selected form the group consisting of Marimastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, VEGF receptor kinase inhibitors, docetaxel (e.g., Taxotere), and paclitaxel (e.g., Taxol).

Another aspect of the invention is a method of treating cancer in a patient in need of such treatment comprising administering to said patient concurrently or sequentially, a therapeutically effective amount of (a) a compound of formula (I) and (b) a microtubule affecting agent or antineoplastic agent or anti-angiogenesis agent or VEGF receptor kinase inhibitor or antibodies against the VEGF receptor or interferon, and/or c) radiation.

Another aspect of the invention is a method of treating cancer in a patient in need of such treatment comprising administering to said patient, concurrently or sequentially, an effective amount of (a) a compound of formula (I) and (b) a microtubule affecting agent (e.g., paclitaxel).

DETAILED DESCRIPTION

Unless indicated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

When any variable (e.g., aryl, $R^2$) occurs more than one time in any constituent, its definition on each occurrence is independent of its definition at every other occurrence. Also, combinations of substituents and/or variables are permissible only if such combinations result in stable compounds.

Alkyl represents a straight or branched saturated hydrocarbon chain having the designated number of carbon atoms. Where the number of carbon atoms is not specified, 1 to 20 carbons are intended.

The term halogen or halo is intended to include fluorine, chlorine, bromine or iodine.

The term fluoroalkyl represents a straight or branched saturated hydrocarbon chain having the designated number of carbon atoms, substituted with one or more fluorine atoms. Where the number of carbon atoms is not specified, 1 to 20 carbons are intended.

Aryl represents a carbocyclic group having from 6 to 14 carbon atoms and having at least one benzenoid ring, with all available substitutable aromatic carbon atoms of the carbocyclic group being intended as possible points of attachment. Examples include, but are not limited to, phenyl, naphthyl, indenyl, tetrahydronaphthyl, indanyl, anthracenyl, fluorenyl and the like. The aryl group can be substituted with one, two, or three substituents independently selected from lower alkyl, halo, cyano, nitro, haloalkyl, hydroxy, alkoxy, carboxy, carboxyalkyl, carboxamide, mercapto, sulfhydryl, amino, alkylamino, dialkylamino, sulfonyl, sulfonamido, aryl and heteroaryl.

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, which can be substituted.

The term heterocycle or heterocyclic ring is defined by all non-aromatic, heterocyclic rings of 37 atoms containing 1–3 heteroatoms selected from N, O and S, such as oxirane, oxetane, tetrahydrofuran, tetrahydropyran, pyrrolidine, piperidine, piperazine, tetrahydropyridine, tetrahydropyrimidine, tetrahydrothiophene, tetrahydrothiopyran, morpholine, hydantoin, valerolactam, pyrrolidinone, and the like.

The term heterocyclic acidic functional group is intended to include groups such as, pyrrole, imidazole, triazole, tetrazole, and the like. Such groups can be unsubstituted or substituted with one, two, or three substituents independently selected from the group consisting of lower alkyl, halo: cyano, nitro, haloalkyl, hydroxy, alkoxy, carboxy, carboxyalkyl, carboxamide, sulfhydryl, amino, alkylamino, dialkylamino, sulfonyl, sulfonamido, aryl and heteroaryl.

Heteroaryl refers to 5- or 10-membered single or benzo-fused aromatic rings consisting of 1 to 3 heteroatoms independently selected from the group consisting of —O—, —S—, and —N═, provided that the rings do not possess adjacent oxygen and/or sulfur atoms. The heteroaryl group can be substituted with one, two, or three substituents independently selected from lower alkyl, halo, cyano, nitro, haloalkyl, hydroxy, alkoxy, carboxy, carboxyalkyl, carboxamide, sulfhydryl, amino, alkylamino and dialkylamino.

N-oxides can form on a tertiary nitrogen present in an R substituent, or on ═N— in a heteroaryl ring substituent and are included in the compounds of formula (I).

Also included in the invention are tautomers, enantiomers and other optical isomers of compounds of Formula I, as well as pharmaceutically acceptable salts and solvates thereof.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design. American Pharmaceutical Association and Pergamon Press, 1987, both of which are incorporated herein by reference.

As used herein, the term "composition" is intended to encompass a product comprising the specified ingredients in the specified amounts, as well as any product which results, directly or indirectly, from combination of the specified ingredients in the specified amounts.

Examples of "one or more", as used herein, include (a) 1, 2 or 3, (b) 1 or 2, and (c) 1.

Examples of "at least one", as used herein, include (a) 1, 2 or 3, (b) 1 or 2, and (c) 1.

The following terms may be referred to herein by the abbreviations indicated: tetrahydrofuran (THF), ethanol (EtOH), methanol (MeOH), acetic acid (HOAc or AcOH), ethyl acetate (EtOAc), N,N-dimethylformamide (DMF), trifluoroacetic acid (TFA), trifluoroacetic anhydride (TFAA), 1-hydroxybenzotriazole (HOBT), m-chloroperbenzoic acid (MCPBA), triethylamine ($Et_3N$), diethyl ether ($Et_2O$), ethyl chloroformate ($ClCO_2Et$), 1-(3-dimethylaminopropyl)-3-ethyl carbodiimide hydrochloride (DEC), N,N'-dicyclohexylcarbodiimide (DCC), sodium hydroxide (NaOH), magnesium sulfate ($MgSO_4$), dichloromethane ($CH_2Cl_2$), ammonium hydroxide ($NH_4OH$), sodium sulfate ($Na_2SO_4$), thin layer chromatography (TLC).

In a preferred group of compounds of formula (I), A is selected from the group consisting of

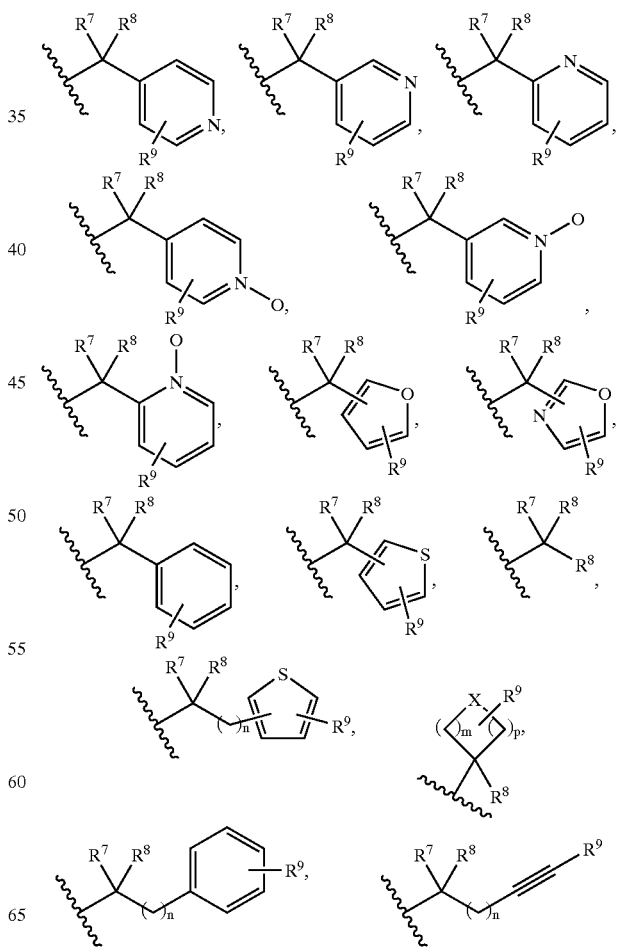

-continued

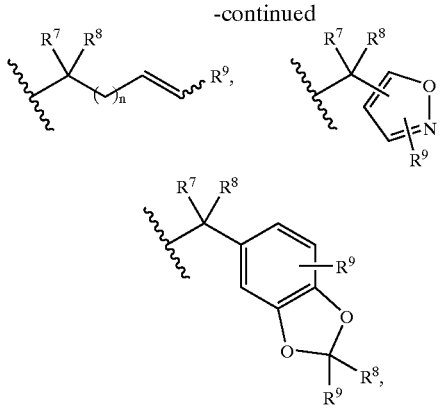

wherein,

R[7] and R[8] are the same or different and each is independently selected from the group consisting of
a) H,
b) alkyl,
c) aryl,
d) heteroaryl,
e) arylalkyl,
f) heteroarylalkyl,
g) cycloalkyl,
h) cycloalkylalkyl,
i) $CO_2R^{13}$,
j) $CONR^{13}R^{14}$,
k) fluoroalkyl,
l) alkynyl,
m) alkenyl,
n) alkynylalkyl,
o) alkenylalkyl and
p) cycloalkenyl, wherein said alkyl, aryl, heteroaryl, arylalkyl, heteroarylalkyl, cycloalkyl, cycloalkylalkyl, fluoroalkyl, alkynyl, alkenyl, alkynylalkyl, alkenylalkyl, and cycloalkenyl groups are optionally substituted with one or more substituents selected from the group consisting of:
a) cyano;
b) $CO_2R^{13}$;
c) $C(O)NR^{13}R^{14}$;
d) $SO_2NR^{13}R^{14}$,
e) $NO_2$;
f) $CF_3$;
g) —$OR^{13}$;
h) —$NR^{13}R^{14}$;
i) —$O(C=O)R^{13}$;
j) —$O(C=O)NR^{13}R^{14}$, and
k) halogen;

R[9] is selected from the group consisting of:
a) $R^{13}$,
b) halogen,
c) —$CF_3$,
e) —$OR^3$,
f) —$NR^{13}R^{14}$,
g) —$NO_2$,
h) cyano,
i) —$SO_2R^{13}$,
j) $SO_2NR^{13}R^{14}$,
k) —$NR^{13}COR^{14}$,
l) —$CONR^{13}R^{14}$,
m) —$NR^{13}CO_2R^{14}$,
n) $CO_2R^{13}$ and

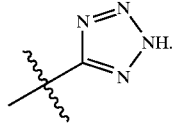

B is selected from the group consisting of

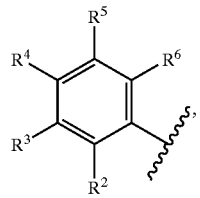 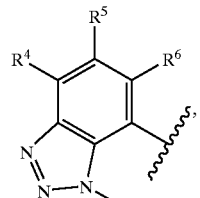

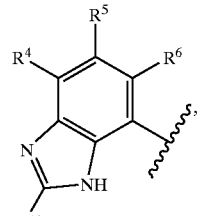 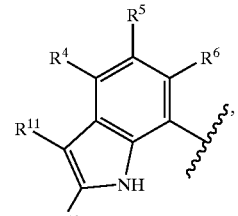

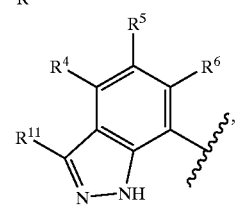 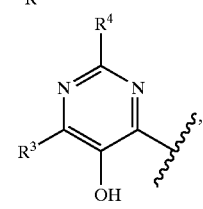

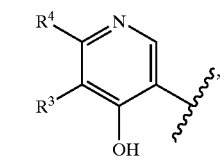 and 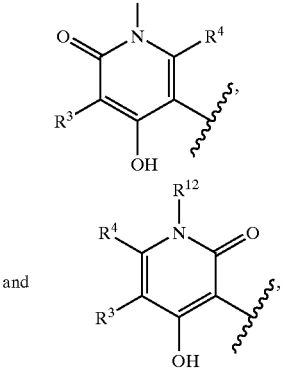

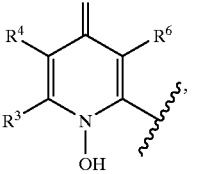

wherein,
R[2] is selected from the group consisting of
a) hydrogen,
b) OH,
c) C(O)OH,
d) SH,
e) $SO_2NR^{13}R^{14}$,
f) $NHC(O)R^{13}$,
j) $C(O)NR^{13}R^{14}$,
k) $C(O)NHOR^{13}$,
l) $C(O)NR^{13}OH$,
m) $OC(O)R^{13}$ and
n) an optionally substituted heterocyclic acidic functional group, with the proviso that if R[2] is $SO_2NR^{13}R^{14}$, at least one of R[13] and R[14] must be hydrogen;

$R^3$ and $R^4$ are the same or different and each is independently selected from the group consisting of:
a) hydrogen,
b) halogen,
c) alkyl,
d) alkoxy,
e) OH,
f) $CF_3$,
g) $OCF_3$,
h) $NO_2$,
i) $C(O)R^{13}$,
j) $C(O)OR^{13}$,
k) $C(O)NR^{13}R^{14}$,
l) $SO_{(t)}NR^{13}R^{14}$,
m) $SO_{(t)}R^{13}$,
n) $C(O)NR^{13}OR^{14}$,
o)

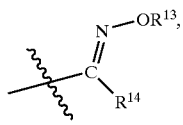

p) cyano,
q) aryl and
r) heteroaryl,
wherein said aryl or heteroaryl group is optionally substituted with one or more $R^9$ group;
$R^5$ and $R^6$ are the same or different and each is independently selected from the group consisting of:
a) hydrogen,
b) halogen,
c) alkyl,
d) alkoxy,
e) $CF_3$,
f) $OCF_3$,
g) $NO_2$,
h) $C(O)R^{13}$,
i) $C(O)OR^{13}$,
j) $C(O)NR^{13}R^{14}$,
k) $SO_{(t)}NR^{13}R^{14}$,
l) $C(O)NR^{13}OR^{14}$,
m) cyano,
n) aryl and
o) heteroaryl,
wherein said aryl or heteroaryl group is optionally substituted with one or more $R^9$ group;
$R^{10}$ and $R^{11}$ are the same or different and each is independently selected from the group consisting of:
a) hydrogen,
b) halogen,
c) $CF_3$,
d) $OCF_3$,
e) $NR^{13}R^{14}$,
f) $NR^{13}C(O)NR^{13}R^{14}$,
g) OH,
h) $C(O)OR^{13}$,
i) SH,
j) $SO_{(t)}NR^{13}R^{14}$,
k) $SO_2R^{13}$,
l) $NHC(O)R^{13}$,
m) $NHSO_2NR^{13}R^{14}$,
n) $NHSO_2R^{13}$,
o) $C(O)NR^{13}R^{14}$,
p) $C(O)NRO^{13}OR^{14}$,
q) $OC(O)R^{13}$ and
r) cyano;

$R^{12}$ is selected from the group consisting of:
a) hydrogen,
b) $OC(O)R^{13}$,
c) aryl,
d) heteroaryl,
e) arylalkyl,
f) cycloalkyl,
g) alkyl,
h) cycloalkylalkyl and
i) heteroarylalkyl
wherein said aryl, heteroaryl, arylalkyl, cycloalkyl, alkyl, cycloalkylalkyl or heteroarylalkyl group is optionally substituted with one or more $R^9$ group;
$R^{13}$ and $R^{14}$ are the same or different and each is independently selected from the group consisting of:
a) H;
b) alkyl,
c) aryl,
d) heteroaryl,
e) arylalkyl,
f) heteroarylalkyl,
g) cycloalkyl,
h) cycloalkylalkyl and
i) fluoroalkyl,
wherein said alkyl, aryl, heteroaryl, arylalkyl, heteroarylalkyl, cycloalkyl, cycloalkylalkyl, and fluoroalkyl groups are optionally substituted with one or more substituents selected from the group consisting of:
a) alkyl,
b) aryl,
c) arylalkyl,
d) fluoroalkyl,
e) cycloalkyl,
f) cycloalkylalkyl,
g) heteroaryl,
h) heteroarylalkyl,
i) amino,
j) carbonyl and
k) halogen or
$R^{13}$ and $R^{14}$ when taken together with the atoms to which they are attached can form a 3 to 7 membered heterocyclic ring wherein when the ring formed is a 6 or 7 membered heterocyclic ring, said ring optionally contains one to two additional heteroatoms independently selected from the group consisting of O, S and N and wherein said heterocyclic ring can be substituted with one or more substituents selected from the group consisting of:
a) alkyl,
b) aryl,
c) arylalkyl,
d) fluoroalkyl,
e) cycloalkyl,
f) cycloalkylalkyl,
g) heteroaryl,
h) heteroarylalkyl,
i) amino,
j) carbonyl and
k) halogen;
n is 0–6;
m is 1–5;
p is 0–4 and
t is 1 or 2.
Preferably, $R^1$ and $R^{15}$ are the same or different and are individually selected from the group consisting of H, methyl, aryl and cyclohexyl.

More preferably, A is selected from the group consisting of:

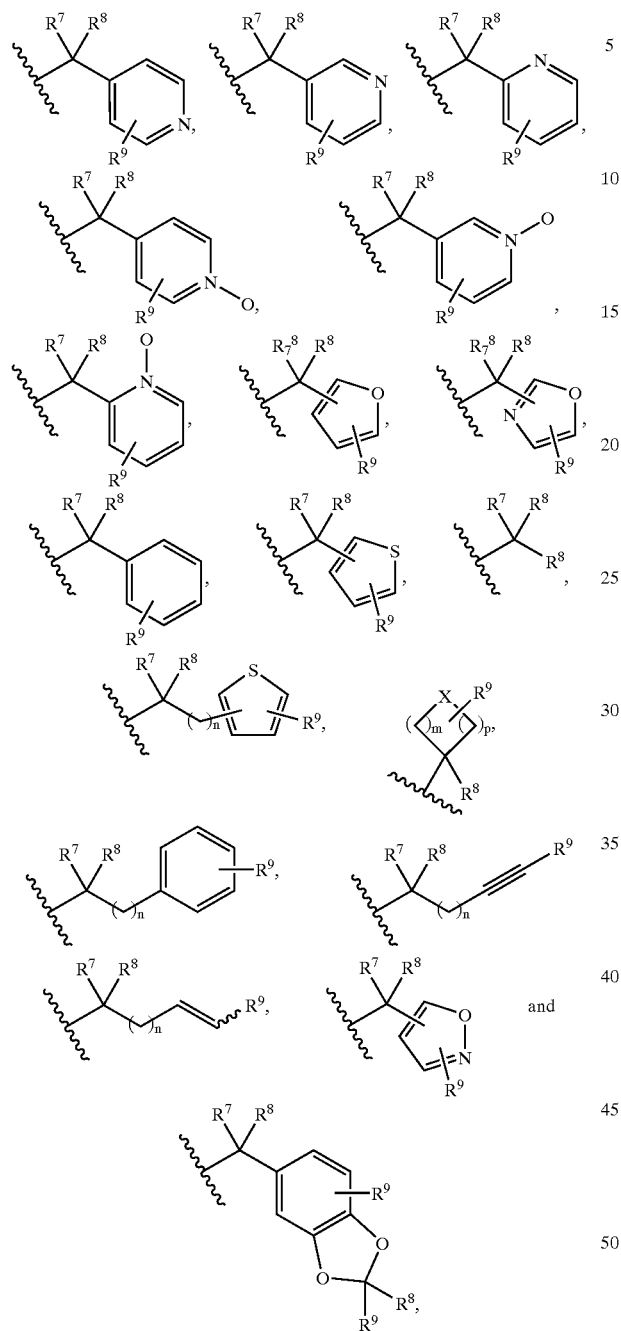

wherein

R[7] and R[8] are the same or different and each is independently selected from the group consisting of H, alkyl, fluoroalkyl such as, $CF_3$ and $CF_2CH_3$, cycloalkyl and cycloalkyl, such as, for example, methyl, ethyl, t-butyl, isopropyl, cyclopropyl, cyclopropylmethyl and cyclohexyl and R[9] is selected from the group consisting of H, halogen (e.g. bromine, fluorine or chlorine), $CH_3$, $CF_3$, fluoroalkyl, cyano, —$OCH_3$, and $NO_2$.

More preferably, B is selected from the group consisting of:

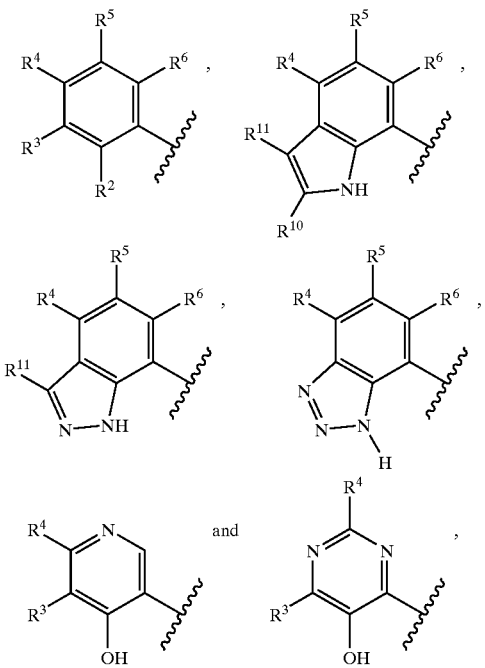

wherein $R^2$ is selected from the group consisting of H, OH, $NHC(O)R^{13}$ and $NHSO_2R^{13}$;

$R^3$ is selected from the group consisting of $SO_2NR^{13}R^{14}$, $NO_2$, cyano, $C(O)NR^{13}R^{14}$, $SO_2R^{13}$; and $C(O)OR^{13}$;

$R^4$ is selected from the group consisting of H, $NO_2$, halo, cyano, $CH_3$ and $CF_3$;

$R^5$ is selected from the group consisting of H, $CF_3$, $NO_2$, halo and cyano;

$R^6$ is selected from the group consisting of H, alkyl and $CF_3$;

$R^{10}$ and $R^{11}$ are the same or different and each is independently selected from the group consisting of:
a) hydrogen,
b) halo,
c) $CF_3$,
d) $OCF_3$,
e) $NR^{13}R^{14}$,
f) $NR^{13}C(O)NR^{13}R^{14}$,
g) OH,
h) $C(O)OR^{13}$,
i) SH,
j) $SO_{(t)}NR^{13}R^{14}$,
k) $SO_2R^{13}$,
l) $NHC(O)R^{13}$,
m) $NHSO_2NR^{13}R^{14}$,
n) $NHSO_2R^{13}$,
o) $C(O)NR^{13}R^{14}$,
p) $C(O)NRO^{13}OR^{14}$,
q) $OC(O)R^{13}$,
r) $COR^{13}$,
s) $OR^{13}$ and
t) cyano;

$R^{12}$ is selected from the group consisting of hydrogen and $C(O)OR^{13}$;

$R^{13}$ and $R^{14}$ are the same or different and each is independently selected from the group consisting of methyl, ethyl and isopropyl; or $R^{13}$ and $R^{14}$ when taken together with the atoms to which they are attached can form a 3 to 7 membered heterocyclic ring wherein when the ring formed is a 6 or 7 membered heterocyclic ring, said ring optionally contains one to two additional heteroatoms independently selected from the group consisting of O, S and N and wherein said heterocyclic ring can be substituted with one or more substituents selected from the group consisting of:
a) alkyl,
b) aryl,
c) arylalkyl,
d) fluoroalkyl,
e) cycloalkyl,
f) cycloalkylalkyl,
g) heteroaryl,
h) heteroarylalkyl,
i) amino,
j) carbonyl and
k) halogen.

Even more preferably, A is selected from:

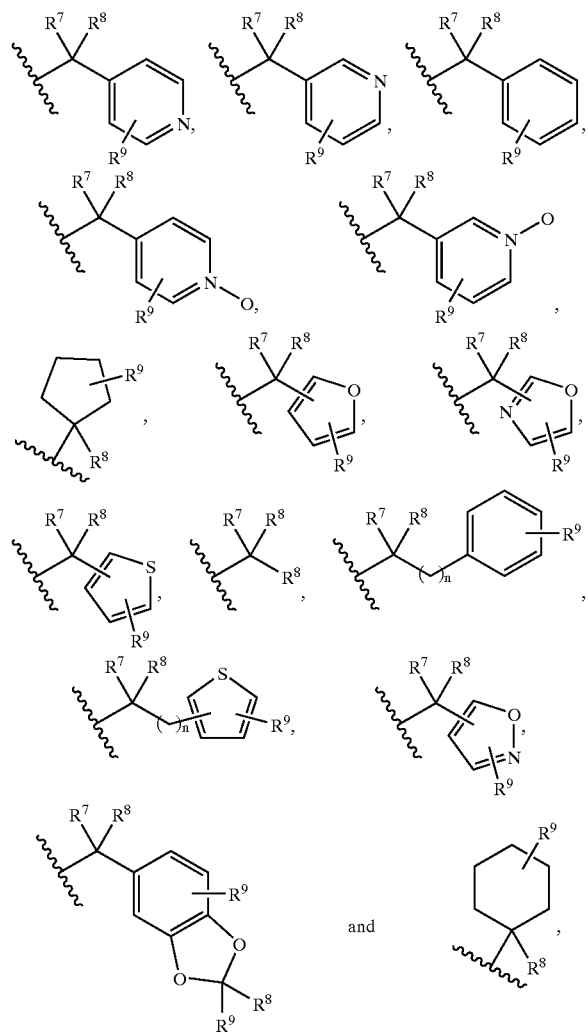

wherein
$R^7$ is selected from the group consisting of H, $CF_3$, fluoroalkyl, alkyl and cycloalkyl;
$R^8$ is selected from the group consisting of H, alkyl and fluoroalkyl;
$R^9$ is selected from the group consisting of H, F, Cl, Br, $CF_3$, alkyl and fluoroalkyl.

Still even more preferably, A is selected from the group consisting of:

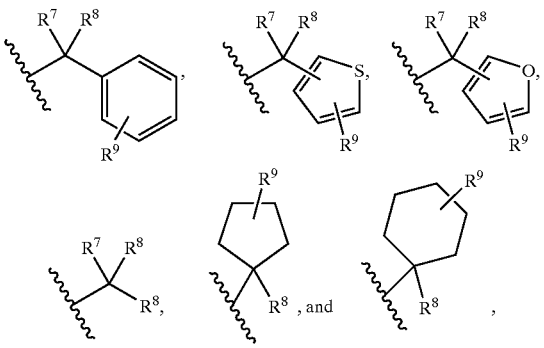

wherein,
$R^7$ is selected from the group consisting of H, $CF_3$, $CF_2CH_3$, methyl, ethyl, isopropyl, cyclopropyl and t-butyl;
$R^8$ is H;
$R^9$ is selected from the group consisting of H, F, Cl, Br, $CF_3$, alkyl and fluroalkyl; and
B is:

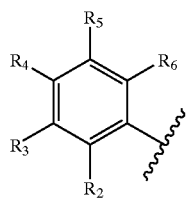

wherein:
$R^2$ is selected from the group consisting of H, OH, $NHC(O)R^{13}$ and $NHSO_2R^{13}$;
$R^3$ is selected from the group consisting Of $SO_2NR^{13}R^{14}$, $NO_2$, cyano, $C(O)NR^{13}R^{14}$, $SO_2R^{13}$; and $C(O)OR^{13}$;
$R^4$ is selected from the group consisting of H, $NO_2$, halo, cyano, $CH_3$ and $CF_3$;
$R^5$ is selected from the group consisting of H, $CF_3$, $NO_2$, halo and cyano;
$R^6$ is selected from the group consisting of H, alkyl and $CF_3$; and
$R^{13}$ and $R^{14}$ are the same or different and each is independently selected from the group consisting of methyl, ethyl and isopropyl; or
$R^{13}$ and $R^{14}$ when taken together with the atoms to which they are attached can form a 3 to 7 membered heterocyclic ring wherein when the ring formed is a 6 or 7 membered heterocyclic ring, said ring optionally contains one to two additional heteroatoms independently selected from the group consisting of O, S and N and wherein said heterocyclic ring can be substituted with one or more substituents selected from the group consisting of:
a) alkyl,
b) aryl,
c) arylalkyl,
d) fluoroalkyl,
e) cycloalkyl, f) cycloalkylalkyl,
g) heteroaryl,
h) heteroarylalkyl,
i) amino,
j) carbonyl and
k) halogen.

Yet even still more preferred,

A is selected from the group consisting of:

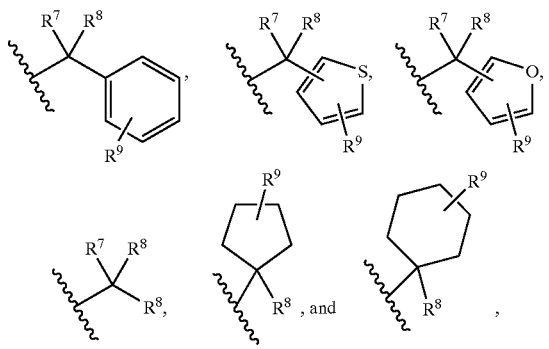

and B is:

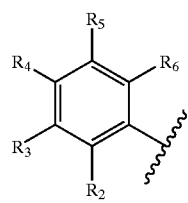

wherein:

$R^2$ is selected from the group consisting of H, OH, $NHC(O)R^{13}$ and $NHSO_2R^{13}$;

$R^3$ is selected from the group consisting of $SO_2NR^{13}R^{14}$, $C(O)NR^{13}R^{14}$, $SO_2R^{13}$, $NO_2$ or cyano;

$R^4$ is selected from the group consisting of H, $NO_2$, $CF_3$, $CH_3$, halo and cyano, $R^5$ is selected from the group consisting of H, halo, $NO_2$, cyano and $CF_3$;

$R^6$ is selected from the group consisting of H, $CF_3$ and alkyl;

$R^7$ is selected from the group consisting of H, $CF_3$, $CF_2CH_3$, methyl, ethyl, isopropyl, cyclopropyl and t-butyl;

$R^8$ is H;

$R^9$ is selected from the group consisting of H, F, Cl, Br, $CF_3$, alkyl, and fluroalkyl; and $R^{13}$ and $R^{14}$ are each independently selected from the group consisting of methyl and ethyl.

Most preferably,

A is selected from the group consisting of:

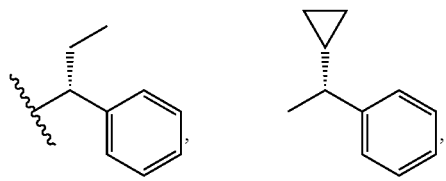

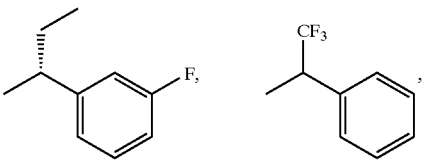

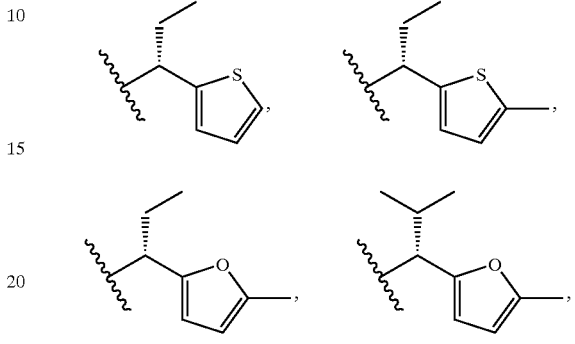

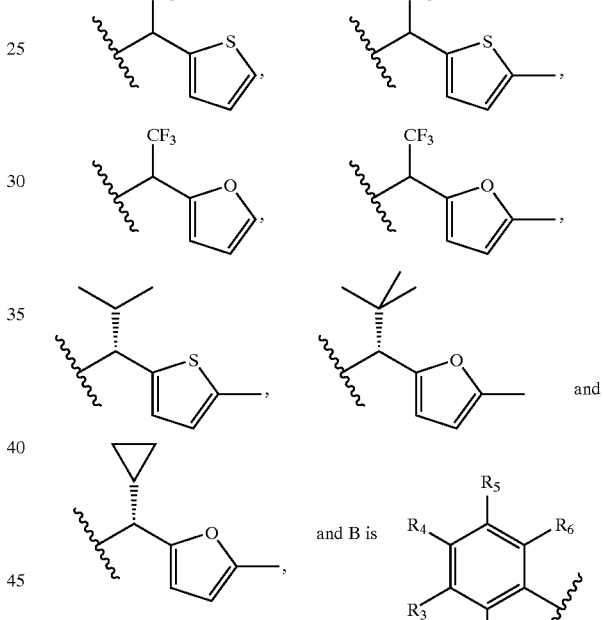

wherein, $R^2$ is —OH;

$R^3$ is $CONR^{13}R^{14}$;

$R^4$ is selected from the group consisting of H, $CH_3$, halo and $CF_3$;

$R^5$ is selected from the group consisting of H and cyano;

$R^6$ is selected from the group consisting of H, $CH_3$ and $CF_3$; and $R^{13}$ and $R^{14}$ are each methyl.

Representative compounds of the invention are listed below:

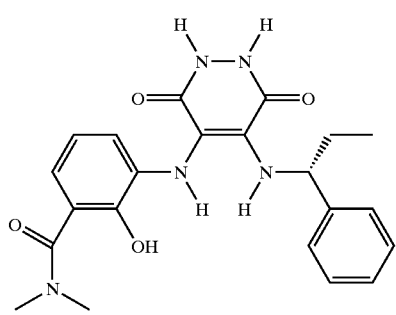
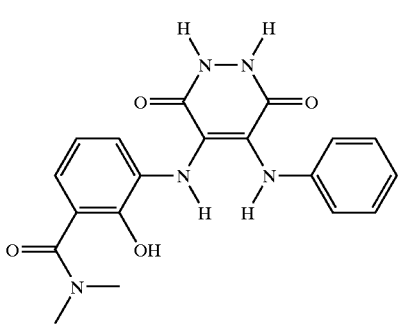
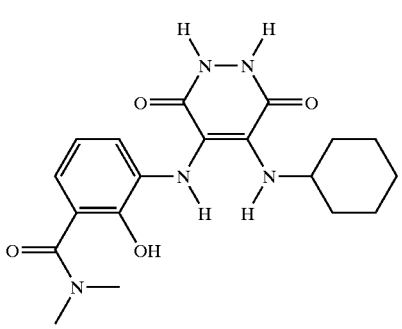
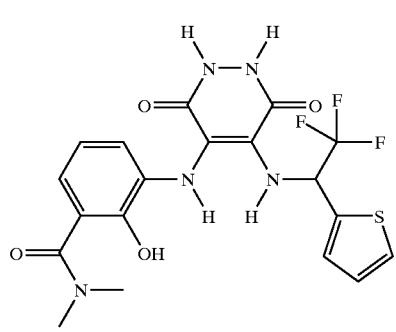
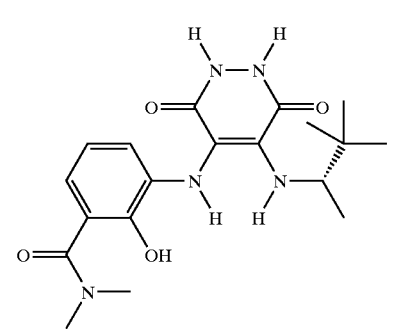
-continued
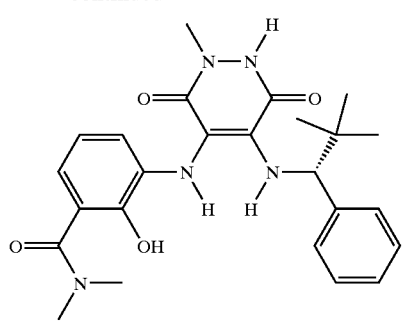
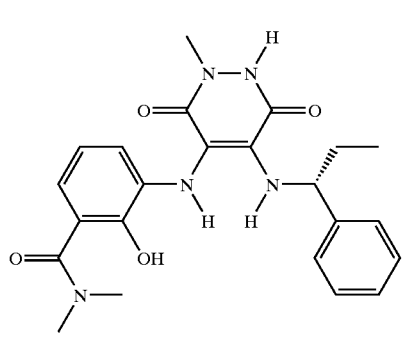
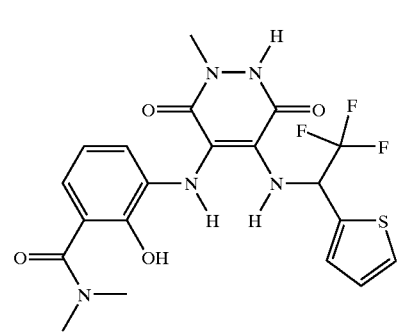
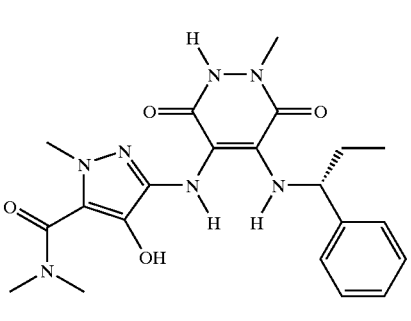
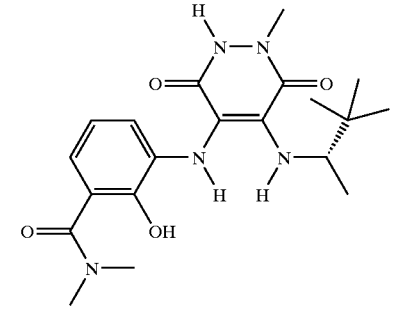

-continued
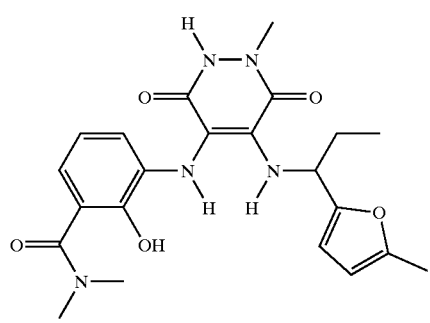
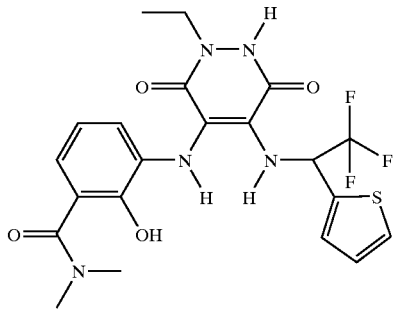

-continued
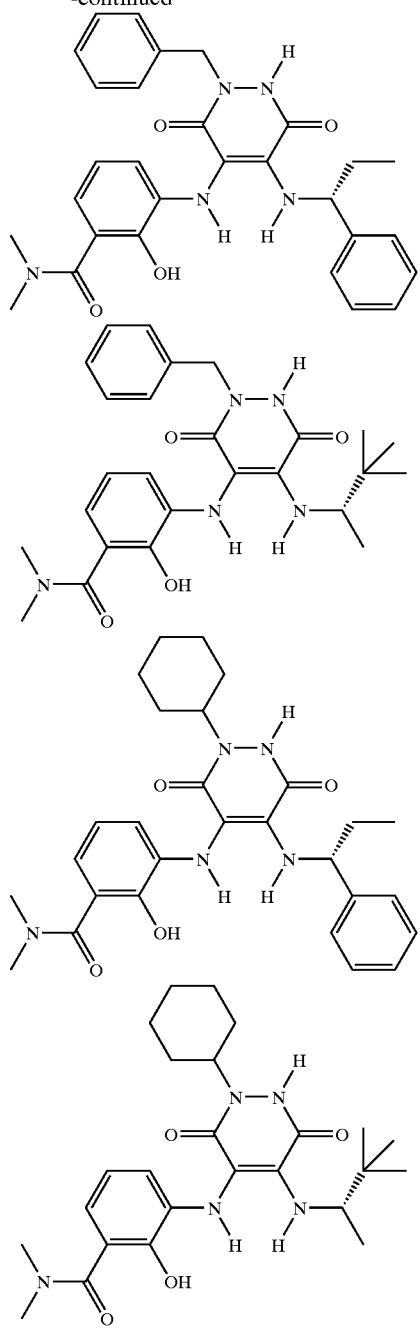
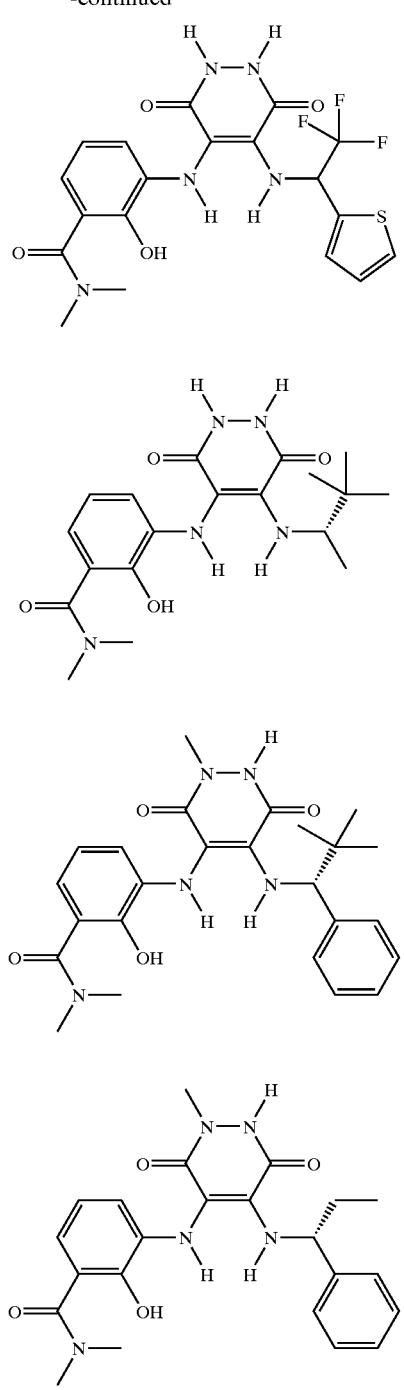
Preferred compounds of the invention are listed below:
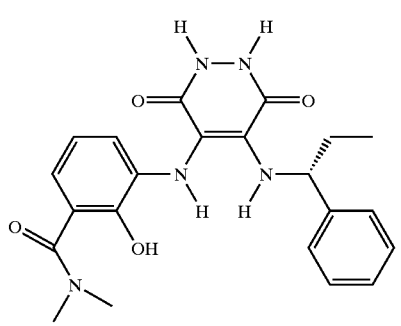

-continued
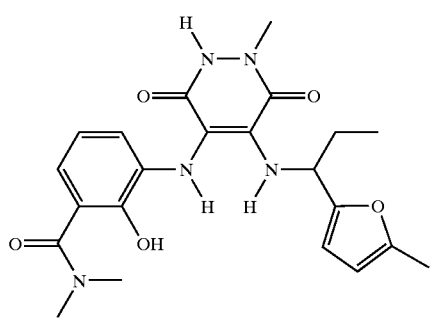
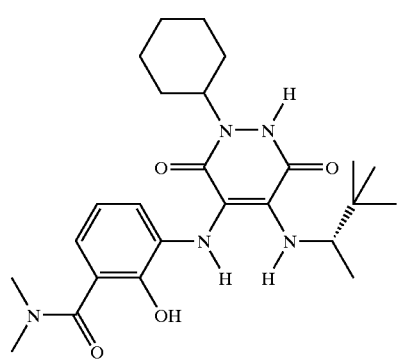
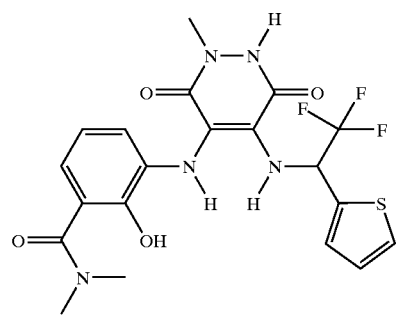
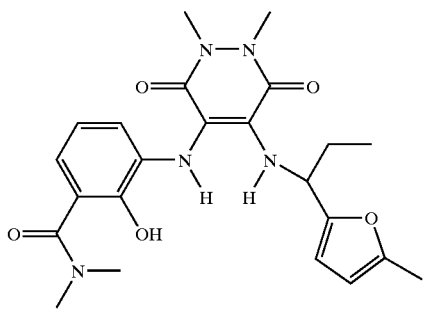
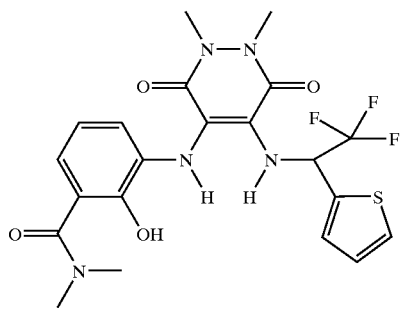
-continued
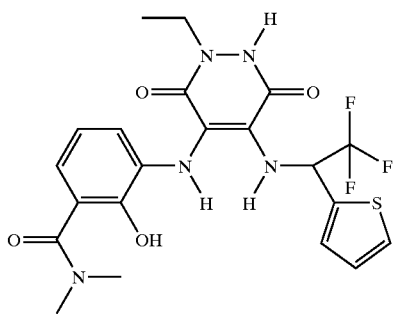
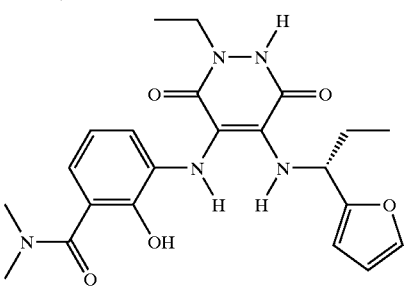
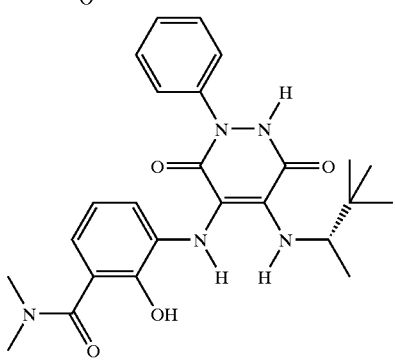
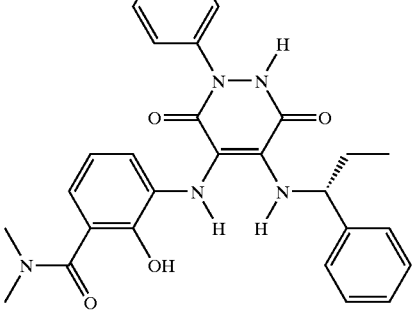
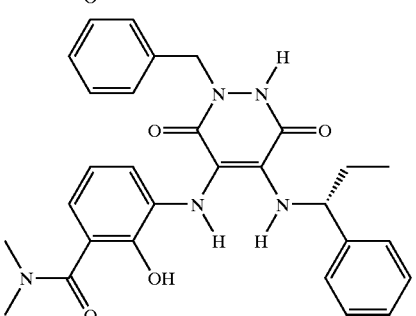

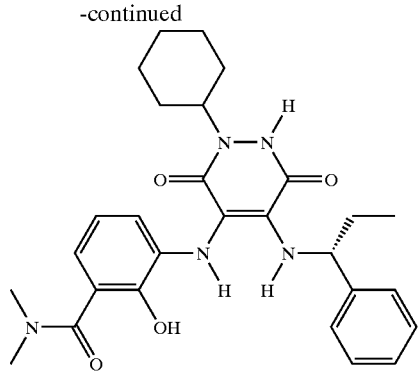
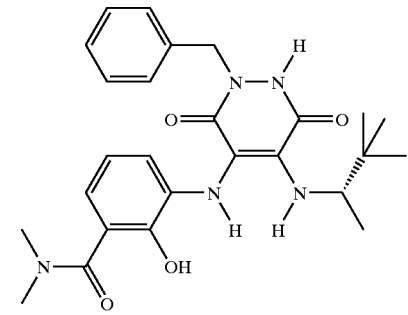
More preferably compounds of the invention are listed below:
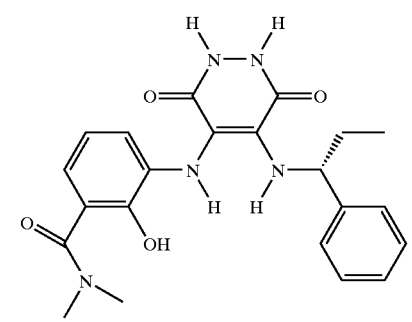
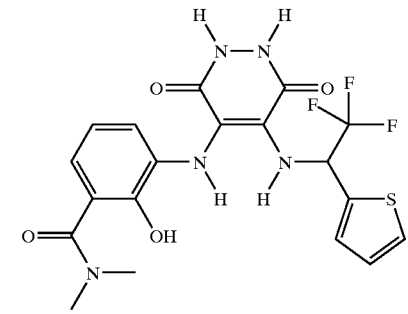
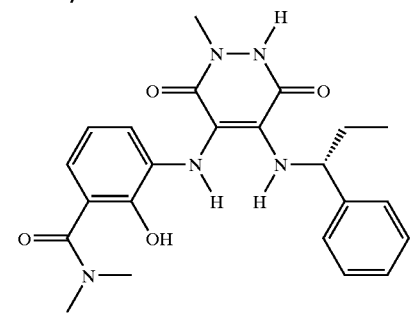
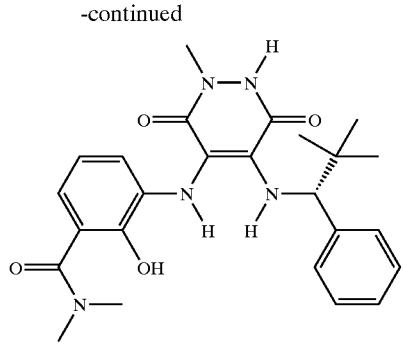
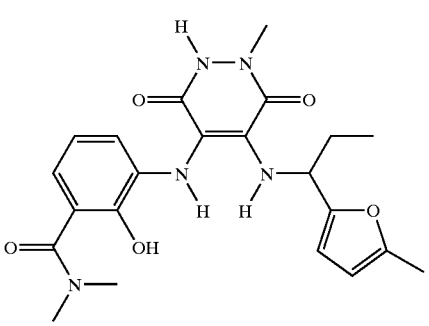
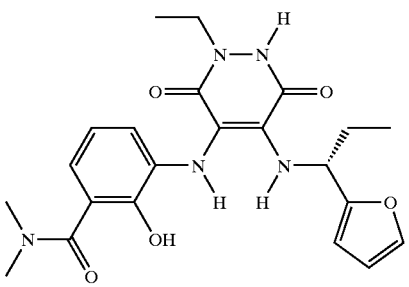
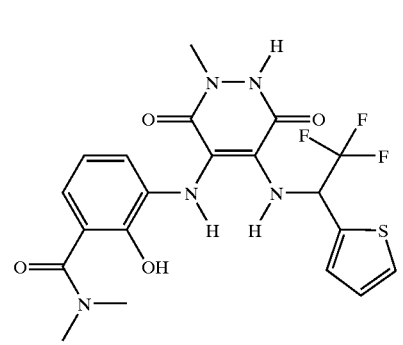
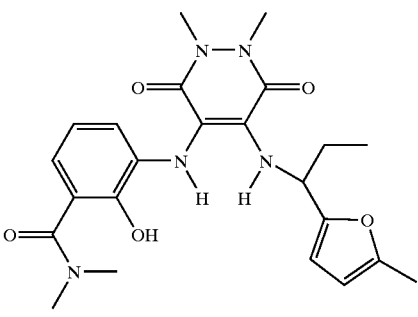

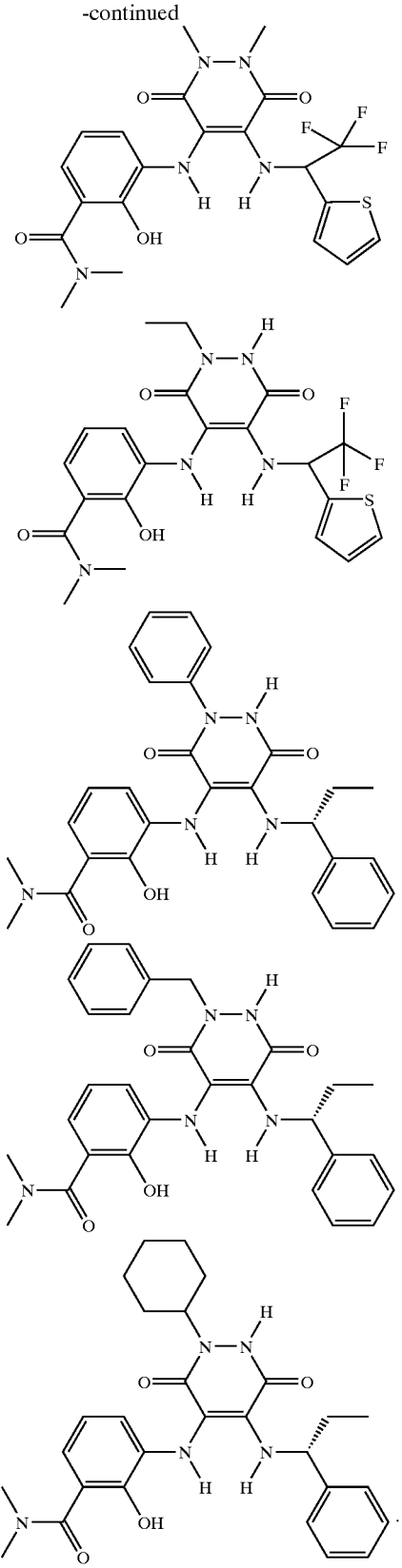

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, or by separating isomers of a compound of formula (I).

Compounds of formula (I) can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula (I) may form pharmaceutically acceptable salts with organic and inorganic acids or bases. Examples of suitable bases for salt formation include but are not limited to sodium hydroxide, lithium hydroxide, potassium hydroxide, and calcium hydroxide. Salts of phenols can be made by heating acidic compounds with any of the above mentioned bases according to procedures well known to those skilled in the art. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, lithium hydroxide, potassium hydroxide, calcium hydroxide, potassium carbonate, ammonia or sodium bicarbonate. The neutral forms differ from their respective salt forms somewhat in certain physical properties, such as solubility in polar solvents, but the salts are otherwise equivalent to their respective neutral forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

The compounds of the invention may also be delivered by direct application to the tumor site following surgery, e.g., in a sponge preparation.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

Another aspect of the invention is a method for treating cancer, comprising administering to a patient in need thereof, concurrently or sequentially, a therapeutically effective amount of (a) a compound of formula (I) and (b) a chemotherapeutic agent (i.e. an antineoplastic agent, microtubule affecting agent or anti-angiogenesis agent).

In a preferred embodiment, a compound of formula (I) is combined with one of the following antineoplastic agents: gemcitabine, paclitaxel (Taxol®), 5-Fluorouracil (5-FU), cyclophosphamide (Cytoxan®), temozolomide, taxotere or Vincristine.

Classes of compounds that can be used as the chemotherapeutic agent (antineoplastic agent) include: alkylating agents, antimetabolites, natural products and their derivatives, hormones, anti-hormones, anti-angiogenic agents and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-α), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methy-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Anti-angiogenic agents include Marimastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, taxotere and Taxol.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science*, 274:2009) estramustine, nocodazole, MAP4, and the like. Examples of such agents are also described in the scientific and patent literature, see, e.g., Bulinski (1997) *J. Cell Sci.* 110:30553064; Panda (1997) Proc. Natl. Acad. Sci. USA 94:10560–10564; Muhlradt (1997) Cancer Res. 57:3344–3346; Nicolaou (1997) *Nature* 387:268–272; Vasquez (1997) *Mol. Biol. Cell.* 8:973–985; Panda (1996) *J. Biol. Chem.* 271:29807–29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology*, 6: 17–23, Horwitz (1992) *Trends Pharmacol. Sci.* 13: 134–146, Rowinsky (1990) *J. Natl. Canc. Inst.* 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.*, 45(2): 145–150.

Other methods of screening compounds for desired activity are well known to those of skill in the art. Typically such assays involve assays for inhibition of microtubule assembly and/or disassembly. Assays for microtubule assembly are described, for example, by Gaskin etal (1974) *J. Molec. Biol.*, 89:737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

The amount and frequency of administration of the compounds of formula (I) and the chemotherapeutic agents and/or radiation therapy will be regulated according to the judgment of the attending clinician (physician) considering such factors as age, condition and size of the patient as well as severity of the disease being treated. A dosage regimen of the compound of formula (I) can be oral administration of from 10 mg to 2000 mg/day, preferably 10 to 1000 mg/day, more preferably 50 to 600 mg/day, in two to four (preferably two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In the methods of this invention, a compound of formula (I) is administered concurrently or sequentially with a chemotherapeutic agent and/or radiation; Thus, it is not necessary that, for example, the chemotherapeutic agent and the compound of formula (I), or the radiation and the compound of formula (I), should be administered simultaneously or essentially simultaneously. The advantage of a simultaneous or essentially simultaneous administration is well within the determination of the skilled clinician. Also, in general, the compound of formula (I) and the chemotherapeutic agent do not have to be administered in the same pharmaceutical composition, and may, because of different physical and chemical characteristics, have to be administered by different routes. For example, the compound of formula (I) may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of a compound of formula (I), and chemotherapeutic agent and/or radiation will depend upon the diagnosis of the attending physicians and their judgement of the condition of the patent and the appropriate treatment protocol.

The compound of formula (I), and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound of formula (I).

If the compound of formula (I) and the chemotherapeutic agent and/or radiation are not administered simultaneously or essentially simultaneously, then the initial order of administration of the compound of formula (I) and the chemotherapeutic agent and/or radiation, may not be important. Thus, the compound of formula (I) may be administered first followed by the administration of the chemotherapeutic agent and/or radiation; or the chemotherapeutic agent and/or radiation may be administered first followed by the administration of the compound of formula (I). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of formula (I) followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent-i.e., the compound of formula (I), chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

BIOLOGICAL EXAMPLES

The compounds of the present invention are useful in the treatment of CXC-chemokine mediated conditions and diseases. This utility is manifested in their ability to inhibit IL-8 and GRO-α chemokine which may be demonstrated by the following in vitro assays.

Receptor Binding Assays:

CXCR1 SPA Assay

For each well of a 96 well plate, a reaction mixture of 10 μg hCXCR1-CHO overexpressing membranes (Biosignal) and 200 μg/well WGA-SPA beads (Amersham) in 100 μl is prepared in CXCR1 assay buffer (25 mM HEPES, pH 7.8, 2 mM $CaCl_2$, 1 mM $MgCl_2$, 125 mM NaCl, 0.1% BSA) (Sigma). A 0.4 nM stock of ligand, [125]-IL-8 (NEN) is prepared in the CXCR1 assay buffer. 20× stock solutions of test compounds are prepared in DMSO (Sigma). A 6× stock solution of IL-8 (R&D) is prepared in CXCR2 assay buffer. The above solutions are added to a 96-well assay plate (PerkinElmer) as follows: 10 μl test compound or DMSO, 40 μl CXCR1 assay buffer or IL-8 stock, 100 μl of reaction mixture, 50 μl of ligand stock (Final [Ligand]=0.1 nM). The assay plates are shaken for 5 minutes on plate shaker, then incubated for 8 hours before cpm/well are determined in Microbeta Trilux counter (PerkinElmer). % Inhibition of Total binding-NSB (250 nM IL-8) is determined for IC50 values.

CXCR2 SPA Assay

For each well of a 96 well plate, a reaction mixture of 4 μg hCXCR2-CHO overexpressing membranes (Biosignal) and 200 μg/well WGA-SPA beads (Amersham) in 100 μl is prepared in CXCR2 assay buffer (25 mM HEPES, pH 7.4. 2 mM $CaCl_2$, 1 mM $MgCl_2$). A 0.4 nM stock of ligand, [125]-IL-8 (NEN), is prepared in the CXCR2 assay buffer. 20× stock solutions of test compounds are prepared in DMSO (Sigma). A 6× stock solution of GRO-A (R&D) is prepared in CXCR2 assay buffer. The above solutions are added to a 96-well assay plate (PerkinElmer or Corning) as follows: 10 μl test compound or DMSO, 40 μl CXCR2 assay buffer or GRO-α stock, 100 μl of reaction mixture, 50 μl of ligand stock (Final [Ligand]=0.1 nM). When 40× stock solutions of test compounds in DMSO are prepared, then the above protocol is used except instead 5 ll test compound or DMSO and 45 μl CXCR2 assay buffer are used. The assay plates are shaken for 5 minutes on a plate shaker, then incubated for 2–8 hours before cpm/well are determined in Microbeta Trilux counter (PerkinElmer). % Inhibition of total binding minus non-specific binding (250 nM Gro-α or 50 μM antagonist) is determined and IC50 values calculated.

Calcium Fluorescence Assay (FLIPR)

HEK 293 cells stably transfected with hCXCR2 and GαJq are plated at 10,000 cells per well in a Poly-D-Lysine Black/Clear plate (Becton Dickinson) and incubated 48 hours at 5% $CO_2$, 37° C. The cultures are then incubated with 4 mM fluo-4, AM (Molecular Probes) in Dye Loading Buffer (1% FBS, HBSS w. Ca & Mg, 20 mM HEPES (Cellgro), Probenicid (Sigma)) for 1 hour. The cultures are washed with wash buffer (HBSS w Ca, & Mg, 20 mM HEPES, Probenicid (2.5 mM)) three times, then 100 μl/well wash buffer is added.

During incubation, compounds are prepared as 4× stocks in 0.4% DMSO (Sigma) and wash buffer and added to their respective wells in the first addition plate. IL-8 or GRO (R&D Systems) concentrations are prepared 4×in wash buffer+0.1% BSA and added to their respective wells in second addition plate.

Culture plate and both addition plates are then placed in the FLIPR imaging system to determine change in calcium fluorescence upon addition of compound and then ligand. Briefly, 50 μl of compound solutions or DMSO solution is added to respective wells and change in calcium fluorescence measured by the FLIPR for 1 minute. After a 3 minute incubation within the instrument, 50 μl of ligand is then added and the change in calcium fluorescence measured by the FLIPR instrument for 1 minute. The area under each stimulation curve is determined and the values are used to determine % Stimulation by compound (agonist) and % Inhibition of Total Calcium response to ligand (0.3 nM IL-8 or GRO-α) for IC50 values of the test compounds.

Chemotaxis Assays for 293CXCR2

A chemotaxis assay is setup using Fluorblok inserts (Falcon) for 293-CXCR2 cells (HEK-293 cells overexpressing human CXCR2). The standard protocol used at present is as follows:

1. Inserts are coated with collagenIV (2 ug/ml) for 2 hrs at 37° C.
2. The collagen is removed and inserts are allowed to air dry overnight.
3. Cells are labeled with 10 uM calcein AM (Molecular Probes) for 2 hrs. Labeling is done in complete media with 2% FBS.
4. Dilutions of compound are made in minimal media (0.1% BSA) and placed inside the insert which is positioned inside the well of a 24 well plate. Within the well is IL-8 at a concentration of 0.25 nM in minimal media. Cells are washed and resuspended in minimal media and placed inside the insert at a concentration of 50,000 cells per insert.
5. Plate is incubated for 2 hrs and inserts are removed and placed in a new 24 well. Fluorescence is detected at excitation=485 nM and emission=530 nM.

Cytotoxicity Assays

A cytotoxicity assay for CXCR2 compounds is conducted on 293-CXCR2 cells. Concentrations of compounds are tested for toxicity at high concentrations to determine if they may be used for further evaluation in binding and cell based assays. The protocol is as follows:

1. 293CXCR2 cells are plated overnight at a concentration of 5000 cells per well in complete media.
2. Dilutions of compound are made in minimal media w/0.1% BSA. Complete media is poured off and the dilutions of compound are added. Plates are incubated for 4, 24 and 48 hrs. Cells are labeled with 10 uM calcein AM for 15 minutes to determine cell viability. Detection method is the same as above.

Soft Agar Assay 10,000 SKMEL-5 cells/well are placed in a mixture of 1.2% agar and complete media with various dilutions of compound. Final concentration of agar is 0.6%. After 21 days viable cell colonies are stained with a solution of MTT (1 mg/ml in PBS). Plates are then scanned to determine colony number and size. $IC_{50}$ is determined by comparing total area vs. compound concentration.

Compounds of this invention may exhibit a range of CXCR2 receptor binding activities from about 1 nM to about 10,000 nM.

Compounds of formula (I) may be produced by processes known to those skilled in the art in the following reaction schemes and in the preparations and examples below.

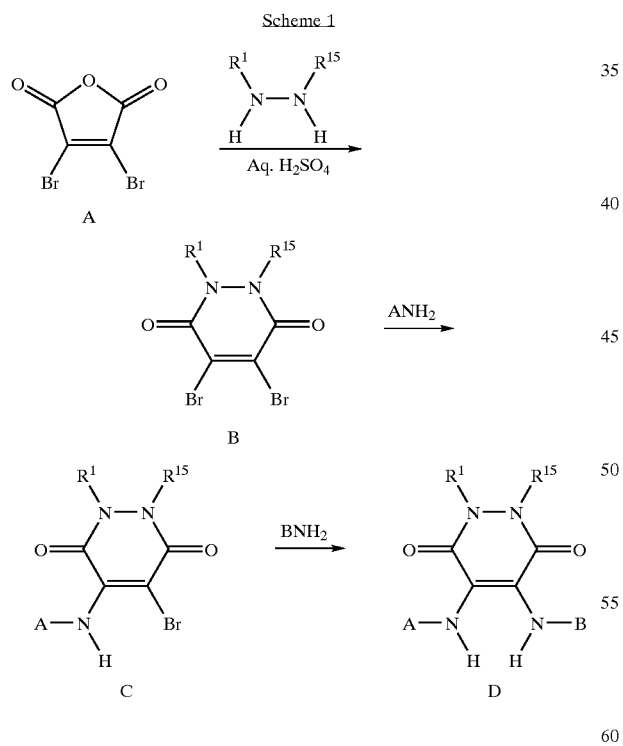

Condensation of dibromomaleic anhydride with a substituted or unsubstituted hydrazine would give the cyclic hydrazide derivative B. Condensation of B with one equivalent of an amine ($ANH_2$) would give C, while the addition of a second amine ($BNH_2$) would give D.

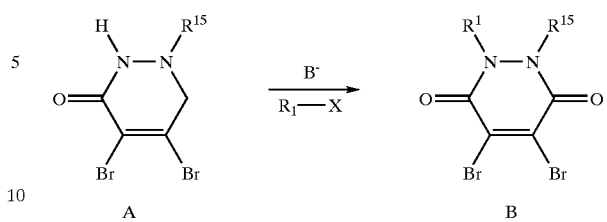

Alternatively, a cyclic hydrazide with an available acidic N—H could be deprotonated with a base and alkylated by a suitable electrophile to give the corresponding N-substituted cyclic hydrazide. This intermediate could be carried further to the desired target as described in Scheme I.

The following examples illustrate the preparation of some of the compounds of the invention and are not to be construed as limiting the invention disclosed herein. Alternate mechanistic pathways and analogous structures will be apparent to those skilled in the art.

Preparative Example 1

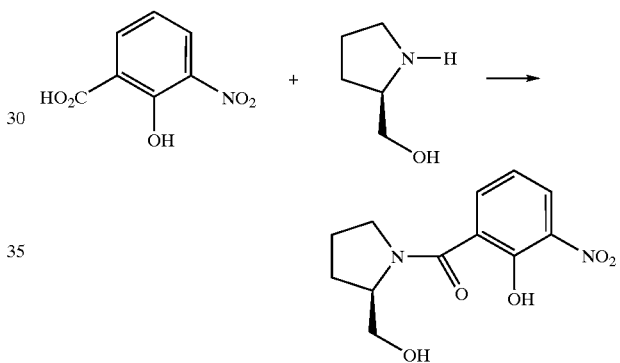

3-Nitrosalicylic acid (500 mg, 2.7 mmol), DCC (563 mg) and ethyl acetate (10 mL) were combined and stirred for 10 min. (R)-(−)$_2$-pyrrolidinemethanol (0.27 mL) was added and the resulting suspension was stirred at room temperature overnight. The solid was filtered and the filtrate washed with 1N NaOH. The aqueous phase was acidified and extracted with EtOAc. The resulting organic phase was dried over anhydrous $MgSO_4$, filtered and concentrated in vacuo. Purification of the residue by preparative plate chromatography (silica gel, 5% MeOH/$CH_2Cl_2$ saturated with AcOH) gave the product (338 mg, 46%, $MH^+$=267).

Preparative Example 2

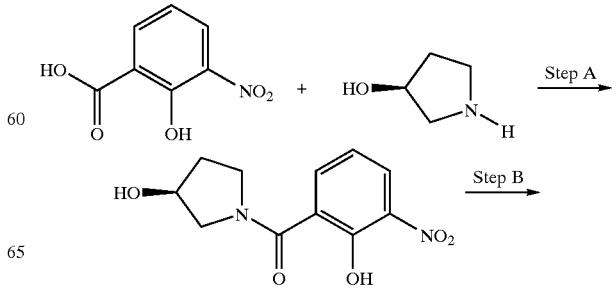

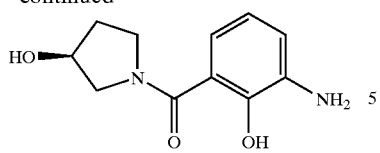

3-Nitrosalicylic acid (9.2 g), bromotripyrrolidinophosphonium hexafluorophosphate (PyBroP, 23 g) and N,N-diisopropylethylamine (DIEA, 26 mL) in anhydrous CH$_2$Cl$_2$ (125 mL) were combined and stirred at 25° C. for 30 min. (R)-(+)-3-pyrrolidinol (8.7 g) in CH$_2$Cl$_2$ (25 mL) was added over 25 min and the resulting suspension was stirred at room temperature overnight. The mixture was extracted with 1M NaOH (aq) and the organic phase was discarded. The aqueous phase was acidified with 1M HCl (aq), extracted with EtOAc, dried over anhydrous Na$_2$SO$_4$, filtered and concentrated in vacuo to afford the crude product (7 g) which was used without further purification.

Step B

The crude product from Step A above was stirred with 10% Pd/C (0.7 g) in MeOH (100 mL) under a hydrogen gas atmosphere overnight. The reaction mixture was filtered through celite, the filtrate concentrated in vacuo, and the resulting residue purified by column chromatography (silica gel, 10% MeOH/CH$_2$Cl$_2$, saturated with NH$_4$OH) to give the product (2.5 g, 41%, MH$^+$=223).

Preparative Example 3–9

Following the procedures set forth in Preparative Example 2 but using the carboxylic acid, amine, and appropriate coupling agent (PyBrop) listed in the Table below, the amide product was obtained and used without further purification.

| Prep. Ex. | Carboxylic acid | Amine | Amide Product | 1. Coupling Agent<br>2. % Yield<br>3. MH$^+$ |
|---|---|---|---|---|
| 3 | | | | 1. PyBrop<br>2. 87%, 86%<br>3. 181 |
| 4 | | | | 1. PyBroP<br>2. 49%<br>3. 209 |
| 5 | | NH$_3$ | | 1. PyBroP<br>2. 95%<br>3. 153 |
| 6 | | | | 1. PyBroP<br>2. 83%<br>3. 167 |
| 7 | | | | 1. PyBroP<br>2. 76%<br>3. 223 |
| 8 | | | | 1. PyBroP<br>2. 59, 69<br>3. 207 |

| Prep. Ex. | Carboxylic acid | Amine | Amide Product | 1. Coupling Agent 2. % Yield 3. MH+ |
|---|---|---|---|---|
| 9 | | | | 1. PyBroP 2. 49, 86 3. 237 |

Preparative Example 10

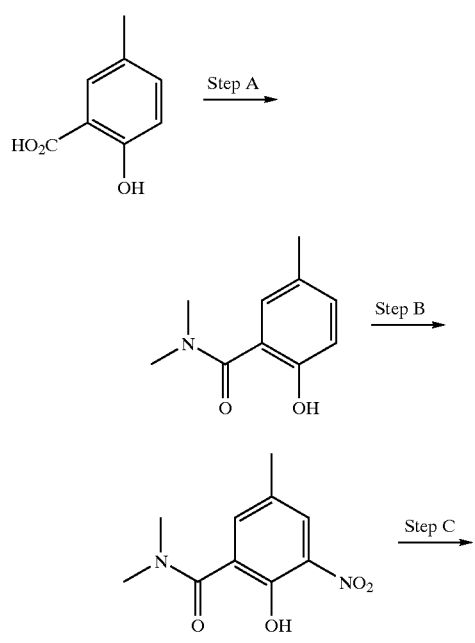

Preparative Example 11

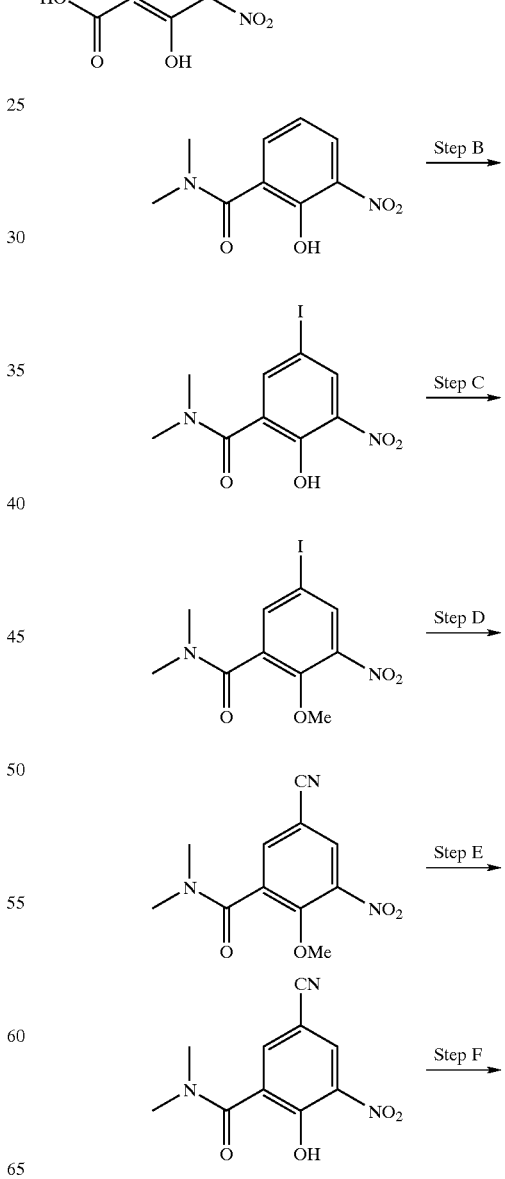

Step A

Following a similar procedure as in Preparative Example 1 except substituting methylamine (2M in THF, 33 mL) for (R)-(−)-2-pyrrolidinemethanol and 5-thylsalicylic acid (5 g) for 3-nitrosalicylic acid, the product was prepared (6.5 g).

Step B

Nitric acid (0.8 mL) in $H_2SO_4$ was added to a cooled (−20° C.) suspension of the product from Step A above (3 g) in $H_2SO_4$ (25 mL). The mixture was treated with 50% NaOH (aq) dropwise, extracted with $CH_2Cl_2$, dried over anhydrous $MgSO_4$, filtered and concentrated in vacuo to give the product as a solid (2.1 g, 44%, MH+=225).

Step C

The product was prepared following a similar procedure as described in Preparative Example 2, Step B (0.7 g, 99%, MH+=195).

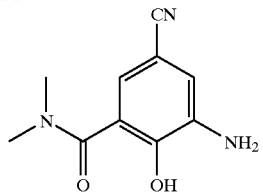

Step A

Following a similar procedure as in Preparative Example 2 Step A, except substituting dimethylamine for (R)(–)-2-pyrrolidinemethanol, the product was prepared.

Step B

The product from step A above (8 g) was combined with iodine (9.7 g), silver sulfate (11.9 g), EtOH (200 mL) and water (20 mL) and stirred overnight. Filtration, concentration of the filtrate, re-dissolution in $CH_2Cl_2$ and washing with 1M HCl (aq) gave an organic solution which was dried over anhydrous $MgSO_4$, filtered and concentrated in vacuo to afford the product (7.3 g, 57%, $MH^+$=337).

Step C

The product from Step B above (3.1 g) was combined with DMF (50 mL) and MeI (0.6 mL). NaH (60% in mineral oil, 0.4 g) was added portionwise and the mixture was stirred overnight. Concentration in vacuo afforded a residue which was diluted with $CH_2Cl_2$, washed with 1M NaOH (aq), dried over anhydrous $MgSO_4$, filtered and concentrated in vacuo. Purification through a silica gel column (EtOAc/Hex, 1:1) gave the product (1.3 g, 41%, $MH^+$=351).

Step D

The product from Step D above (200 mg), $Zn(CN)_2$ (132 mg), $Pd(PPh_3)_4$ (130 mg) and DMF (5 mL) were heated at 80° C. for 48 hrs, then cooled to room temperature and diluted with EtOAc and 2M $NH_4OH$. After shaking well, the organic extract was dried over anhydrous $MgSO_4$, filtered, concentrated in vacuo and purified by preparative plate chromatography (Silica, EtOAc/Hex, 1:1) to give the product (62 mg, 44%, $MH^+$=250).

Step E $BBr_3$ (1.3 mL, 1M in $CH_2Cl_2$) was added to a $CH_2Cl_2$ solution (5 mL) of the product from step D above (160 mg) and stirred for 30 min. The mixture was diluted with water, extracted with $CH_2Cl_2$, dried over anhydrous $MgSO_4$, filtered, and concentrated in vacuo to give the product (158 mg, $MH^+$=236).

Step F

A mixture of the product from step E above (160 mg), platinum oxide (83%, 19 mg), and EtOH (20 mL) was stirred under hydrogen (25–40 psi) for 1.5 hr. Filtration through celite and concentration in vacuo afforded the product (165 mg, $MH^+$=206).

Preparative Example 12

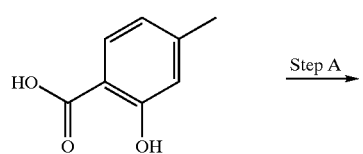

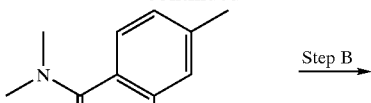

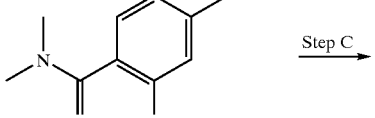

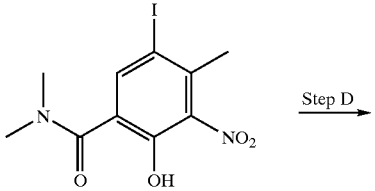

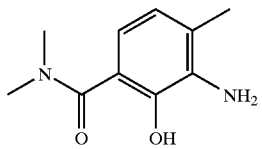

Step A

Following a similar procedure as in Preparative Example 1 except substituting dimethylamine (2M in THF, 50 mL) for $(R^1(-)-)_2$-pyrrolidinemethanol and 4-methylsalicylic acid (15 g) for 3-nitrosalicylic acid, the product was prepared (6.3 g, 35%).

Step B

The product from step A above (1.5 g) was combined with iodine (2.1 g), $NaHCO_3$ (1.1 g), EtOH (40 mL) and water (10 mL) and stirred overnight. Filtration, concentration of the filtrate, re-dissolution in $CH_2Cl_2$ and washing with 1M HCl (aq) gave an organic solution which was dried over anhydrous $MgSO_4$, filtered and concentrated in vacuo. Purification by flash column chromatography (silica gel, 0.5–0.7% $MeOH/CH_2Cl_2$) gave the product (0.3 g, 57%, $MH^+$=306).

Step C

Nitric acid (3.8 mL) in AcOH (10 mL) was added to the product from Step B above (0.8 g) and the mixture was stirred for 40 min. The mixture was diluted with water and extracted with $CH_2Cl_2$, dried over anhydrous $MgSO_4$, filtered and concentrated in vacuo to give the product as a solid (0.8 g, 92%, $MH^+$=351).

Step D

A mixture of the product from step C above (800 mg), 10% Pd/C (100 mg), and EtOH/MeOH (40 mL) was stirred in a parr shaker under hydrogen (45 psi) for 1.5 hr. Filtration through celite and concentration in vacuo afforded the title product after purification by preparative plate chromatography (Silica, 10% $MeOH/CH_2Cl_2$, saturated with $NH_4OH$) to give the product (92 mg, 22%, $MH^+$=195).

Preparative Example 13

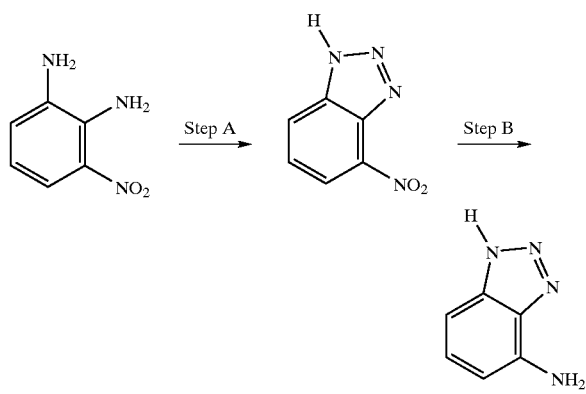

Step A

3-Nitro-1,2-phenylenediamine (10 g), sodium nitrite (5.4 g) and acetic acid (20 mL) were heated at 60° C. overnight, then concentrated in vacuo, diluted with water and extracted with EtOAc. The product precipitated from the organic phase (5.7 g) as a solid and used directly in step B.

Step B

The product from Step A above (2.8 g) was stirred with 10% Pd/C (0.3 g) in MeOH (75 mL) under a hydrogen gas atmosphere overnight. The reaction mixture was filtered through celite and the filtrate concentrated in vacuo, to give the product (2.2 g, $MH^+=135$).

Preparative Example 14

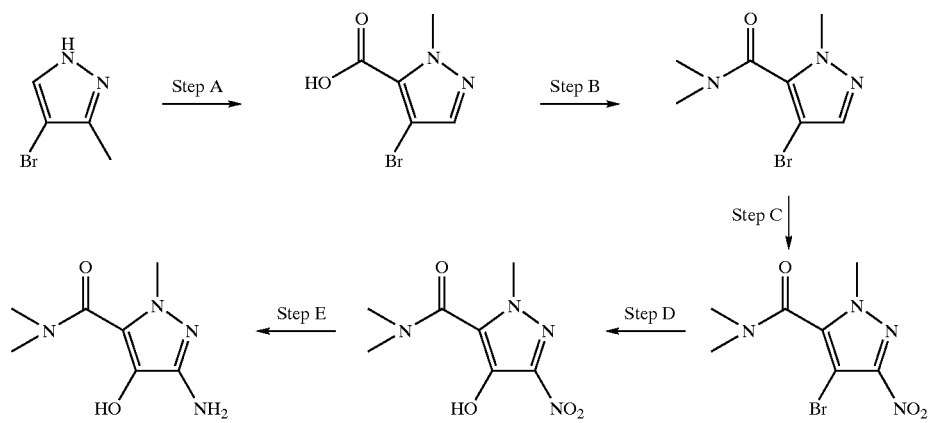

Step A

4-Bromopyrazole-3-carboxylic acid was prepared according to known methods, see: Yu. A. M.; Andreeva, M. A.; Perevalov, V. P.; Stepanov, V. I.; Dubrovskaya, V. A.; and Seraya, V. I. in Zh. Obs. Khim. (Journal of General Chemistry of the USSR) 1982, 52, 2592, and refs cited therein.

Step B

To a solution of 4-bromopyrazole-3-carboxylic acid (2.0 g), available from step A, in 65 mL of anhydrous DMF was added bromotripyrrolidinophosphonium hexafluorophosphate (PyBrop, 4.60 g), dimethyl amine (10 mL, 2.0 M in THF) and diisopropylethyl amine (5.2 mL) at 25° C. The mixture was stirred for 26 h, and concentrated under reduced pressure to an oily residue. This residue was treated with a 1.0 M NaOH aqueous solution, and extracted with ethyl acetate (4×50 mL). The organic extracts were combined, washed with brine, and dried with anhydrous $Na_2SO_4$. Removal of solvents yielded an oil, which was purified by preparative thin layer chromatography, eluting with $CH_2Cl_2$—MeOH (20:1), to give 1.09 g of the amide product (48%, MH=232.0).

Step C

To a solution of the amide (0.67 g), obtained from step B, in 8 mL of concentrated sulfuric acid at 0° C. was added potassium nitrate (1.16 g) in small portions. The cooling bath was removed and the mixture was heated at 110° C. for 6 h. After cooled to 25° C., the mixture was poured into 80 mL of $H_2O$, and an additional 20 mL of $H_2O$ was used as rinsing. The aqueous mixture was extracted with $CH_2Cl_2$ (100 mL×4). The combined extracts were washed with brine (50 mL), sat. $NaHCO_3$ aqueous solution (50 mL), brine (50 mL), and dried over $Na_2SO_4$. Evaporation of solvent gave a light yellow oil, which solidified on standing. The crude product was purified by flash column chromatography, eluting with $CH_2Cl_2$—MeOH (1:0, 50:1 and 40:1). Removal of solvents afforded 0.521 g (65%) of the product as a solid ($MH^+=277.1$)

Step D

The product (61 mg) obtained from step C was dissolved in 3 mL of THF. To this solution at −78° C. was added dropwise along the inside wall of the flask a 1.6 M solution of n-butyl lithium in hexane. After 45 min, a solution of methyl borate (0.1 mL) in THF (1.0 mL) was added. After 1.5 h, a solution of acetic acid in THF (0.25 mL, 1:10 v/v) was added to the cold mixture. Stirring was continued for 10 min, and a 30 wt % aqueous hydrogen peroxide solution (0.1 mL) was added. An additional portion of hydrogen peroxide aqueous solution (0.05 mL) was added 20 min later. The cooling bath was removed, and the mixture was stirred at 25° C. for 36 h. The yellowish mixture was poured into 30 mL of $H_2O$, and the aqueous mixture was extracted with ethyl acetate (30 mL×4). The extracts were combined, washed with brine (10 mL), 5% $NaHCO_3$ aqueous solution (10 mL) and brine (10 mL). The organic layer was dried with $Na_2SO_4$ and concentrated under reduced pressure to a residue, which was purified by preparative thin layer chromatography eluting with $CH_2Cl_2$—MeOH (20:1) to give the hydroxylated product (5 mg, 10%, $MH^+=215.3$).

Step E

If one were to treat the hydroxylated product of Step D with $H_2$ under the conditions of 10% palladium on carbon in ethanol, one would obtain the hydroxyl-amino compound.

Preparative Example 15

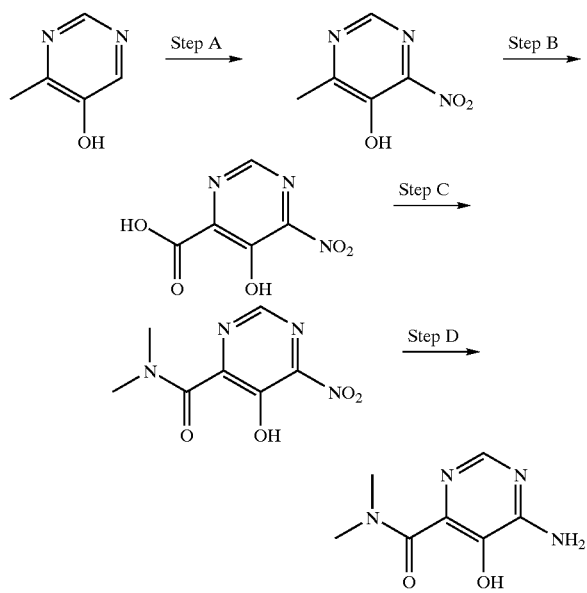

Step A

Following a similar procedure used in Preparative Example 12 Step C except starting with the known compound, 4-methyl-pyrimidin-51, the product of Step A could be prepared.

Step B

Following a similar oxidation procedure used in Preparative Example 14 Step A starting with the product from Step A above, the product of Step B could be prepared.

Step C

Following a similar procedure used in Preparative Example 10 Step A starting with the product from Step B above, the product of Step C could be prepared.

Step D

Following a similar procedure used in Preparative Example 11 Step F starting with the product of Step C above, the product of Step D could be prepared.

Preparative Example 16

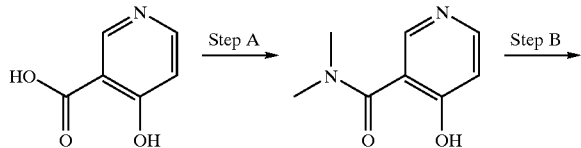

Step A

Following a similar procedure used in Preparative Example 10 Step A starting with the known 4-hydroxynicotinic acid, the product could be prepared.

Step B

Following a similar procedure used in Preparative Example 12 Step C starting with the product from Step A above, the product of Step B could be prepared.

Step C

Following a similar procedure used in Preparative Example 11 Step F starting with product from Step C above, the amine product could be prepared.

Preparative Example 17

Step A

Following a similar procedure used in Preparative Example 12 Step C but starting with the compound in Step A above, the nitro product could be prepared.

Step B

Stirring the nitro product from Step A above, with a suitable Pt or Pd catalyst and EtOH under a hydrogen atmosphere (1–4 atm), the amine product could be obtained.

Preparative Example 18

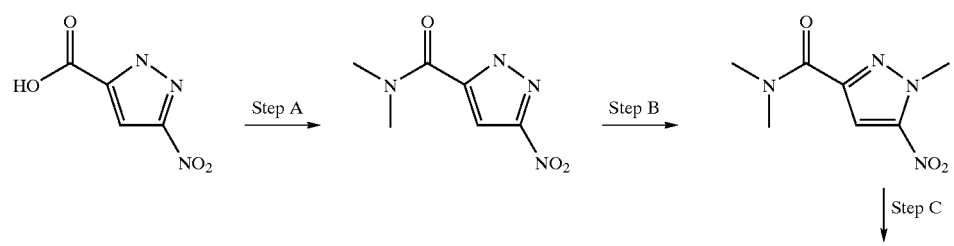

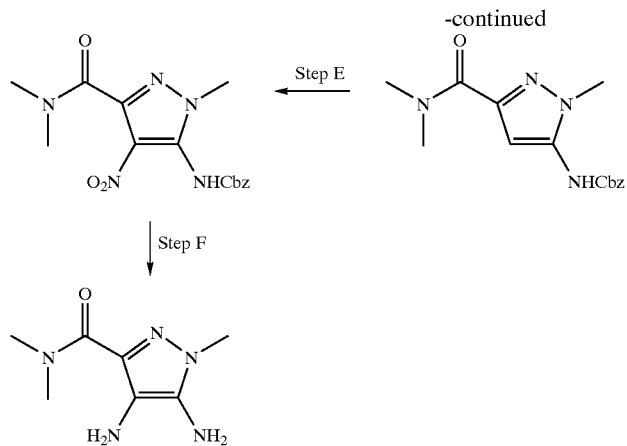

Step A

To a solution of 5-nitro-3-pyrazolecarboxylic acid (5.0 g, 31.83 mmol) in 160 mL of acetonitrile at room temperature was added bromotripyrrolidinophosphonium hexafluorophosphate (PyBrop, 14.9 g, 31.98 mmol) in small portions. A 2.0 M solution of dimethylamine in THF (40.0 mL, 80.0 mmol) was added to the mixture followed by a solution of diisopropylethylamine (14.0 mL, 80.2 mmol). After stirred for 36 h, the mixture was concentrated under reduced pressure to a residue, a mixture of solid and oil. Small volume of $CH_2Cl_2$ was added until all oily material was dissolved and fine colorless solid precipitated out. The solid was collected by filtration as the first crop of the product. The filtrate was concentrated to an oily residue which was treated with a mixture of $CH_2Cl_2$— hexanes (~1:1, v/v), and the colorless precipitation was filtered out as the second crop of the product. The combined solid product was further dried on high vacuum for several hours to afford 5.86 g (100%) of N,N'-dimethyl 5-nitro-3-pyrazolecarboxamide as a solid ($MH^+$=185.0).

Step B

To a solution of N,N'-dimethyl 5-nitro-3-pyrazole amide (5.86 g, 31.83 mmol, available from step A) in 215 mL of anhydrous THF at room temperature was added solid lithium methoxide in small portions. After 45 min, iodomethane was added dropwise. Stirring was continued for 2.5 days. The mixture was filtered through a 1.5-in silica gel pad, rinsing with large excess volume of ethyl acetate. The combined filtrate and rinsing were concentrated to a dark yellow oil, which was purified by flash column chromatography, eluting with hexanes, $CH_2Cl_2$, and $CH_2Cl_2MeOH$ (50:1). Removal of solvents afforded 5.10 g (81%) of N,N'-dimethyl 1-methyl-5-nitro-3-pyrazole amide as a solid ($MH^+$=199.0), contaminated by ~13% of 2-methylated isomer.

Step C

A solution of N, N'-dimethyl 1-methyl-5-nitro-3-pyrazolecarboxamide (5.10 g, 25.29 mmol), obtained from step B, in 250 mL of ethanol was degassed via house vacuum, and then refilled with nitrogen. Solid palladium (10% on activated carbon, wet with <50% water, 2.5 g) was added, the black suspension was degassed via house vacuum and then refilled with hydrogen gas supplied by a gas balloon. The mixture was stirred at room temperature under a hydrogen atmosphere for 4 h, and filtered through a Celite pad, which was rinsed with ethanol. The filtrate and rinsing were combined, concentrated under reduced pressure to give 4.17 g (98%) of the amino-pyrazole product as a solid ($MH^+$=169.0).

Step D

To a stirred solution of amino-pyrazole (1.0 g, 5.95 mmol), prepared in step C, in 40 mL of $CH_2Cl_2$ at room temperature was added benzyl chloroformate (2.7 mL, 17.97 mmol). Solid potassium carbonate (4.1 g, 29.71 mmol) was added in one portion. After 24 h, methanol (5 mL) was added to the mixture, and stirring was continued for additional 2 h. Insoluble material was removed by filtration, and washed with methanol. The combined filtrate and rinsing were concentrated under reduced pressure to a thick syrup, which was separated by preparative TLC ($CH_2Cl_2$13 MeOH= 30:1). The silica was extracted with MeOH and $CH_2Cl_2$, the extracts were filtered and concentrated under reduced pressure to yield 1.16 g (64%) of the pyrazole benzyl carbamate as a solid ($MH^+$=303.1).

Step: E

To a stirred solution of pyrazole benzyl carbamate (1.0 g, 3.31 mmol), obtained from step D, in 100 mL of toluene at room temperature was added "Clayfen" (see note below) (3.5 g) in one portion. The dark purplish suspension was heated to 70° C. and continued at 70–80° C. for 2.5 d. After cooled to room temperature, the mixture was filtered through a thin Celite pad. The solid residue and the filtration pad were rinsed with $CH_2Cl_2$, and filtered. The combined filtrates were concentrated to a yellowish oil, which was purified by preparative TLC ($CH_2Cl_2$—MeOH=20:1). The silica was extracted with $CH_2Cl_2$ and methanol, the extracts were filtered and concentrated under reduced pressure to give 0.822 g (72%) of the nitro-pyrazole benzyl carbamate as an oil ($MH^+$=348.1). Note: "Clayfen", clay-supported Iron (III) nitrate, was prepared according to literature procedures, see: Cornelis, A.; Laszlo, P. Synthesis, 1980, 849. To a stirred acetone solution (30 mL) at room temperature was added solid $Fe(NO_3)_3·9H_2O$ (1.8 g) in small portions. After 5 min, K-10 bentonite clay (2.4 g) was added. Stirring was continued for 30 min, and the resulting suspension was concentrated under reduced pressure (water bath temperature <=30° C.). The freshly prepared material was used right away in the reaction above.

Step F

A solution of nitro-pyrazole benzyl carbamate (410.0 g, 1.18 mmol), available from step E, in 20 mL of ethanol was degassed via house vacuum, and refilled with nitrogen. Solid palladium (10% on activated carbon, wet with <50% $H_2O$, 280.0 mg) was added. The black suspension was degassed via house vacuum, and refilled with hydrogen gas supplied by a gas balloon. The mixture was stirred for 20 h under a hydrogen atmosphere, and filtered through a 1-in Celite pad, rinsing with excess volume of methanol. The filtrate and rinsing were concentrated to a reddish oil, which was purified by preparative TLC (CH$_2$Cl$_2$—MeOH=15:1). The silica was extracted with methanol, the extracts were filtered, and the filtrate was concentrated under reduced pressure to an oil, which solidified while being dried on high vacuum, yielding 120.0 mg (56%) of diamino-pyrazole product (MH$^+$=184.0).

Preparative Example 19 mmol). A 1.0 M solution of methanesulfonyl chloride in CH$_2$Cl$_2$ (1.7 mL, 1.7 mmol) was added dropwise along the inside wall of the flask. The mixture as stirred for 2.5 h while the temperature of the cooling bath was increased slowly from −78° C. to −25° C. A saturated NaHCO$_3$ aqueous solution (5 mL) was added to the mixture, and it was further diluted with 25 mL of CH$_2$Cl$_2$. The cooling bath was removed, stirring was continued for an additional 1.5 h, and the layers were separated. The aqueous layer was extracted with CH$_2$Cl$_2$ (30 mL), and the combined organic layers were

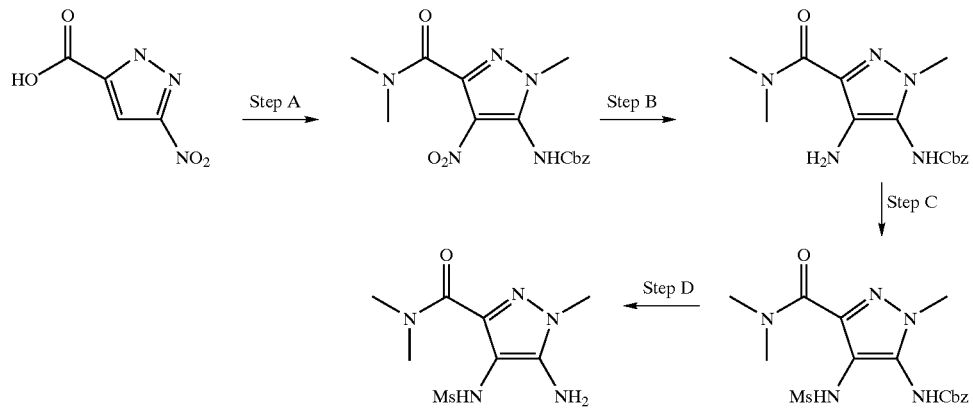

Step A

Nitro-pyrazole benzyl carbamate was prepared from 5-nitro-3 pyrazolecarboxylic acid according to the procedure described in Preparative Example 18.

Step B

To a solution of nitro-pyrazole benzyl carbamate (410.0 mg, 1.18 mmol), obtained from step A, in 17 mL of ethyl acetate at room temperature was added Tin (II) chloride dihydrate (1.33 g, 5.90 mmol) in one portion. The mixture was heated to 80° C. and continued for 2 h. after cooled to room temperature, a saturated NaHCO$_3$ aqueous solution was added dropwise to the mixture until pH approximately 7. An additional volume of ethyl acetate (20 mL) was added, the mixture was stirred overnight, and filtered through a 1-in Celite pad. The two layers of the filtrate were separated. The organic layer was washed with brine once. The aqueous washing was combined with the aqueous layer, and extracted with ethyl acetate once. The combined organic layers were dried with Na$_2$SO$_4$, filtered and concentrated, further dried on high vacuum, to afford 361.5 mg (97%) of amino-pyrazole benzyl carbamate as a solid (MH$^+$=318.1).

Step C

To a stirred solution of amino-pyrazole benzyl carbamate (180.0 mg, 0.57 mmol), prepared in step B, in 11 mL of CH$_2$Cl$_2$ at −78° C. was added triethylamine 0.32 mL, 2.30 washed with a saturated NaHCO$_3$ aqueous solution (30 mL) and brine (30 mL). The organic layer was dried by Na$_2$SO$_4$, and concentrated to an oil, which was purified by preparative TLC (CH$_2$ClMeOH=20:1). The silica was extracted with CH$_2$Cl$_2$ and methanol, the extracts were filtered and concentrated to a colorless oil, solidified while being dried on high vacuum, yielding 185.7 mg (83%) of the pyrazole methylsulfonamide as a solid (MH$^+$=396.1).

Step D

To a nitrogen flushed solution of pyrazole methylsulfonamide (275.0 mg, 0.70 mmol), from step C, in 10 mL of ethanol was added solid palladium (10% on activated carbon, wet with <50% water, 550.0 mg). The suspension was degassed via house vacuum, then filled with hydrogen gas supplied by a gas balloon. The mixture was stirred for 3.5 h under a hydrogen atmosphere, and filtered through a layer of Celite. The solid residue and the filtration pad were rinsed with ethanol and ethyl acetate, the combined filtrate and rinsing were concentrated under reduced pressure to give 173.0 mg (95%) of amino-pyrazole methylsulfonamide as a solid (MH$^+$=262.0).

Preparative Example 20

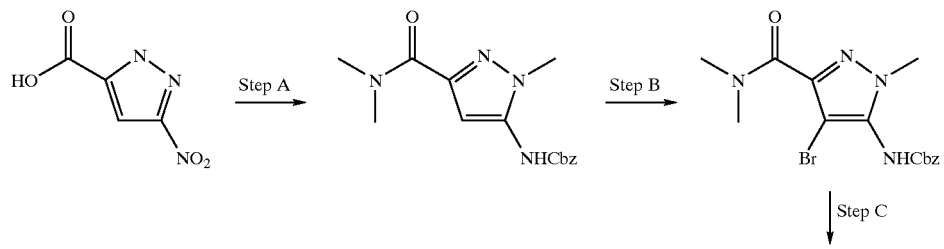

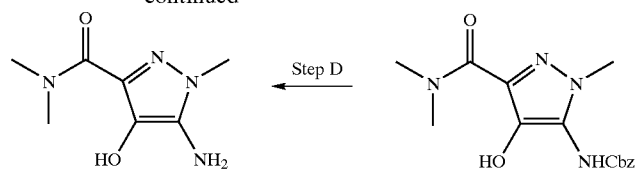

Step A

Pyrazole benzyl carbamate was prepared from 5-nitro-3-pyrazolecarboxylic acid in 4 steps according to the procedure described in Preparative Example 18.

Step B

To a solution of pyrazole benzyl carbamate (115.0 mg, 0.38 mmol), prepared in step A, in 6 mL of $CH_2Cl_2$ at room temperature was added solid potassium carbonate in one portion. A solution of bromine was added dropwise to the stirred mixture. After 6 h, 30 mL of $H_2O$ was added, and the mixture was extracted with $CH_2Cl_2$ (30 mL×3). The combined organic extracts were washed with a 10% $Na_2S_2O_3$ aqueous solution (20 mL), a saturated $NaHCO_3$ aqueous solution (20 mL) and brine (20 mL), and dried with $Na_2SO_4$. Evaporation of solvent gave a slightly yellow oil, which was purified by preparative TLC ($CH_2Cl_2$—MeOH=20:1). The silica was extracted with $CH_2Cl_2$ and methanol, the extracts were filtered and concentrated under reduced pressure to afford an oil, which was further dried on high vacuum, yielding 134.2 mg (93%) of the bromo-pyrazole benzyl carbamate ($MH^+$=381).

Step C

Treatment of the bromo-pyrazole benzyl carbamate compound from step B with n-butyllithium followed by the addition of methyl borate would convert the bromo-pyrazole benzyl carbamate to the corresponding boronic ester. Subsequent one-pot oxidation of the boronic ester with $H_2O_2$ aqueous solution would afford the hydroxy-pyrazole benzyl carbamate.

Step D

Treatment of the hydroxy-pyrazole benzyl carbamate from step C with hydrogen under the conditions of palladium (10% on activated carbon) in ethanol would afford the desired amino-hydroxy pyrazole.

Preparative Example 21 was added dropwise a 1.0 M sodium hydroxide aqueous solution (17.0 mL, 17.0 mmol). After addition, the mixture was heated to 75° C. (oil bath temperature) and continued for 18 h. The mixture was cooled to room temperature, treated with a 1.0 M hydrochloride aqueous solution until pH approximately being 2. The acidified mixture was extracted with 100 mL of $CH_2Cl_2$—$CH_3CN$ (1:1, v/v), 50 mL of $CH_2Cl_2$, and 50 mL of $CH_3CN$. The combined organic extracts were washed with brine (30 mL), dried over $Na_2SO_4$, and concentrated under reduced pressure to a solid, which was further dried on high vacuum, yielding 1.84 g (100%) of 3-methoxythiophene carboxylic acid ($MH^+$=159.0).

Step B

To a suspension of 3-methoxythiophene carboxylic acid (1.84 g, 11.61 mmol), from step A, in 60 mL of acetonitrile at room temperature was added bromotripyrrolidinophosphonium hexafluorophosphate (PyBrop, 5.40 g, 11.60 mmol), dimethyl amine (2.0 M in THF, 14.5 ml, 29.0 mmol) and diisopropylethyl amine (5.0 mL, 28.63 mmol) successively. After stirred for 1.5 day, the mixture was concentrated under reduced pressure to a yellow oil, which was purified by preparative TLC ($CH_2Cl_2$—MeOH=40:1). The silica was extracted with $CH_2Cl_2$ and methanol, the extracts were filtered and concentrated to an oil, which was further dried on high vacuum, yielding 4.16 g of N,N-dimethyl 3-methoxythiophene amide (contaminated by PyBrop impurity) ($MH^+$=186.0).

Step C

To a vigorously stirred solution of thiophene amide (4.16 g, prepared in step B) in 6 mL of concentrated sulfuric acid at −10° C. was added dropwise fuming nitric acid (0.6 mL, 14.28 mmol). After 1.5 h, the mixture was poured into 80 mL of a mixture of 1.0 M NaOH aqueous solution and ice (1:1, v/v). An additional 40 mL of $H_2O$ was used to facilitate the transfer. The yellow precipitates were collected by filtration, washed with $H_2O$ twice, and dried on high vacuum, to give

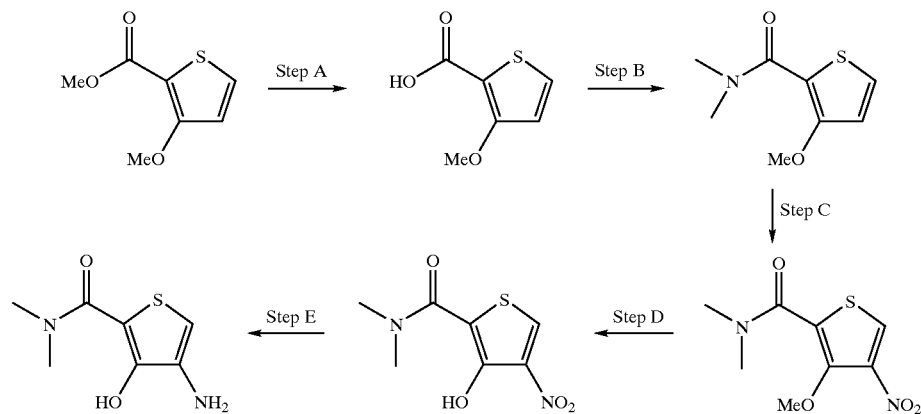

Step A

To a solution of methyl 3-methoxythiophene carboxylate (2.0 g, 11.6 mmol) in 20 mL of THF at room temperature 1.67 g of the nitro-thiophene product. The aqueous filtrates were extracted with $CH_2Cl_2$ (50 mL×3). The extracts were washed with a sat. $NaHCO_3$ aqueous solution (30 mL) and brine (30 mL), and dried with Na$_2$SO$_4$. Evaporation of solvent afforded a yellow oil, which was purified by preparative TLC (CH$_2$Cl$_2$—MeOH=50:1) to give an additional 0.144 g of the nitro-thiophene as a solid (1.81 g total, 68% over two steps, MH$^+$=231.0).

Step D

To a vigorously stirred solution of methoxy-nitrothiophene (900.0 mg, 3.91 mmol), obtained from step C, in 55 mL of anhydrous CH$_2$Cl$_2$ at −78° C. was added dropwise along the inside wall of the flask a 1.0 M solution of boron tribromide in CH$_2$Cl$_2$ during a 15 min period. The mixture was stirred for 4 h while the temperature of the cooling bath was increased slowly from −78° C. to −10° C., and poured into 100 mL of a mixture of ice and H$_2$O (~1:1, v/v). Additional 30 mL of H$_2$O and 30 mL of CH$_2$Cl$_2$ were used to rinse the flask. The combined mixture was stirred at room temperature over night, the two layers were separated, and the aqueous layer was extracted with CH$_2$Cl$_2$ (50 mL×3). The organic layers were combined, washed with a sat. NaHCO$_3$ aqueous solution (50 mL×2) and brine (50 mL×2), dried with Na$_2$SO$_4$, and concentrated to a yellow solid. The crude product was purified by flash column chromatography, eluting with hexanes, CH$_2$Cl$_2$-hexanes (1:1 and 2:1). Removal of solvents afforded a solid, which was further dried on high vacuum, giving 615.2 mg (73%) of the hydroxy-nitro-thiophene amide (MH$^+$=217.0).

Step E

To a nitrogen flushed solution of hydroxy-nitro-thiephene amide (610.0 mg, 2.82 mmol), prepared in step D, in 60 mL of ethanol was added palladium 15' hydroxide (20 wt % on activated carbon, wet with <=50% water, 610.0 mg). The suspension was degassed via house vacuum and refilled with hydrogen gas from a gas balloon. The mixture was first stirred at room temperature under a hydrogen atmosphere for 2 h, then heated to 70–80° C. and: continued for 20 h. Solid material was removed by filtration through a 1-in Celite pad, the filtration pad was washed with 100 mL of ethanol, and the combined filtrates were concentrated to a light yellow solid. The crude product was treated with a mixture of CH$_2$Cl$_2$—MeOH (~1:1, v/v), off-white solids precipitated out and collected by filtration as the first crop of the product (75.4 mg). The filtrate was concentrated to a solid residue, which was purified by flash column chromatography, eluting with CH$_2$Cl$_2$-EtOH (10:1 and 2:1). Removal of solvents afforded 226.8 mg of the amino-hydroxy-thiophene amide as a solid (302.2 mg total, 58%, MH$^+$=187.0).

Preparative Example 22

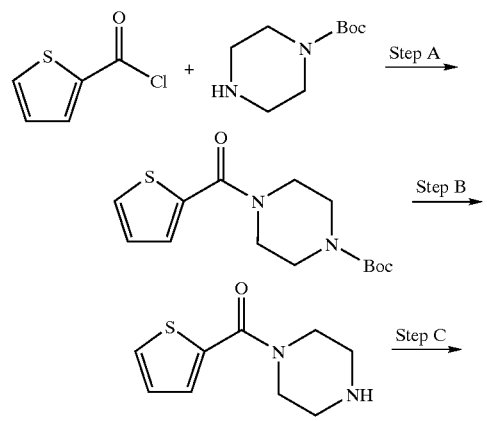

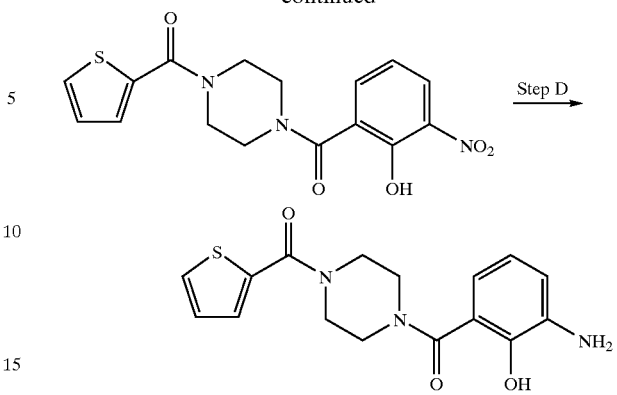

Step A

2-Thiophenecarbonyl chloride (2.0 mL, 18.7 mmol) was dissolved in 100 mL dichloromethane. After addition of diisopropylethylamine (40.1 mL, 23.4 mmol) and Boc-piperazine (3.66 g, 19.7 mmol), the mixture was stirred for 4 h at room temperature. The resulting cloudy mixture was put into water (500 mL) and acidified with 3N HCl to pH-1. Extraction with dichloromethane (2×100 mL) and drying over sodium sulfate resulted in sufficiently pure product that was used in the next step without any further purification.

$^1$H NMR (300 MHz, d$_6$-DMSO) 1.60 (s, 9H), 3.29 (dd, 4H), 3.69 (dd, 4H), 7.23 (dd, 1H), 7.49 (d, 1H), 7.79 (d, 1H).

Step B

The crude material from Step A was dissolved in trifluoroacetic acid/dichloromethane (75 mL, 4/1). After stirring for 2 h, the reaction mixture was put into 1N sodium hydroxide (400 mL). Extraction with dichloromethane (2×100 mL) and drying over sodium sulfate resulted in sufficiently pure product that was used in Step C without any further purification.

$^1$H NMR (300 MHz, d$_6$-DMSO) 2.81 (dd, 4H), 3.63 (dd, 4H), 7.21 (dd, 1H), 7.46 (d, 1H), 7.82 (d, 1H).

Step C

The crude material (3.50 g, 17.8 mmol) from Step B was dissolved in dichloromethane (100 mL). After addition of diisopropylethylamine (18.7 mL, 107 mmol), 3-nitrosalicylic acid (3.3 g, 18.0 mmol), and PyBrOP (10.4 g, 22.3 mmol), the resulting yellow mixture was stirred over night at room temperature before being put into 1N sodium hydroxide (200 mL). Extraction with dichloromethane (2×200 mL) removed all PyBrOP by-products. The aqueous phase was acidified with 3N HCl and subsequently extracted with dichloromethane (3×100 mL). The combined organic phases of the acidic extraction were dried over sodium sulfate, concentrated, and finally purified by column chromatography (dichloromethane/methanol=10/1) to yield the desired product (2.31 g, 34% over 3 steps).

$^1$H NMR (300 MHz, d$_6$-DMSO) 3.30–3.90 (m, 8H), 7.10–8.20 (m, double signals due to E/Z-isomers, 6H), 10.82 (s, 1H).

Step D

The nitro-compound (2.3 g, 6.4 mmol) from Step C was dissolved in methanol (50 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=10/1) to yield the desired product (1.78 g, 84%).

$^1$H NMR (300 MHz, d$_6$-DMSO) 3.30–3.90 (m, 8H), 7.22 (m, 2H), 7.55 (d, 1H), 7.71. (d, 1H), 7.88 (d, 1H). 8.15 (d, 1H), 10.85 (bs, 1H).

Preparative Example 23

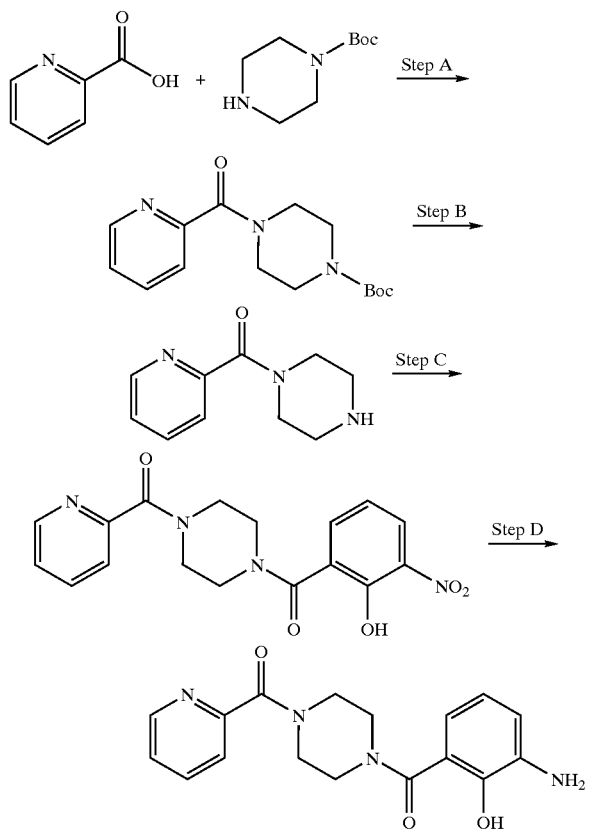

Step A

Picolinic acid (3.0 g, 24.3 mmol) was suspended in SOCl$_2$ (15 mL). After addition of dimethylformamide (5 drops), the reaction mixture was stirred for 4 hours. During this period the color changed from white to green to brown to finally dark wine-red and all solid went into solution. Evaporation of the solvent yielded the corresponding acid chloride as HCl-salt. Without any further purification, the solid was suspended in 120 mL dichloromethane. After addition of diisopropylethylamine (12.7 mL, 73 mmol) and Boc-piparazine (4.8 g, 25.5 mmol), the reaction was stirred over night at room temperature. The resulting cloudy mixture was put into water (500 mL) and extracted with dichloromethane (2×100 mL). Drying over sodium sulfate resulted in sufficiently pure product that was used in Step B without any further purification.

$^1$H NMR (300 MHz, d$_6$-DMSO) 1.63 (s, 9H), 3.21 (dd, 4H), 3.61 (dd, 4H), 7.57 (dd, 1H), 7.63 (d, 1H), 7.98 (dd, 1H), 8.70 (d, 1H).

Step B

The crude material from Step A was dissolved in trifluoroacetic acid/dichloromethane (75 mL, 4/1). After stirring for 2 days, the reaction mixture was put into 1N sodium hydroxide (400 mL). Extraction with dichloromethane (2×100 mL) and drying over sodium sulfate resulted in sufficiently pure product that was used in Step C without any further purification.

$^1$HNMR (300 MHz, d$_6$-DMSO)2.77 (dd, 2H), 2.83 (dd; 1H), 3.38 (dd, 2H), 3.64 (dd, 1H), 7.58 (dd, 1H), 7.62 (d, 1H), 8.00 (dd, 1H), 8.67 (d, 1H).

Step C

The crude material (1.35 g, 7.06 mmol) from Step B was dissolved in dichloromethane (50 mL). After addition of diisopropylethylamine (3.7 mL, 21.2 mmol), 3-nitrosalicylic acid (1.36 g, 7.41 mmol), and PyBrOP (3.62 g, 7.77 mmol), the resulting yellow mixture was stirred over night at room temperature before being put into 1N sodium hydroxide (300 mL). Extraction with dichloromethane (2×100 mL) removed any PyBrOP products. The aqueous phase was acidified with 3N HCl. Careful adjustment of the pH with saturated sodium carbonate solution to almost neutral crushed the desired compound out of solution. The aqueous phase was subsequently extracted with dichloromethane (3×1 00 mL). The combined organic layers of the neutral extraction were dried over sodium sulfate, concentrated, and finally purified by column chromatography (dichloromethane/methanol=20/1) to yield the desired product (1.35 g, 16% over 3 steps).

$^1$H NMR (300 MHz, d$_6$-DMSO) 3.30–3.95 (m, 8H), 7.22 (m, 1H). 7.61 (m, 1H), 7.73 (d, 2H), 8.03 (m, 1H), 8.17 (m, 1H), 8.69 (m, 1H), 10.82 (s, 1H).

Step D

The nitro-compound (1.35 g, 3.79 mmol) from Step C was dissolved in methanol (60 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=20/1) to yield the desired product (1.10 g, 89%).

$^1$H NMR (300 MHz, d$_6$-DMSO) 3.50–3.85 (m, 8H), 6.47 (dd 1H), 6.74 (m, 2H), 7.59 (dd, 1H), 7.71 (d, 1H), 8.04 (dd. 1H), 8.68 (d, 1H).

Preparative Example 24

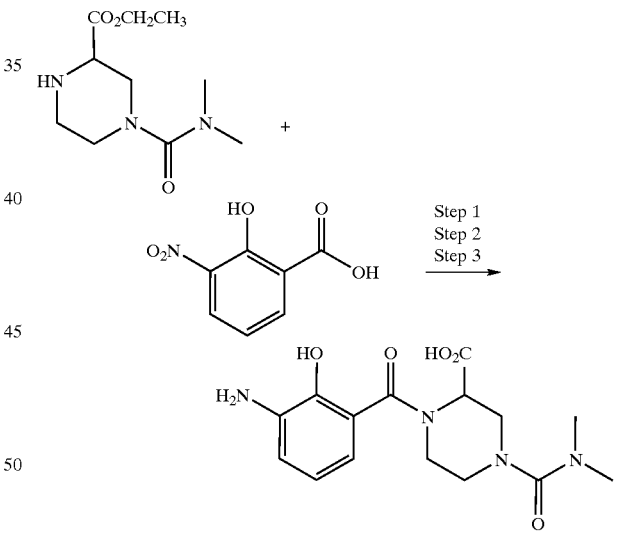

Step 1

3-Nitrosalicylic acid (3.61 g, 0.0197 g), DCC (2.03 g, 0.0099 mol) and ethyl acetate (130 mL) were combined in a round bottom flask and stirred for 15 min. 4-Dimethylcarbamoyl-piperazine-2-carboxylic acid ethyl ester (4.51 g, 0.0197 g) was added, and the reaction was stirred for 72 hours. The reaction mixture was concentrated then dissolved in dichloromethane. The organic phase was washed once with 0.1N sodium hydroxide. The aqueous phase was back extracted once with dichloromethane. The aqueous phase was acidified and wash three times with ethyl acetate. The aqueous phase was concentrated and purified by column chromatography (5% methanol/DCM).

MS: calculated: 394.15, found: 395.0

$^1$H NMR (300 MHz, CDCl$_3$) 1.32 (t, 3H), 2.86 (m, 7H), 3.15 (m, 1H), 3.51 (m, 4H), 4.24 (m, 3H), 7.15 (m, 1H), 7.66 (m, 1H), 8.20 (m, 1H), 10.86 (bs, 1H).

Step 2

4-Dimethylcarbamoyl-1-(2-hydroxy-3-nitro-benzoyl) piperazine-2-carboxylic acid ethyl ester (0.80 g, 0.002 mol) and methanol (50 mL) were combined in a round bottom flask. The system was purged with argon. To the solution was added 5% palladium on carbon (~100 mg). The flask was purged with hydrogen and stirred overnight. The reaction was filtered through a pad of celite and washed with methanol. The material was concentrated then purified by column chromatography (6% methanol/DCM). Isolated product (0.74 g, 0.002 mol, 100%).

MS: calculated: 364.17, found: 365.1

$^1$H NMR (300 MHz, CDCl$_3$) 1.27 (t, 3H), 2.85 (m, 8H), 3.18 (1H), 3.45 (m, 3H), 4.19 (m, 3H), 3.90 (m, 3H)

Step 3

1-(3-Amino-2-hydroxy-benzoyl)$_4$-dimethylcarbamoyl-piperazine-2-carboxylic acid ethyl ester (0.74 g, 0.002 mol) was suspended in a solution of dioxane (10 mL) and water (10 mL). Lithium hydroxide (0.26 g, 0.0061 mol) was added and the mixture stirred for two hours. The solution was acidified to pH=6 with 3N HCl then extracted with butanol. The extracts were combined, dried over sodium sulfate and concentrated.

MS: calculated: 336.14, found: 337.1

$^1$H NMR (300 MHz, CD$_3$OD) 2.86 (m, 7H), 3.23 (m, 3H), 3.54 (m, 3H), 6.92 (m, 2H), 7.23 (m, 1H).

Preparative Example 25

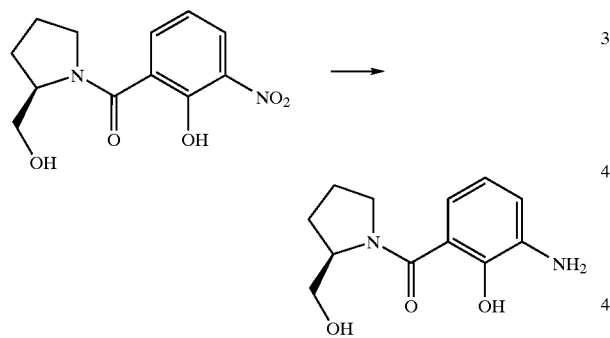

The product from Preparative Example 1 was stirred with 10% Pd/C under a hydrogen gas atmosphere overnight. The reaction mixture was filtered through celite, the filtrate concentrated in vacuo, and the resulting residue purified by column chromatography (silica gel, 4% MeOH/CH$_2$Cl$_2$ saturated with NH$_4$OH) to give the product (129 mg, 43%, MH$^+$=237).

Preparative Example 26

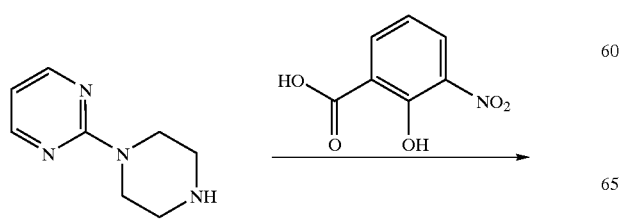

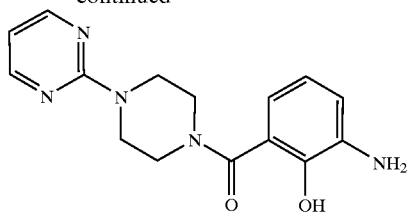

In essentially the same manner as described in Preparative Example 25, the amine product above was obtained; (50% yield, MH$^+$=300.1).

Preparative Example 27

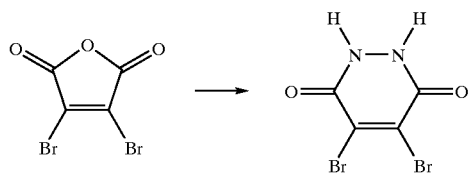

The product is prepared according to the literature procedure (Zh. Obshch. Khim.; 24; 1954; 1216, 1220; engl. Ausg. S. 1205, 1207).

Preparative Examples 28–31

Following the procedure in Preparative Example 27, using the indicated commercially available hydrazines shown in the table below, the following cyclic dibromo hydrazide products could be prepared.

| Prep Ex. | Hydrazine | Product |
|---|---|---|
| 28 | H$_2$N—NH$_2$ | (cyclic dibromo hydrazide, NH—NH) |
| 29 | MeHN—NHMe | (cyclic dibromo hydrazide, NMe—NMe) |

-continued

| Prep Ex. | Hydrazine | Product |
|---|---|---|
| 30 | H₂N-NH-Et | ethyl dibromopyridazinedione |
| 31 | cyclohexyl-NH-NH₂ | cyclohexyl dibromopyridazinedione |

Preparative Example 32

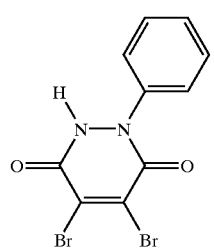

The product is prepared according to the literature procedure (Farmaco Ed. Sci. IT; 32; 1977; 173–179).

Preparative Example 33

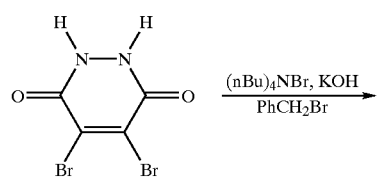

Following the procedure described in the literature (J. Heterocycl. Chem.; EN; 34; 4; 1997; 1307–1314) using benzyl bromide instead of 1-chloro-propan-2-one, the product could be obtained.

Preparative Example 34

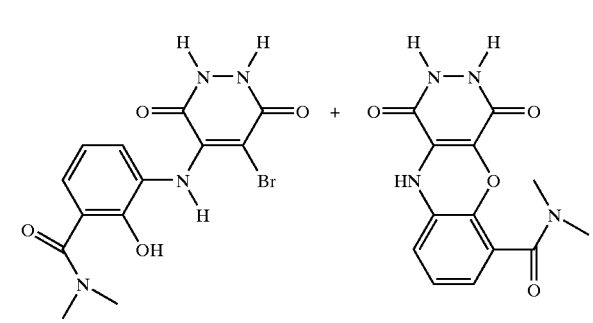

Following a similar procedure as that outlined in the literature (Farmaco Ed. Sci. IT; 32; 1977; 173–179) using the product from Preparative Example 3 instead of 2-methylamino-benzenethiol, the product would be obtained.

Preparative Examples 35–133

Following the procedure set forth in Preparative Example 34 using the amine and dibromo intermediates from the Preparative Examples indicated, the products in the table below would be obtained.

| Ex. | (Prep Ex) Amine | (Prep Ex) Dibromo | Product |
|---|---|---|---|
| 35 | 5 | 27 | 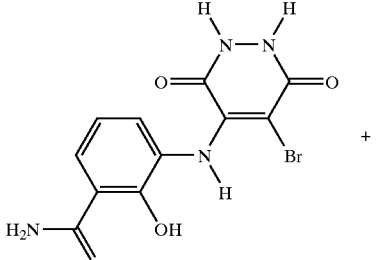 |
| 36 | 7 | 27 | 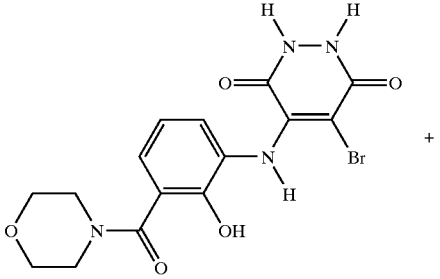 |
| 37 | 6 | 27 | 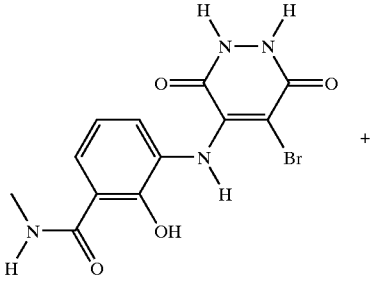 |

-continued

| Ex. | (Prep Ex) Amine | (Prep Ex) Dibromo | Product |
|---|---|---|---|
| 38 | 23 | 27 | |
| 39 | 24 | 27 | |

-continued

| Ex. | (Prep Ex) Amine | (Prep Ex) Dibromo | Product |
|---|---|---|---|
| | | | (structure: tricyclic pyridazine-dione fused with oxazine and quinoline, bearing a piperazine-2-carboxylic acid substituent with N-dimethylcarbamoyl group) |
| 40 | 15 | 27 | (structure: pyrimidine with dimethylcarboxamide, OH, NH-linked to bromo-pyridazinedione) + (structure: tricyclic pyrimido-oxazino-pyridazinedione with N,N-dimethylcarboxamide) |
| 41 | 11 | 27 | (structure: cyano, hydroxy, N,N-dimethylcarboxamide-substituted benzene, NH-linked to bromo-pyridazinedione) + |

-continued
| Ex. | (Prep Ex) Amine | (Prep Ex) Dibromo | Product |
|---|---|---|---|
| | | | 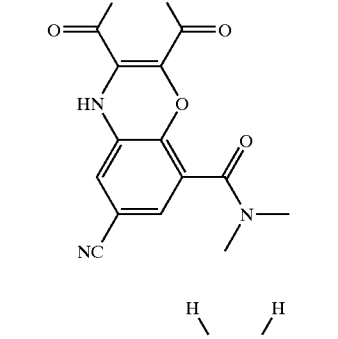 |
| 42 | 21 | 27 | 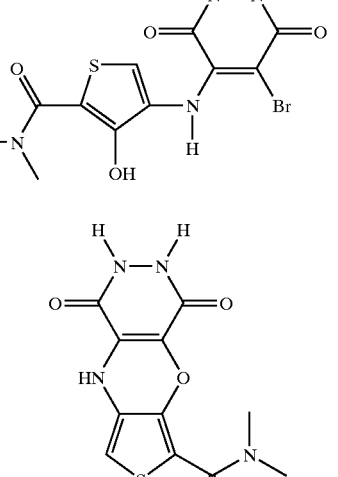 |
| 43 | 14 | 27 | 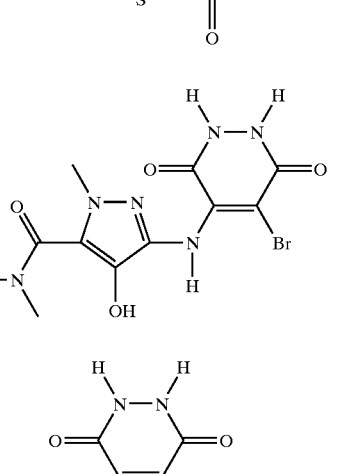 |

-continued

| Ex. | (Prep Ex) Amine | (Prep Ex) Dibromo | Product |
|---|---|---|---|
| 44 | 12 | 27 | (structure) + (structure) |
| 45 | 19 | 27 | (structure) |
| 46 | 20 | 27 | (structure) |
| 47 | 18 | 27 | (structure) |

-continued
| Ex. | (Prep Ex) Amine | (Prep Ex) Dibromo | Product |
|---|---|---|---|
| 48 | 16 | 27 | 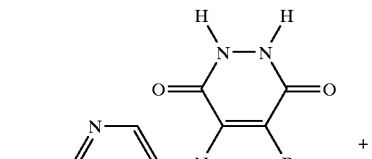 + |
| 49 | 3 | 28 | 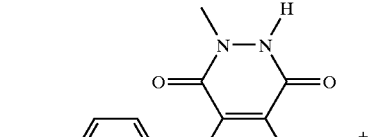 + |
| 50 | 5 | 28 | 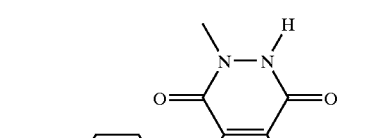 + |

| Ex. | (Prep Ex) Amine | (Prep Ex) Dibromo | Product |
|---|---|---|---|
| 51 | 4 | 28 | |
| 52 | 8 | 28 | |

-continued
| Ex. | (Prep Ex) Amine | (Prep Ex) Dibromo | Product |
|---|---|---|---|
| 53 | 7 | 28 | 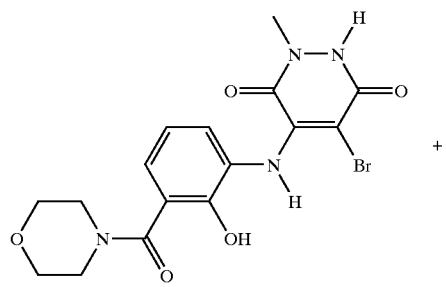 +<br>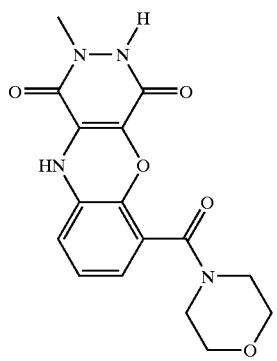 |
| 54 | 9 | 28 | 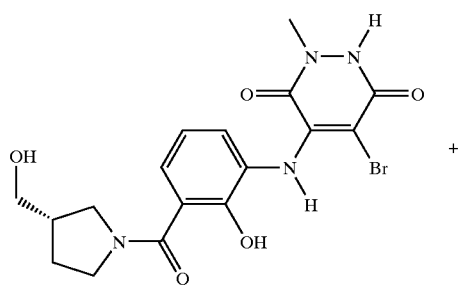 +<br>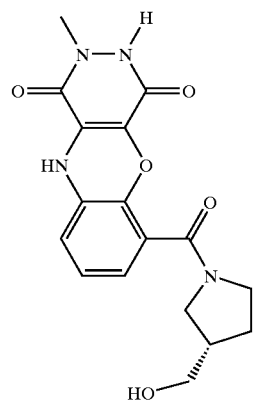 |

-continued
| Ex. | (Prep Ex) Amine | (Prep Ex) Dibromo | Product |
|---|---|---|---|
| 55 | 6 | 28 | 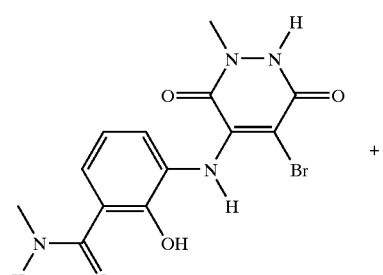 |
| 56 | 26 | 28 | 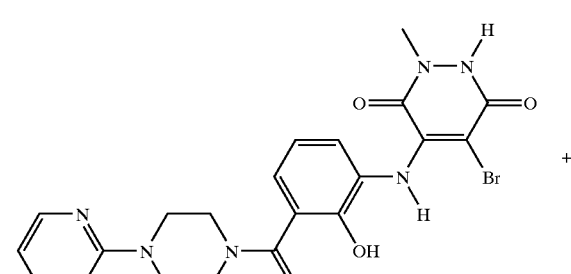 |

-continued
| Ex. | (Prep Ex) Amine | (Prep Ex) Dibromo | Product |
|---|---|---|---|
| 57 | 23 | 28 | 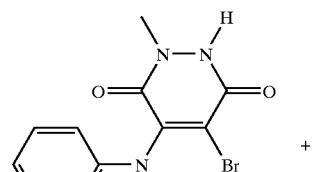 + 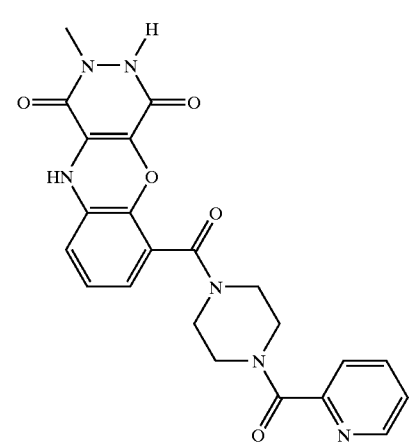 |
| 58 | 22 | 28 | 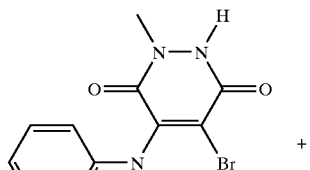 + 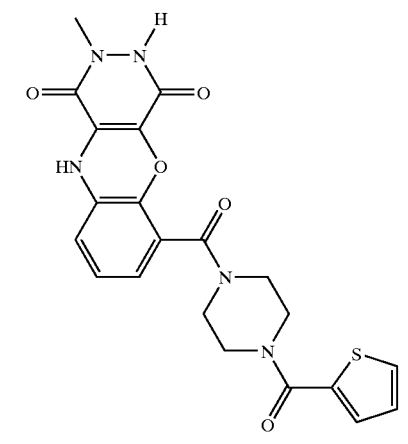 |

-continued
| Ex. | (Prep Ex) Amine | (Prep Ex) Dibromo | Product |
|---|---|---|---|
| 59 | 24 | 28 | 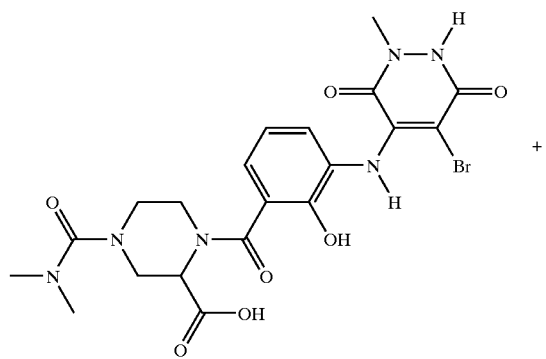 + 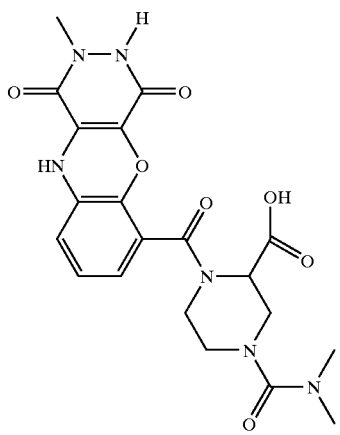 |
| 60 | 15 | 28 | 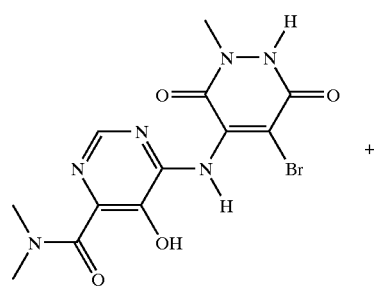 + 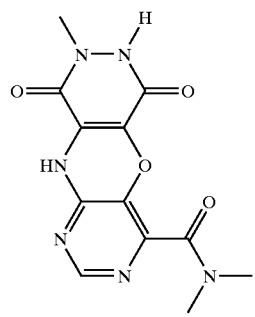 |

-continued
| Ex. | (Prep Ex) Amine | (Prep Ex) Dibromo | Product |
|---|---|---|---|
| 61 | 16 | 28 | 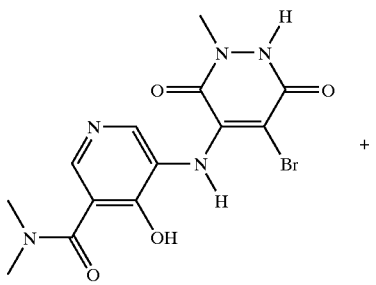 + |
| 62 | 17 | 28 | 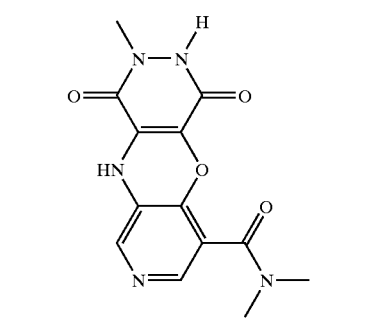 + |
| 63 | 11 | 28 | 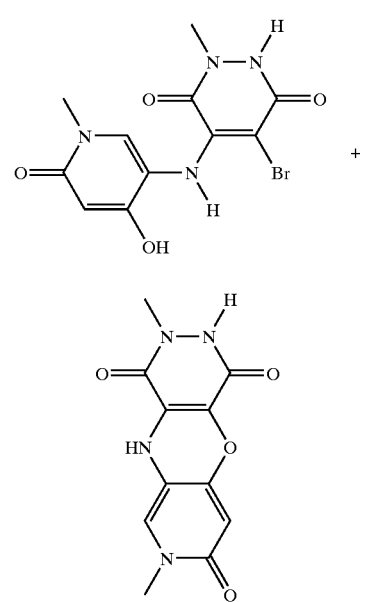 + |

| Ex. | (Prep Ex) Amine | (Prep Ex) Dibromo | Product |
|---|---|---|---|
|  |  |  | 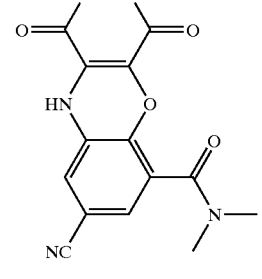 |
| 64 | 13 | 28 | 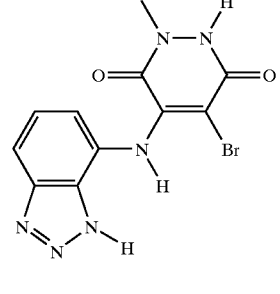 |
| 65 | 21 | 28 | 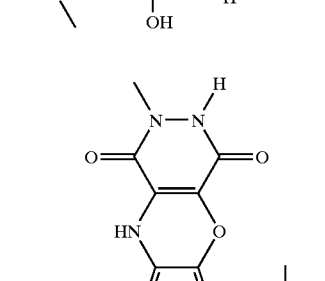 + |
| 66 | 14 | 28 | 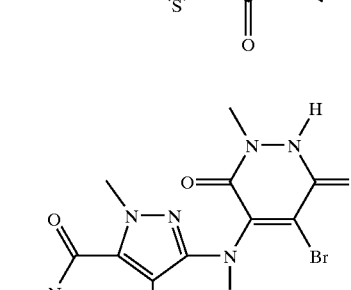 + |

-continued

| Ex. | (Prep Ex) Amine | (Prep Ex) Dibromo | Product |
|---|---|---|---|
| 67 | 12 | 28 | |
| 68 | 19 | 28 | |
| 69 | 14 | 28 | |

-continued
| Ex. | (Prep Ex) Amine | (Prep Ex) Dibromo | Product |
|---|---|---|---|
| 70 | 18 | 28 | 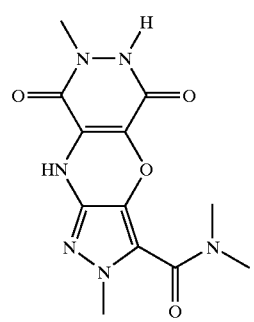 |
| 71 | 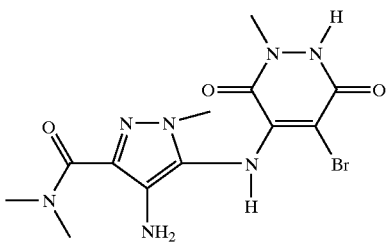 | 28 | 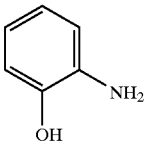 + 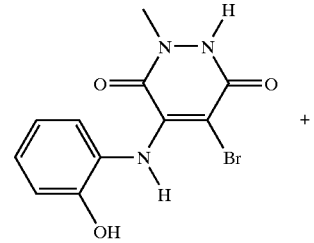 |
| 72 | 3 | 28 | 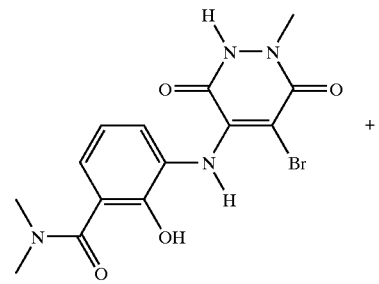 + |

-continued

| Ex. | (Prep Ex) Amine | (Prep Ex) Dibromo | Product |
|---|---|---|---|
| 73 | 5 | 28 | |
| 74 | 4 | 28 | |

-continued
| Ex. | (Prep Ex) Amine | (Prep Ex) Dibromo | Product |
|---|---|---|---|
| 75 | 8 | 28 | 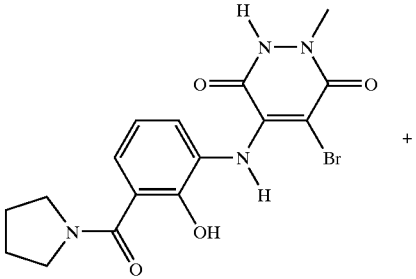 + |
| 76 | 7 | 28 | 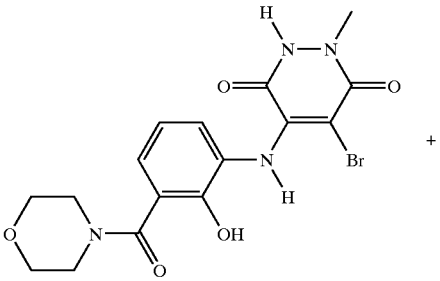 + |

| Ex. | (Prep Ex) Amine | (Prep Ex) Dibromo | Product |
|---|---|---|---|
| 77 | 9 | 28 | 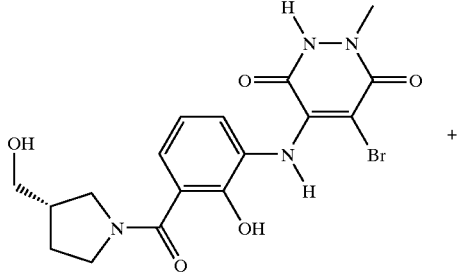 |
| 78 | 6 | 28 | 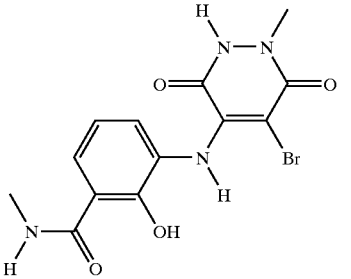 |

-continued
| Ex. | (Prep Ex) Amine | (Prep Ex) Dibromo | Product |
|---|---|---|---|
| 79 | 26 | 28 | 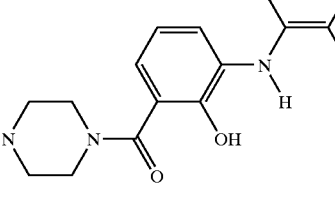 + |
| 80 | 23 | 28 | 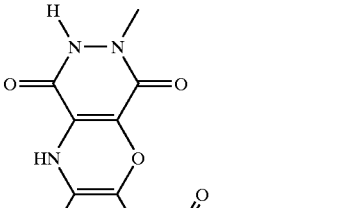 + |

-continued
| Ex. | (Prep Ex) Amine | (Prep Ex) Dibromo | Product |
|---|---|---|---|
| 81 | 22 | 28 | 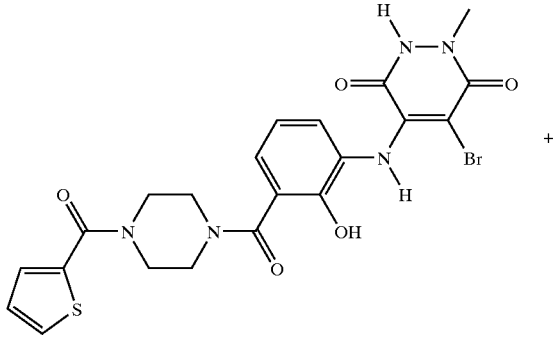 + |
| 82 | 24 | 28 | 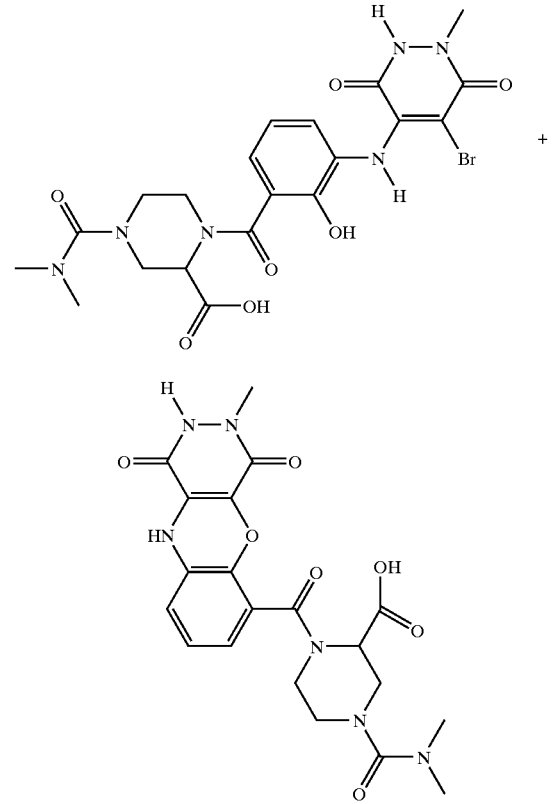 + |

-continued
| Ex. | (Prep Ex) Amine | (Prep Ex) Dibromo | Product |
|---|---|---|---|
| 83 | 15 | 28 | 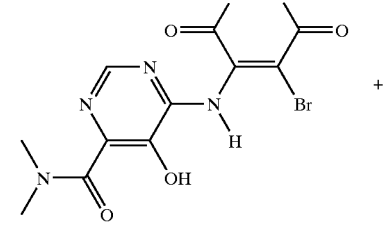 + |
| 84 | 16 | 28 | 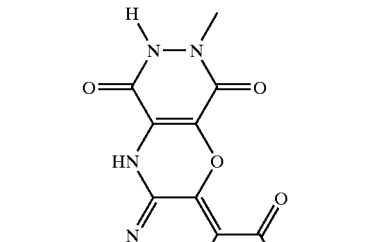 + |
| 85 | 17 | 28 | 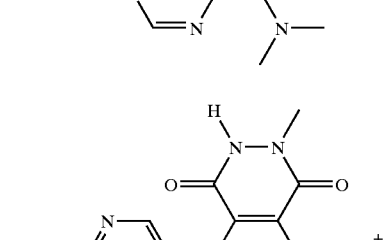 + |

-continued
| Ex. | (Prep Ex) Amine | (Prep Ex) Dibromo | Product |
|---|---|---|---|
| | | | 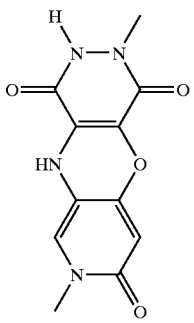 |
| 86 | 11 | 28 | 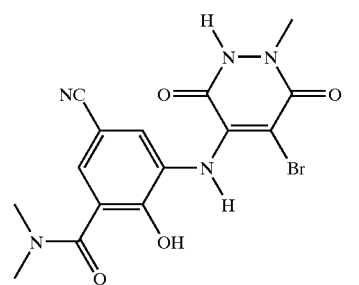 + |
| 87 | 13 | 28 | 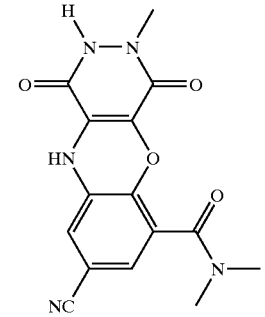 |
| 88 | 21 | 28 | 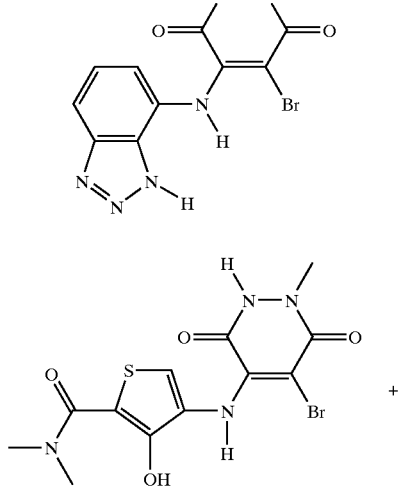 + |

-continued
| Ex. | (Prep Ex) Amine | (Prep Ex) Dibromo | Product |
|---|---|---|---|
| 89 | 14 | 28 | 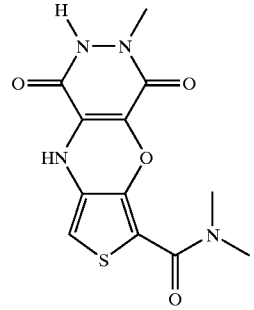 + 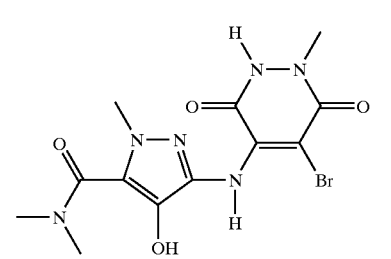 |
| 90 | 12 | 28 | 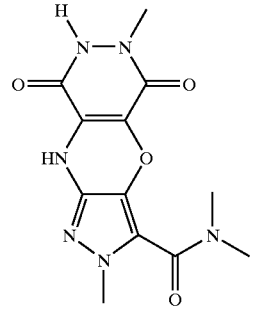 + 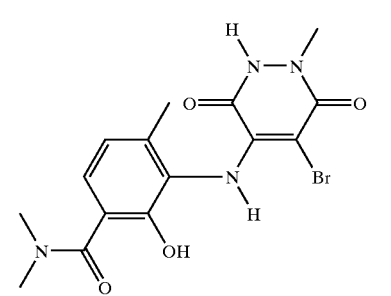 |

-continued
| Ex. | (Prep Ex) Amine | (Prep Ex) Dibromo | Product |
|---|---|---|---|
| 91 | 19 | 28 | 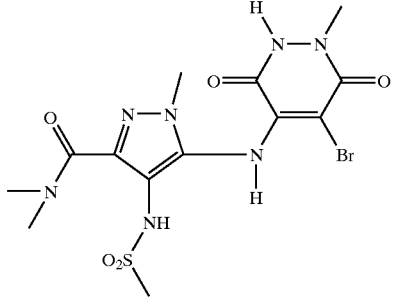 |
| 92 | 14 | 28 | 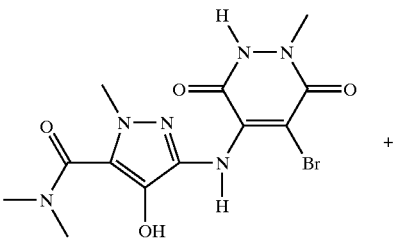 + |
| 93 | 18 | 28 | 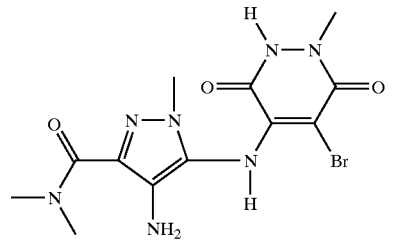 |
| 94 | 3 | 29 | 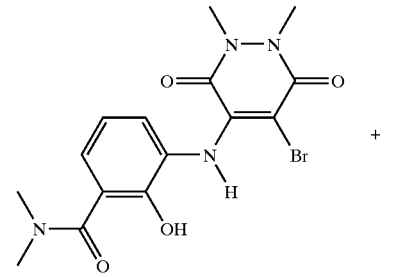 + |

-continued

| Ex. | (Prep Ex) Amine | (Prep Ex) Dibromo | Product |
|---|---|---|---|
| 95 | 5 | 29 | |
| 96 | 4 | 29 | |

-continued
| Ex. | (Prep Ex) Amine | (Prep Ex) Dibromo | Product |
|---|---|---|---|
| 97 | 8 | 29 | 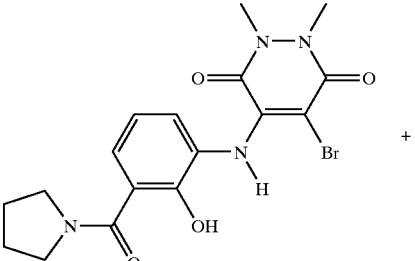 + |
| 98 | 7 | 29 | 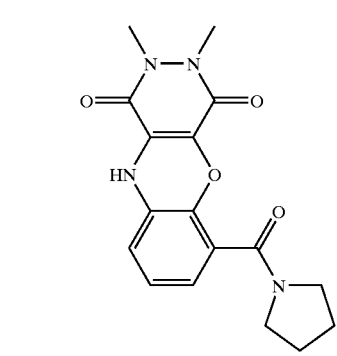 + |
| 99 | 9 | 29 | 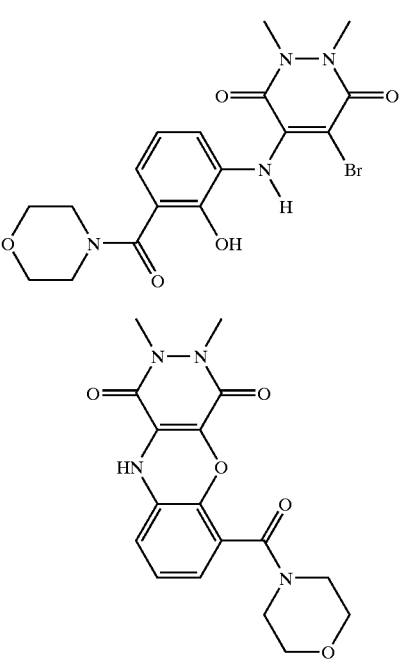 + |

|  | (Prep Ex) | (Prep Ex) |  |
| --- | --- | --- | --- |
| Ex. | Amine | Dibromo | Product |
|  |  |  | 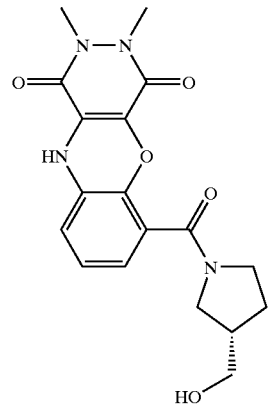 |
| 100 | 6 | 29 | 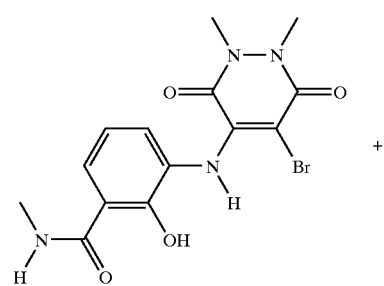 + 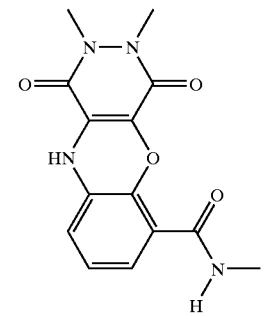 |
| 101 | 26 | 29 | 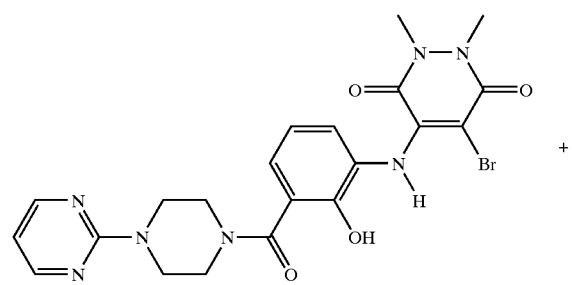 + |

-continued
| Ex. | (Prep Ex) Amine | (Prep Ex) Dibromo | Product |
|---|---|---|---|
| 102 | 23 | 29 | 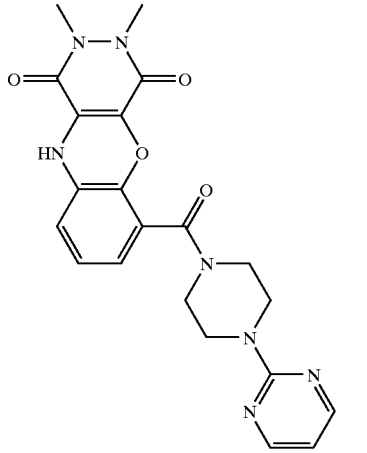 + |
| 103 | 22 | 29 | 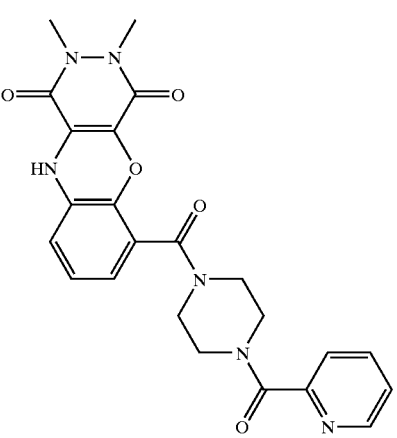 + |

-continued
| Ex. | (Prep Ex) Amine | (Prep Ex) Dibromo | Product |
| --- | --- | --- | --- |
| 104 | 24 | 29 | 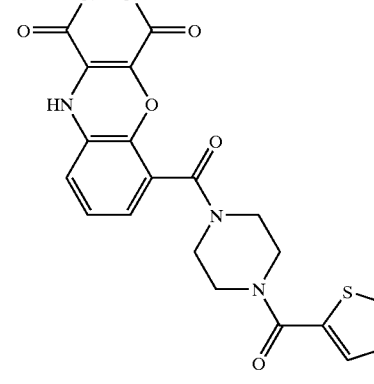 |
| 105 | 15 | 29 | 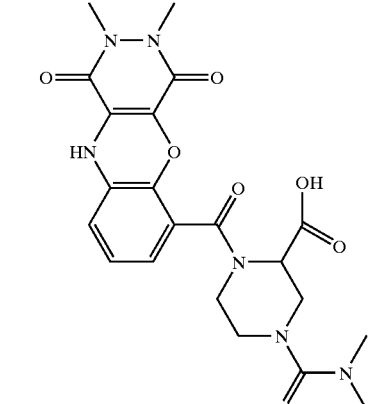 |

| Ex. | (Prep Ex) Amine | (Prep Ex) Dibromo | Product |
|---|---|---|---|
|  |  |  | 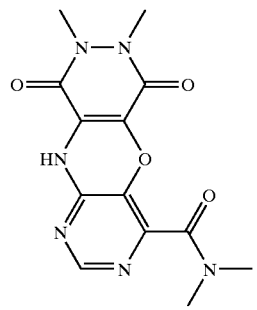 |
| 106 | 16 | 29 |  |
| 107 | 17 | 29 | 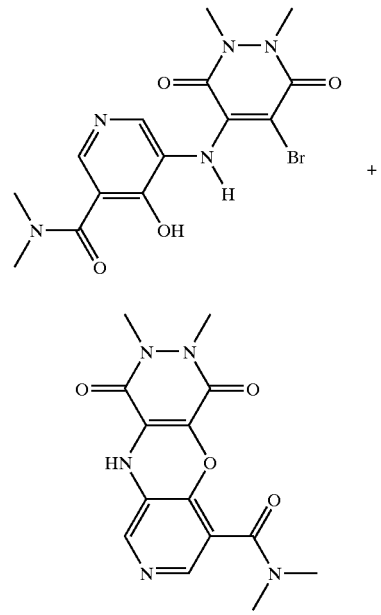 |

-continued
| Ex. | (Prep Ex) Amine | (Prep Ex) Dibromo | Product |
|---|---|---|---|
| 108 | 11 | 29 | 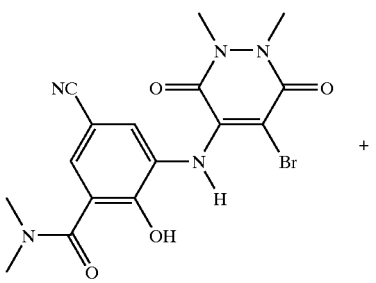 |
| 109 | 13 | 29 | 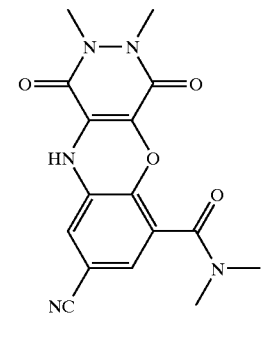 |
| 110 | 21 | 29 | 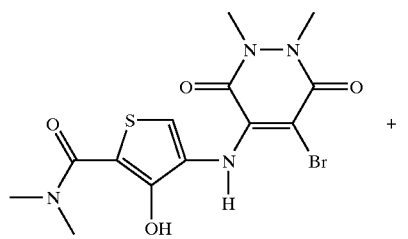 |

| Ex. | (Prep Ex) Amine | (Prep Ex) Dibromo | Product |
|---|---|---|---|
| 111 | 14 | 29 | 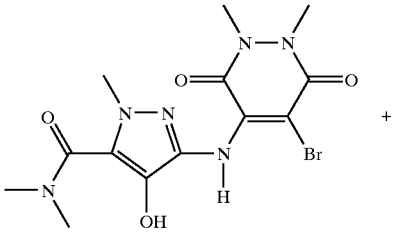 + 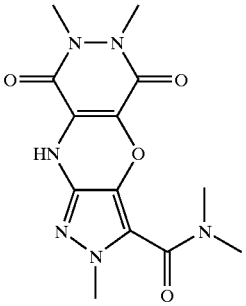 |
| 112 | 12 | 29 | 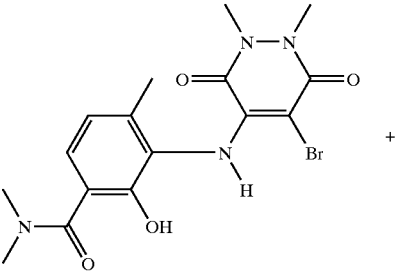 + 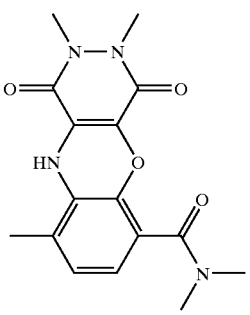 |
| 113 | 19 | 29 | 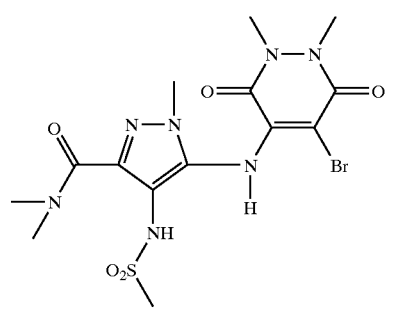 |

-continued
| Ex. | (Prep Ex) Amine | (Prep Ex) Dibromo | Product |
|---|---|---|---|
| 114 | 14 | 29 | 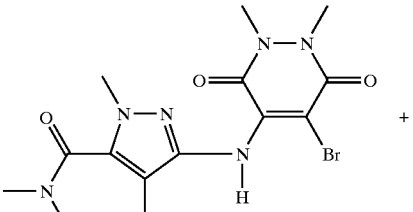 |
| 115 | 18 | 29 | 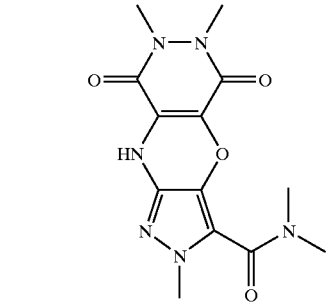 |
| 116 | 3 | 30 | 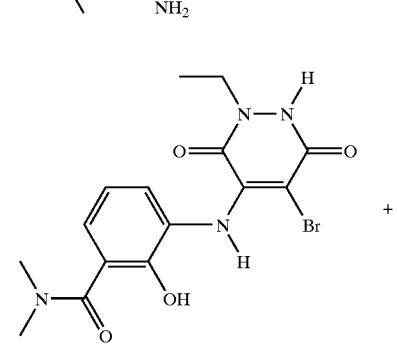 |

-continued
| Ex. | (Prep Ex) Amine | (Prep Ex) Dibromo | Product |
|---|---|---|---|
| 117 | 7 | 30 | 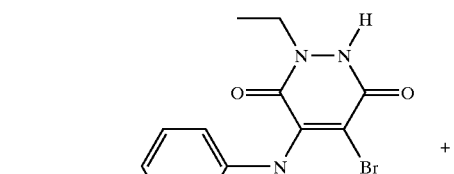 + 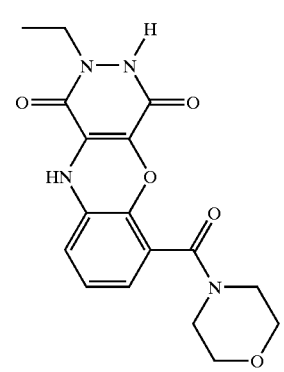 |
| 118 | 6 | 30 | 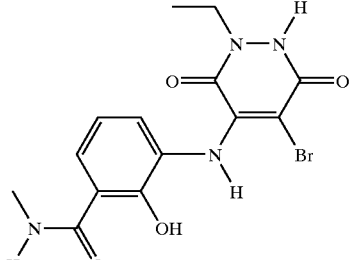 + 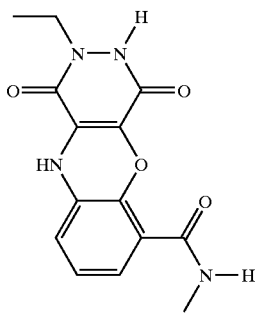 |
| 119 | 11 | 30 | 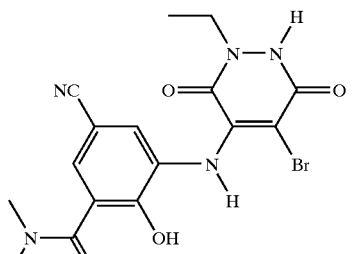 + 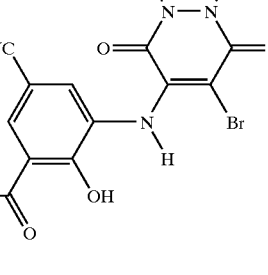 |

-continued
| Ex. | (Prep Ex) Amine | (Prep Ex) Dibromo | Product |
|---|---|---|---|
|  |  |  | 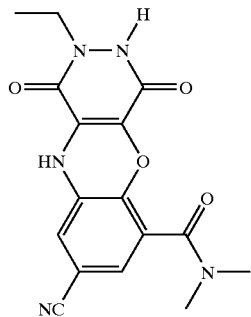 |
| 120 | 16 | 30 | 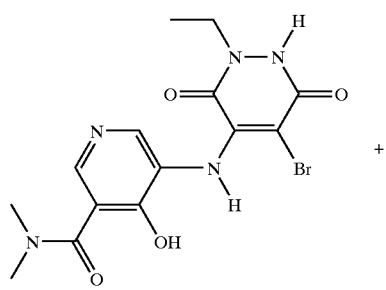 + |
|  |  |  | 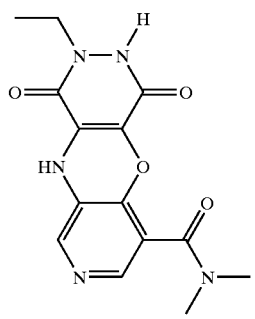 |
| 121 | 3 | 31 | 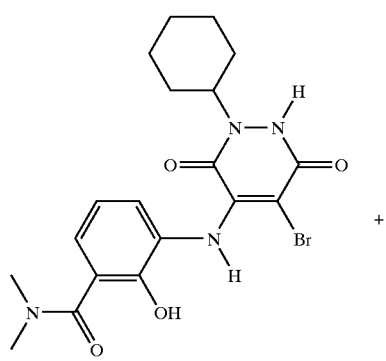 + |

-continued
| Ex. | (Prep Ex) Amine | (Prep Ex) Dibromo | Product |
|---|---|---|---|
| 122 | 7 | 31 | 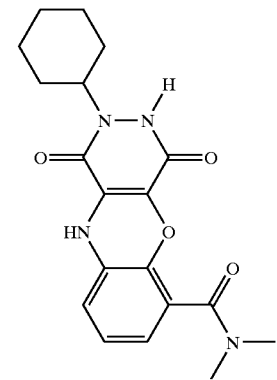 + 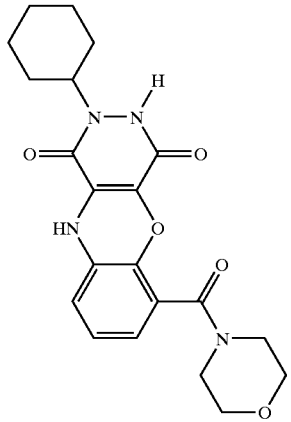 |
| 123 | 6 | 31 | 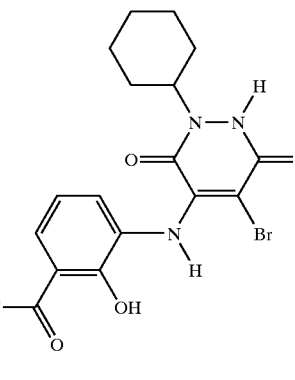 + |

-continued
| Ex. | (Prep Ex) Amine | (Prep Ex) Dibromo | Product |
|---|---|---|---|
| 124 | 11 | 31 | 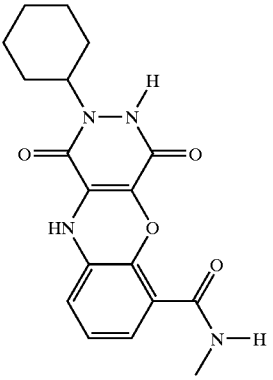 + 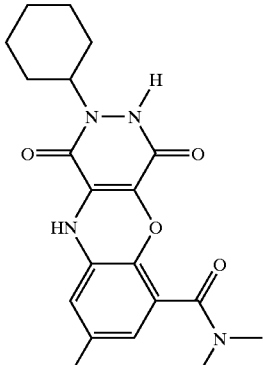 |
| 125 | 16 | 31 | 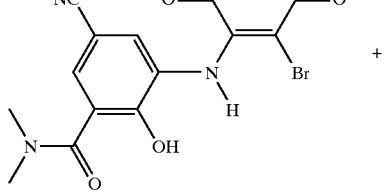 + |

-continued
| Ex. | (Prep Ex) Amine | (Prep Ex) Dibromo | Product |
|---|---|---|---|
| 126 | 3 | 32 | 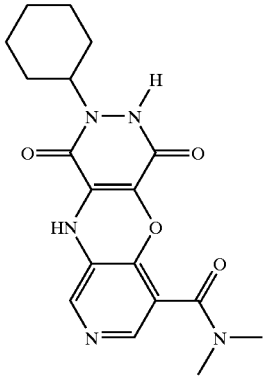 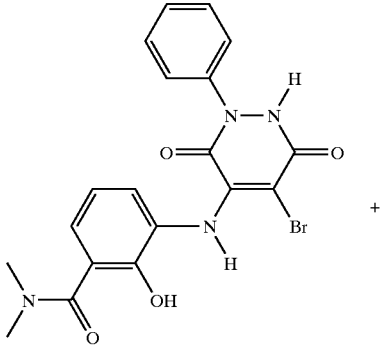 + |
| 127 | 7 | 32 | 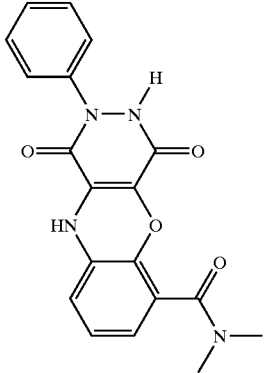 + |

-continued
| Ex. | (Prep Ex) Amine | (Prep Ex) Dibromo | Product |
|---|---|---|---|
| 128 | 6 | 32 | 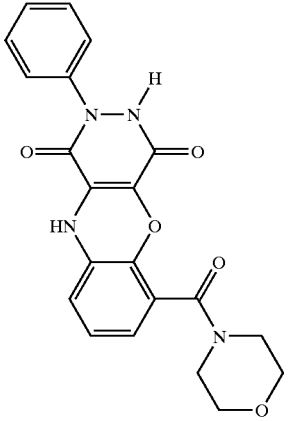 + |
| 129 | 11 | 32 | 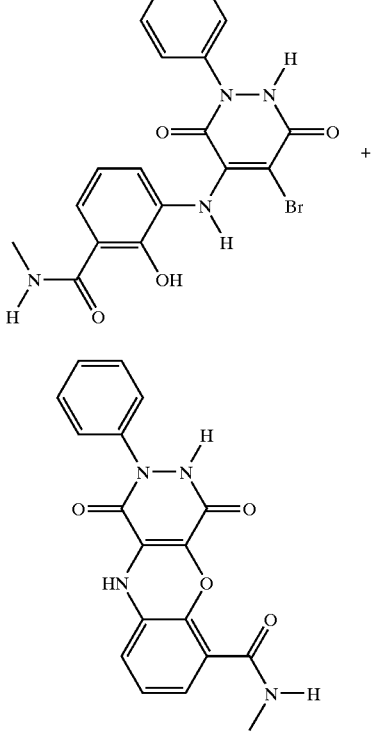 + |

-continued
| Ex. | (Prep Ex) Amine | (Prep Ex) Dibromo | Product |
|---|---|---|---|
|  |  |  | 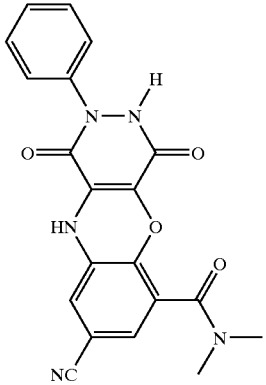 |
| 130 | 16 | 32 | 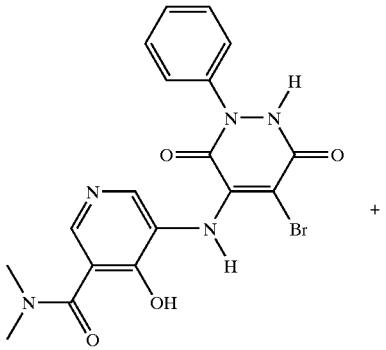 + |
| 131 | 3 | 33 | 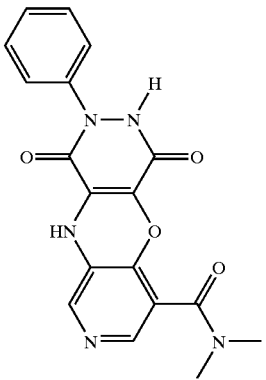 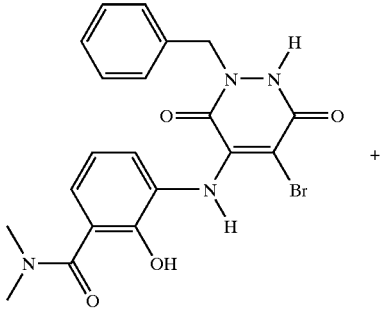 + |

| Ex. | (Prep Ex) Amine | (Prep Ex) Dibromo | Product |
|---|---|---|---|
| | | | *[structure: benzyl-pyridazinedione fused via O and NH to benzene ring bearing N,N-dimethylcarboxamide]* |
| 132 | 7 | 33 | *[structure: benzyl-pyridazinedione with Br, linked via NH to hydroxy-phenyl bearing morpholine carboxamide]* + *[structure: benzyl-pyridazinedione fused via O and NH to benzene ring bearing morpholine carboxamide]* |
| 133 | 6 | 33 | *[structure: benzyl-pyridazinedione with Br, linked via NH to hydroxy-phenyl bearing N-methylcarboxamide]* + |

-continued
| Ex. | (Prep Ex) Amine | (Prep Ex) Dibromo | Product |
|---|---|---|---|
|  |  |  | 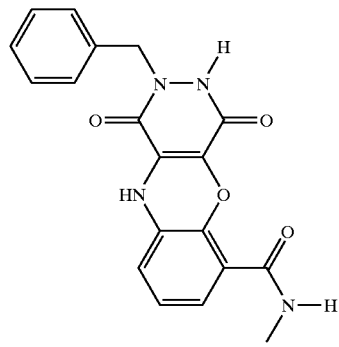 |
| 133.1 | 11 | 33 | 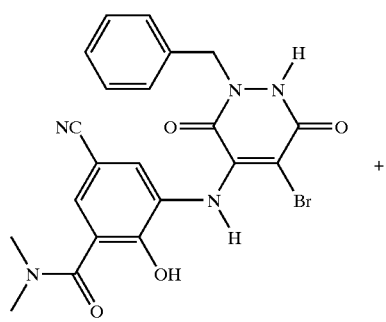 + |
|  |  |  | 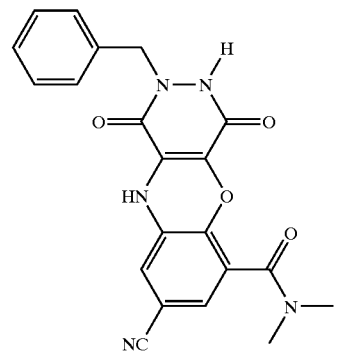 |
| 133.2 | 16 | 33 | 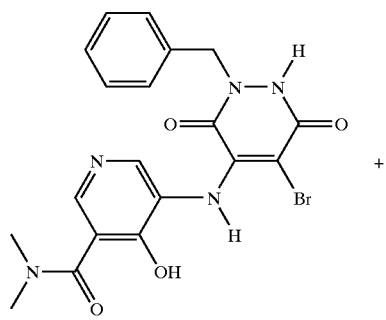 + |

| Ex. | (Prep Ex) Amine | (Prep Ex) Dibromo | Product |
|---|---|---|---|
| | | | 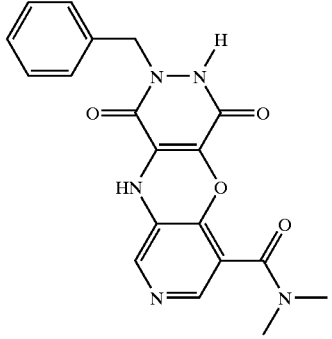 |

Preparative Example 134

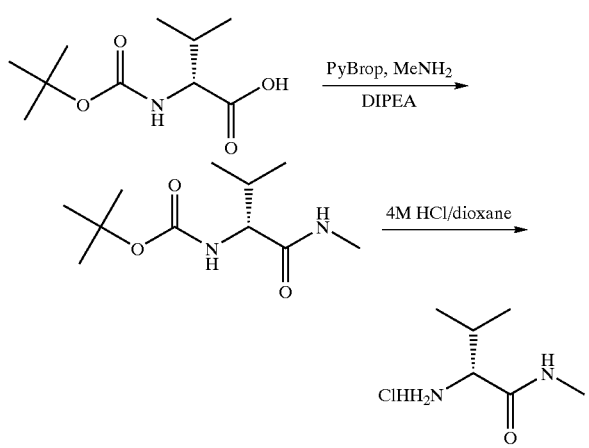

Step A

To a solution of N-protected amino acid (1.5 g, 6.9 mmol) in CH$_2$Cl$_2$ (25 mL) at room temperature was added DIPEA (3.6 mL, 20.7 mmol), and (PyBrop) (3.4 g, 6.9 mmol) followed by MeNH$_2$ (6.9 mL, 13.8 mmol, 2.0 M in CH$_2$Cl$_2$). The resulting solution was stirred for 18 h at room temperature (until TLC analysis deemed the reaction to be complete). The resulting mixture was washed sequentially with 10% citric acid (3×20 mL), sat. aq. NaHCO$_3$ (3×20 mL), and brine (3×20 mL). The organic layer was dried (Na$_2$SO$_4$), filtered, and concentrated under reduced pressure. The crude product was purified by flash chromatography eluting with CH$_2$Cl$_2$/MeOH (40:1) to afford 1.0 g (63% yield) of a solid.

Step B

To a round bottom flask charged with the N-protected amide (1.0 g, 4.35 mmol) from Step A above, was added 4N HCl/dioxane (10 mL). The mixture was stirred at room temperature for 2 h. The mixture was diluted with Et$_2$O (20 mL) and concentrated under reduced pressure. The crude product was treated with Et$_2$O (2×20 mL) and concentrated under reduced pressure to afford 0.72 g (~100% yield) of crude product as the HCl salt. This material was used without further purification or characterization.

Preparative Examples 135–137

Following the procedure set forth in Preparative Example 134 but using the commercially available N-protected amino acids and amines indicated, the amine hydrochloride products in the Table below were obtained.

| Prep Ex. | Amino acid | Amine | Product | Yield (%) |
|---|---|---|---|---|
| 135 | 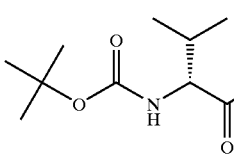 | 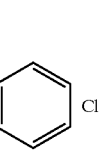 | 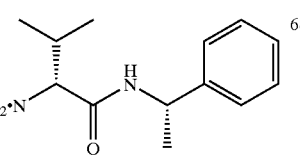 | 68% |
| 136 | 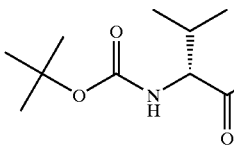 | 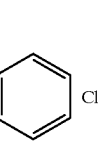 | 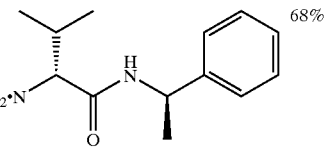 | 68% |

| Prep Ex. | Amino acid | Amine | Product | Yield (%) |
|---|---|---|---|---|
| 137 | 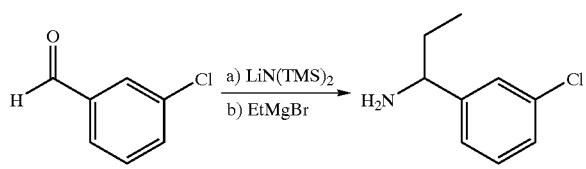 | | | 97% |

Preparative Example 138

To a solution of 3-chlorobenzaldehyde (2.0 g, 14.2 mmol) in THF (5 mL) at 0° C. was added LiN(TMS)$_2$ (17.0 ml, 1.0 M in THF) dropwise and the resulting solution was stirred for 20 min. EtMgBr (6.0 mL, 3.0 M in Et$_2$O) was added dropwise and the mixture was refluxed for 24 h. The mixture was cooled to room temperature, poured into sat. aq. NH$_4$Cl (50 mL), and then extracted with CH$_2$Cl$_2$ (3×50 volumes). The organic layers were combined and concentrated under reduced pressure. The crude residue was stirred with 3 M HCl (25 mL) for 30 min, the aqueous layer was then extracted with CH$_2$Cl$_2$ (3×15 mL) and the organic layers were discarded. The aqueous layer was cooled to 0° C. and treated with solid NaOH pellets until pH=10 was obtained. The aqueous layer was extracted with CH$_2$Cl$_2$ (3×15 mL) and the organic layers were combined. The organic layer was washed with brine (1×25 mL), dried (Na$_2$SO$_4$), and concentrated under reduced pressure to afford 1.6 g (66% yield) of the crude amine as an oil (MH$^+$ 170). This material was determined to be >90% pure and was used without further purification.

Preparative Examples 139–142

Following the procedure set forth in Preparative Example 138 but using the commercially available aldehydes and Grignard reagents indicated, the amine products listed in the Table below were obtained.

| Prep Ex. | Aldehyde | Grignard Reagent | Amine Product | 1. Yield (%) 2. MH$^+$ |
|---|---|---|---|---|
| 139 | | EtMgBr | | 1. 73% 2. 154 |
| 140 | | EtMgBr | | 1. 55% 2. 180 |
| 141 | | EtMgBr | | 1. 80% 2. 166 |
| 142 | | i-PrMgBr | | 1. 20% 2. 150 |

Preparative Example 143

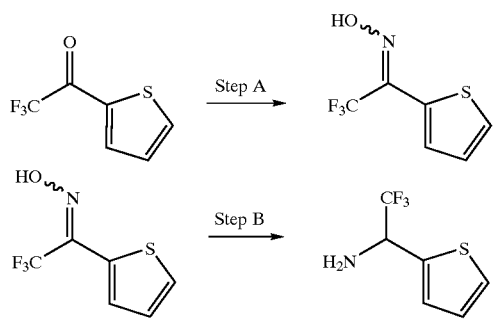

Step A

A mixture of 2-(trifluoroacetyl)thiophene (2 mL, 15.6 mmol), hydroxylamine hydrochloride (2.2 g, 2 eq), Diisopropylethylamine (5.5 mL, 2 eq) and MeOH (50 mL) was stirred at reflux for 48–72 hrs, then concentrated in vacuo. The residue was diluted with EtOAc, washed with 10% $KH_2PO_4$ and dried over $Na_2SO_4$ (anhydrous). Filtration and concentration afforded the desired oxime (2.9 g, 96%) which was used directly in Step B without further purification.

Step B

To a mixture of the product from Step A above in TFA (20 mL) was added Zn powder (3 g, 3 eq) portionwise over 30 min. The mixture was stirred at room temperature overnight. The solid was filtered and the mixture reduced under vacuo. Aqueous NaOH (2 M) was added and the mixture was extracted several times with $CH_2Cl_2$. The organic phase was dried over anhydrous $Na_2SO_4$, filtered and concentrated to afford the product (1.4 g, 50%).

Preparative Examples 144–148

Following the procedure set forth in Preparative Example 143 but using the commercially available ketones indicated, the amine products listed in the table below were obtained.

| Prep Example | Ketone | Amine Product | 1. Yield (%) 2. MH⁺ |
|---|---|---|---|
| 144 | (phenyl furan-2-yl ketone) | (amino(phenyl)furan-2-yl methane) | 1. 47% 2. 174 |
| 145 | (phenyl thiophen-2-yl ketone) | (amino(phenyl)thiophen-2-yl methane) | 1. 71% 2. 190 |
| 146 | (phenyl thiazol-2-yl ketone) | (amino(phenyl)thiazol-2-yl methane) | 1. 78% 2. 191 |
| 147 | (cyclohexyl thiophen-2-yl ketone) | (amino(cyclohexyl)thiophen-2-yl methane) | 1. 80% 2. 190 |
| 148 | (t-butyl thiophen-2-yl ketone) | (amino(t-butyl)thiophen-2-yl methane) | 1. 9% 2. 156 |

Preparative Example 149

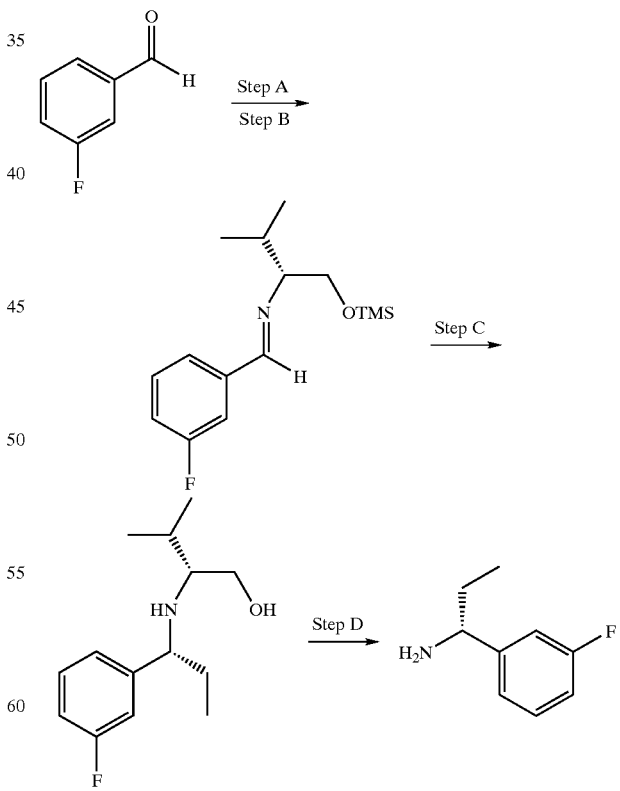

Step A

To a solution of (D)-valinol (4.16 g, 40.3 mmol) in $CH_2Cl_2$ (60 mL) at 0° C. was added $MgSO_4$ (20 g) followed by dropwise addition of 3-fluorobenzaldehyde (5.0 g, 40.3 mmol). The heterogenous solution was stirred at 0° C. for 2 h, was allowed to warm to room temperature and was stirred overnight (14 h). The mixture was filtered and the drying agent was washed with $CH_2Cl_2$ (2×10 mL). The filtrate was concentrated under reduced pressure to afford 8.4 g (100%) of a colorless oil which was taken onto the next step without further purification.

Step B

To a solution of the imine (8.4 g, 40.2 mmol) from Step A in $CH_2Cl_2$ (60 mL) at room temperature was added $Et_3N$ (6.2 mL, 44.5 mmol) followed by dropwise addition of TMSCI (5.7 mL, 44.5 mmol). The mixture was stirred for 6 h at room temperature whereupon the precipitate that had formed was filtered off and washed with $CH_2Cl_2$ (2×10 mL). The combined filtrate was concentrated under reduced pressure and was taken up in $Et_2O$/hexane (1:1/150 mL). The precipitate was filtered off and the filtrate was concentrated under reduced pressure to afford 10.1 g (89%) of the protected imine as a red oil. This material was taken onto the next step without further purification.

Step C

To a solution of EtI (4.0 g, 25.6 mmol) in $Et_2O$ (40 mL) at −78° C. was added t-BuLi (30.1 mL, 51.2 mmol, 1.7 M in pentane) and the mixture was stirred for 10 min. The mixture was warmed to room temperature, stirred for 1 h, and was recooled to 40° C. A solution of the imine (6.0 g, 21.4 mmol) from Step B in $Et_2O$ (30 mL) was added dropwise via addition funnel to afford a bright orange mixture. The reaction mixture was stirred for 1.5 h at 40° C. whereupon 3M HCl (50 mL) was added and the mixture was allowed to warm to room temperature. Water (50 mL) was added and the layers were separated. The aqueous layer was extracted with $Et_2O$ (2×30 mL) and the organic layers were combined and discarded. The aqueous layer was cooled to 0° C. and carefully treated with solid NaOH pellets until pH=12 was obtained. The aqueous layer was extracted with $Et_2O$ (3×30 mL) and the combined layers were washed with brine (1×30 mL). The organic layer was dried ($Na_2SO_4$), filtered, and concentrated under reduced pressure to afford 4.8 g (94% yield) of the amine as a red oil. This material was taken on crude to the, next step without further purification:

Step D

To a solution of amine (4.5 g, 18.8 mmol) from Step C in MeOH (80 mL) at room temperature was added $MeNH_2$ (25 mL, 40% in water) followed by the addition of a solution of $H_5IO_6$ (14.0 g, 61.4 mmol) in $H_2O$ (25 mL). The heterogenous mixture was stirred for 1.5 h (until the reaction was complete by TLC) and the precipitate was filtered off. The resulting filtrate was diluted with water (50 mL) and the mixture was extracted with $Et_2O$ (4×60 mL). The combined organic layers were concentrated to a volume of −30 mL whereupon 3M HCl (75 mL) was added. The mixture was stirred overnight (12 h at room temperature) whereupon the mixture was concentrated to remove the volatiles. The aqueous layer was extracted with $Et_2O$ (3×40 mL) and the organic layers were discarded. The aqueous layer was cooled to 0° C. and was carefully treated with solid NaOH pellets until pH ~12 was reached. The aqueous layer was extracted with $Et_2O$ (3×60 mL) and the combined organic layers were dried ($MgSO_4$). The organic layer was concentrated under reduced pressure to afford 2.8 g (97% yield) of the desired amine as a yellow oil [$MH^+$ 154]. This compound was proven to be >85% pure by $^1H$ NMR and was used without further purification.

Preparative Examples 150–156

Following the procedure set forth in Preparative Example 149 but using the commercially available aldehydes, amino alcohols, and organolithium reagents indicated, the optically pure amine products in the Table below were obtained.

| Prep Ex. | Aldehyde | Amino Alcohol | Organo lithium | Product | 1. Yield (%) 2. $MH^+$ |
|---|---|---|---|---|---|
| 150 | 4-fluorobenzaldehyde | (S)-2-amino-3-methyl-1-butanol | cyclopropyl-Li | (cyclopropyl)(4-fluorophenyl)methanamine | 1. 54% 2. 166 |
| 151 | thiophene-2-carbaldehyde | (S)-2-amino-3-methyl-1-butanol | EtLi | 1-(thiophen-2-yl)propan-1-amine | 1. 42% 2. 142 |
| 152 | benzaldehyde | (S)-2-amino-3-methyl-1-butanol | cyclopropyl-Li | cyclopropyl(phenyl)methanamine | 1. 62% 2. 148 |

-continued

| Prep Ex. | Aldehyde | Amino Alcohol | Organo lithium | Product | 1. Yield (%) 2. MH⁺ |
|---|---|---|---|---|---|
| 153 | ![thiophene-2-carbaldehyde] | ![amino alcohol isopropyl] | t-BuLi | ![product tBu thiophene] | 1. 27%  2. 256 |
| 154 | ![benzaldehyde] | ![amino alcohol isopropyl] | t-BuLi | ![product tBu phenyl] | 1. 15%  2. 164 |
| 155 | ![5-methylfurfural] | ![amino alcohol isopropyl] | EtLi | ![product Et methylfuran] | 1. 29%  2. 126 |
| 156 | ![5-methylfurfural] | ![amino alcohol isopropyl] | EtLi | ![product Et methylfuran] | 1. 35%  2. 126 |

Preparative Example 157

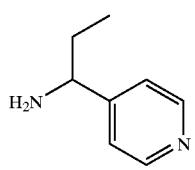

The product was prepared according to methods previously described: J. Med. Chem, 1996, 39, 3319–3323.

Preparative Example 158

The product was prepared according to methods previously described: J. Med. Chem. 1996, 39, 3319–3323.

Preparative Example 159

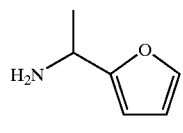

The product was prepared according to methods previously described: Chem. Pharm. Bull. 1991, 39, 181–183.

Preparative Example 160

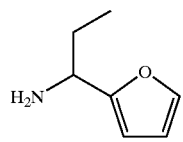

The product was prepared according to methods previously described: Chem. Pharm. Bull. 1991, 39, 181–183.

Preparative Example 161

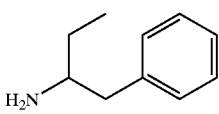

The product was prepared according to methods previously described: J. Med. Chem. 1988, 31, 2176–2186.

Preparative Example 162

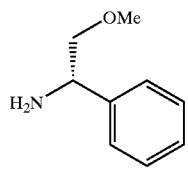

The product was prepared according to methods previously described: J. Org. Chem. 1978, 43, 892–898.

Preparative Example 163

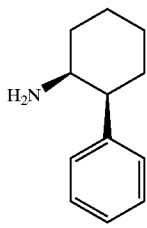

The product was prepared according to methods previously described: J. Org. Chem. 1987, 52, 4437–4444.

Preparative Example 164

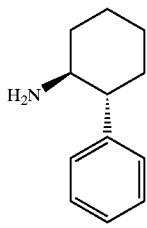

The product was prepared according to methods previously described: Bull. Chem. Soc. Jpn. 1962, 35, 11–16.

Example 500

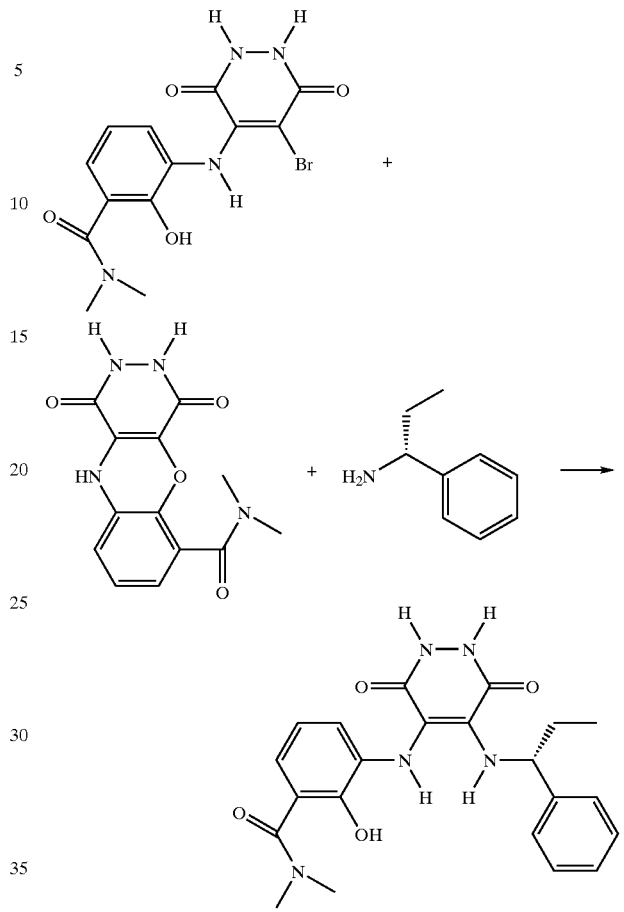

Following essentially the same procedure set forth in Preparative Example 34 (outlined in the literature Farmaco Ed. Sci.; IT; 32;1977; 173–179) using the product from Preparative Example 34 and benzyl amine, one could obtain the product.

Examples 501–828

Following essentially the same procedure set forth in Example 500 using the products from the Preparative Examples and the prepared or commercially available amines indicated, the products in the table below could be obtained.

| Ex. | Amine (Prep Ex) | Product of Prep. Ex | Product |
|---|---|---|---|
| 501 | H2N-C(CH3)3 | 34 | (structure shown) |

-continued

| Ex. | Amine (Prep Ex) | Product of Prep. Ex | Product |
|---|---|---|---|
| 502 | (S)-1-(thiophen-2-yl)propan-1-amine | 34 | |
| 503 | 1-(furan-2-yl)ethanamine | 34 | |
| 504 | aniline | 34 | |
| 505 | cyclohexanamine | 34 | |
| 506 | cyclopentanamine | 34 | |

-continued

| Ex. | Amine (Prep Ex) | Product of Prep. Ex | Product |
|---|---|---|---|
| 507 | | 34 | |
| 508 | | 38 | |
| 509 | | 39 | |
| 510 | | 34 | |

| Ex. | Amine (Prep Ex) | Product of Prep. Ex | Product |
|---|---|---|---|
| 511 | (S)-1-phenylpropylamine | 35 | pyridazine-3,6-dione with 3-carbamoyl-2-hydroxyphenylamino and (S)-1-phenylpropylamino substituents |
| 512 | (S)-1-phenylpropylamine | 36 | pyridazine-3,6-dione with 3-(morpholine-4-carbonyl)-2-hydroxyphenylamino and (S)-1-phenylpropylamino substituents |
| 513 | 2-pentylamine | 34 | pyridazine-3,6-dione with 3-(N,N-dimethylcarbamoyl)-2-hydroxyphenylamino and pentan-2-ylamino substituents |
| 514 | (S)-3-methylbutan-2-ylamine | 43 | pyridazine-3,6-dione with 1-methyl-5-(N,N-dimethylcarbamoyl)-4-hydroxypyrazol-3-ylamino and (S)-3-methylbutan-2-ylamino substituents |
| 515 | pent-4-yn-3-ylamine | 34 | pyridazine-3,6-dione with 3-(N,N-dimethylcarbamoyl)-2-hydroxyphenylamino and pent-1-yn-4-ylamino substituents |

-continued
| Ex. | Amine (Prep Ex) | Product of Prep. Ex | Product |
|---|---|---|---|
| 516 | 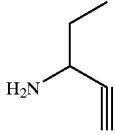 | 34 | 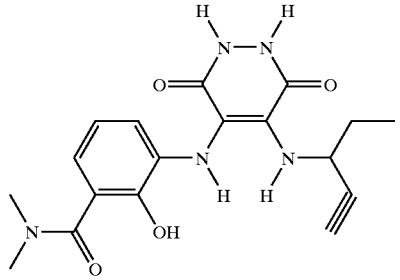 |
| 517 | 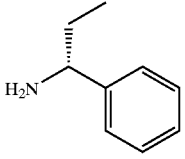 | 43 | 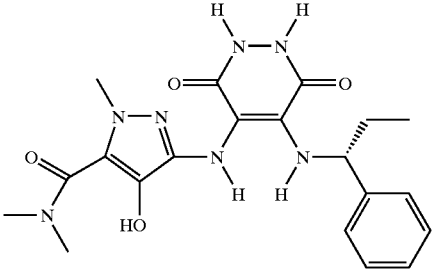 |
| 518 | 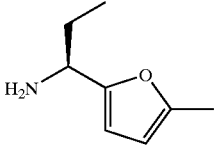 | 34 | 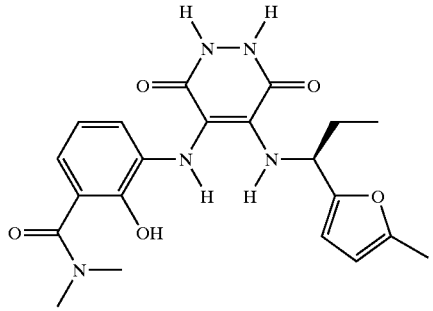 |
| 519 | 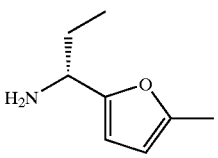 | 34 | 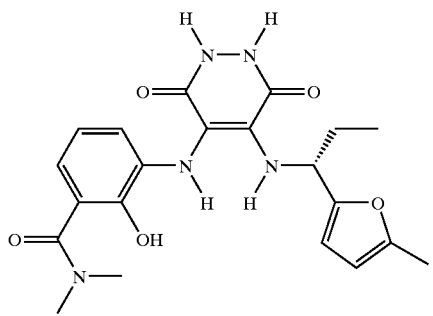 |
| 520 | 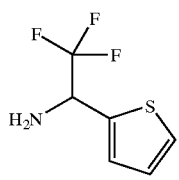 | 34 | 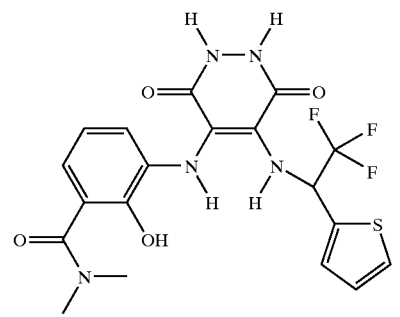 |

-continued

| Ex. | Amine (Prep Ex) | Product of Prep. Ex | Product |
|---|---|---|---|
| 521 | (S)-1-(3-fluorophenyl)propan-1-amine | 34 | pyridazine-3,6-dione bis-anilino product with 3-fluorophenylpropyl group and N,N-dimethyl salicylamide |
| 522 | (S)-3,3-dimethylbutan-2-amine | 34 | pyridazine-3,6-dione bis-anilino product with 3,3-dimethylbut-2-yl group and N,N-dimethyl salicylamide |
| 523 | (S)-3-methylbutan-2-amine | 41 | 5-cyano pyridazine-3,6-dione bis-anilino product with 3-methylbut-2-yl group and N,N-dimethyl salicylamide |
| 524 | (S)-3-methylbutan-2-amine | 34 | pyridazine-3,6-dione bis-anilino product with 3-methylbut-2-yl group and N,N-dimethyl salicylamide |
| 525 | (S)-1-phenylpropan-1-amine | 41 | 5-cyano pyridazine-3,6-dione bis-anilino product with 1-phenylpropyl group and N,N-dimethyl salicylamide |

-continued

| Ex. | Amine (Prep Ex) | Product of Prep. Ex | Product |
|---|---|---|---|
| 526 | (structure: H₂N-CH(CH₃)-thiophene) | 34 | (structure) |
| 527 | (structure: H₂N-CH(Et)-furan) | 34 | (structure) |
| 528 | (structure: H₂N-CH(iPr)-C(O)-NH-iPr) | 34 | (structure) |
| 529 | (structure: H₂N-CH(Et)-C(O)-NH-CH(CH₃)-Ph) | 34 | (structure) |
| 530 | (structure: H₂N-CH(Et)-thiophene) | 48 | (structure) |

-continued

| Ex. | Amine (Prep Ex) | Product of Prep. Ex | Product |
|---|---|---|---|
| 531 | (S)-1-phenylpropylamine | 37 | pyridazine-dione bis-anilino product with 2-hydroxy-N-methylbenzamide and (S)-1-phenylpropyl substituent |
| 532 | trans-2-methylcyclopentylamine | 34 | pyridazine-dione product with 2-hydroxy-N,N-dimethylbenzamide and trans-2-methylcyclopentyl substituent |
| 533 | trans-2-phenylcyclohexylamine | 34 | pyridazine-dione product with 2-hydroxy-N,N-dimethylbenzamide and trans-2-phenylcyclohexyl substituent |
| 534 | (S)-1-phenylpropylamine | 44 | pyridazine-dione product with methyl-substituted 2-hydroxy-N,N-dimethylbenzamide and (S)-1-phenylpropyl substituent |
| 535 | 1-(5-methylfuran-2-yl)propylamine | 34 | pyridazine-dione product with 2-hydroxy-N,N-dimethylbenzamide and 1-(5-methylfuran-2-yl)propyl substituent |

-continued

| Ex. | Amine (Prep Ex) | Product of Prep. Ex | Product |
|---|---|---|---|
| 536 | cycloheptylamine | 34 | |
| 537 | (S)-1-(thiophen-2-yl)propan-1-amine | 42 | |
| 538 | (S)-1-phenylpropan-1-amine | 40 | |
| 540 | (S)-2,2,2-trifluoro-1-(thiophen-2-yl)ethan-1-amine | 34 | |
| 541 | (S)-1-(benzo[d][1,3]dioxol-5-yl)propan-1-amine | 34 | |

-continued

| Ex. | Amine (Prep Ex) | Product of Prep. Ex | Product |
|---|---|---|---|
| 542 | tert-butylamine | 49 | |
| 543 | (S)-1-(thiophen-2-yl)propan-1-amine | 49 | |
| 544 | (S)-1-phenylpropan-1-amine | 64 | |
| 545 | cyclopropyl(thiophen-2-yl)methanamine | 49 | |
| 546 | 1-(furan-2-yl)ethanamine | 49 | |

-continued

| Ex. | Amine (Prep Ex) | Product of Prep. Ex | Product |
|---|---|---|---|
| 547 | aniline | 49 | |
| 548 | cyclohexylamine | 49 | |
| 549 | cyclopentylamine | 49 | |
| 550 | (S)-1-(thiophen-2-yl)-2,2-dimethylpropan-1-amine | 49 | |
| 551 | (S)-1-phenylpropan-1-amine | 57 | |

-continued

| Ex. | Amine (Prep Ex) | Product of Prep. Ex | Product |
|---|---|---|---|
| 552 | (sec-butyl amine structure) | 49 | (product structure) |
| 553 | (1-(thiophen-2-yl)-2,2,2-trifluoroethylamine structure) | 49 | (product structure) |
| 554 | (tert-butyl phenyl methanamine structure) | 49 | (product structure) |
| 555 | (1-(4-methoxyphenyl)propylamine structure) | 49 | (product structure) |

-continued

| Ex. | Amine (Prep Ex) | Product of Prep. Ex | Product |
|---|---|---|---|
| 556 | | 57 | |
| 557 | | 58 | |
| 558 | | 59 | |
| 559 | | 49 | |

-continued
| Ex. | Amine (Prep Ex) | Product of Prep. Ex | Product |
|---|---|---|---|
| 560 | 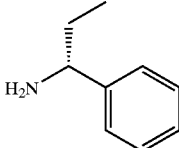 | 50 | 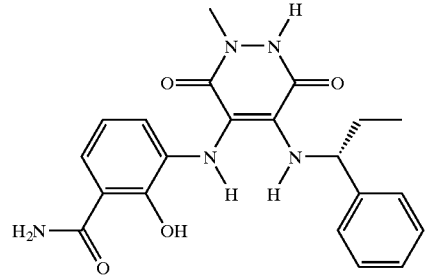 |
| 561 | 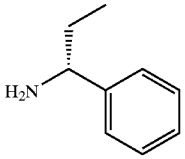 | 51 | 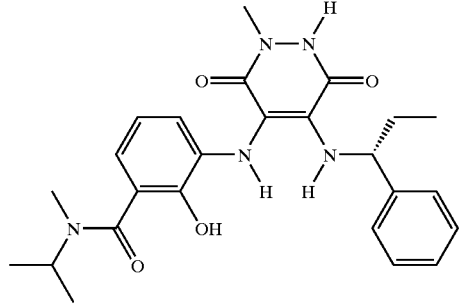 |
| 562 | 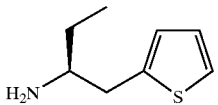 | 49 | 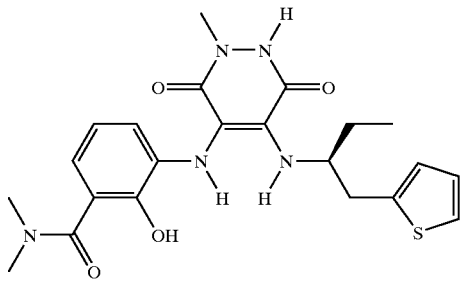 |
| 563 | 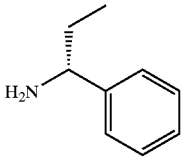 | 52 | 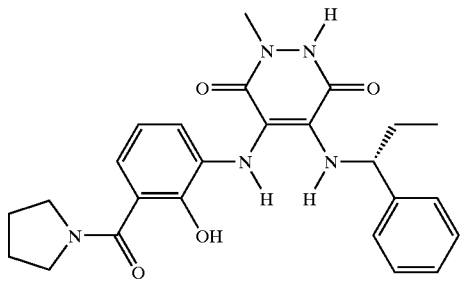 |
| 564 | 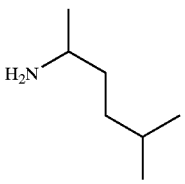 | 49 | 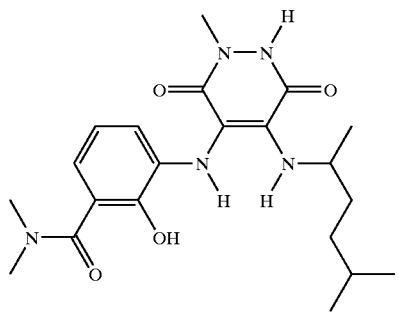 |

-continued

| Ex. | Amine (Prep Ex) | Product of Prep. Ex | Product |
|---|---|---|---|
| 565 | (S)-1-phenylpropylamine | 53 | |
| 566 | 2-pentylamine | 49 | |
| 567 | (S)-1-phenylpropylamine | 54 | |
| 568 | (S)-3-methyl-2-butylamine | 66 | |
| 569 | (S)-1-phenylpropylamine | 66 | |

-continued

| Ex. | Amine (Prep Ex) | Product of Prep. Ex | Product |
|---|---|---|---|
| 570 | | 49 | |
| 571 | | 49 | |
| 572 | | 49 | |
| 573 | | 49 | |
| 574 | | 49 | |

-continued

| Ex. | Amine (Prep Ex) | Product of Prep. Ex | Product |
|---|---|---|---|
| 575 | (structure) | 49 | (structure) |
| 576 | (structure) | 49 | (structure) |
| 577 | (structure) | 49 | (structure) |
| 578 | (structure) | 49 | (structure) |
| 579 | (structure) | 63 | (structure) |

US 6,878,709 B2
-continued
| Ex. | Amine (Prep Ex) | Product of Prep. Ex | Product |
|---|---|---|---|
| 580 | 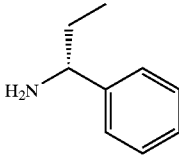 | 63 | 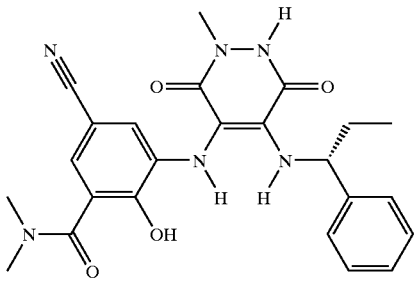 |
| 581 | 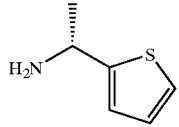 | 49 | 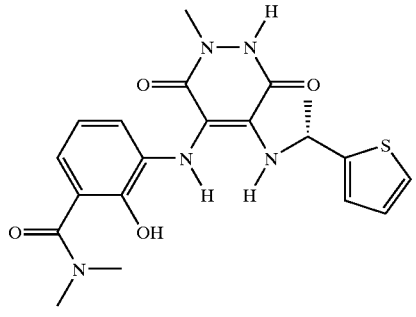 |
| 582 | 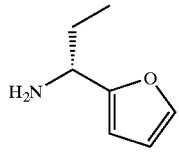 | 49 | 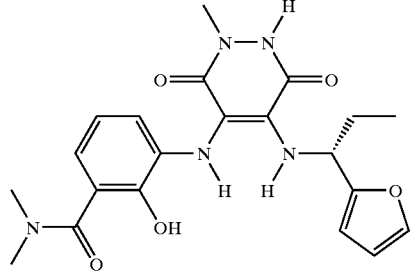 |
| 583 | 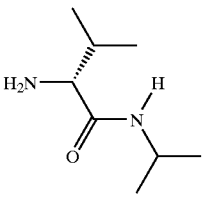 | 49 | 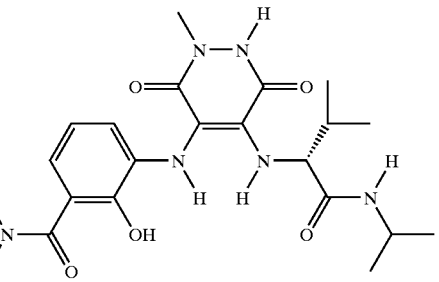 |
| 584 | 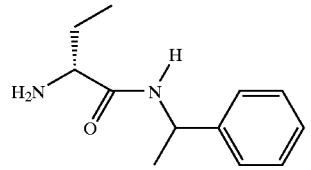 | 49 | 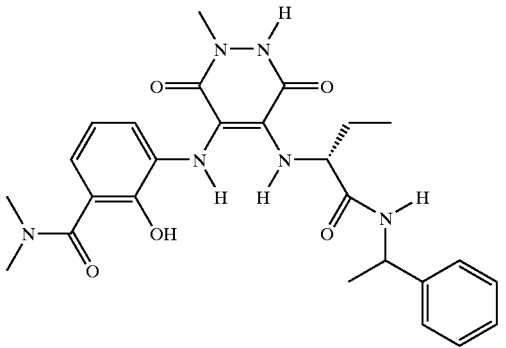 |

| Ex. | Amine (Prep Ex) | Product of Prep. Ex | Product |
|---|---|---|---|
| 585 | (S)-1-(thiophen-2-yl)propan-1-amine | 62 | |
| 586 | (S)-1-(thiophen-2-yl)propan-1-amine | 61 | |
| 587 | 1-(thiazol-2-yl)propan-1-amine | 49 | |
| 588 | (S)-2-methoxy-1-phenylethan-1-amine | 49 | |
| 589 | (S)-1-(benzyloxy)butan-2-amine | 49 | |

-continued

| Ex. | Amine (Prep Ex) | Product of Prep. Ex | Product |
|---|---|---|---|
| 590 | (structure) | 55 | (structure) |
| 591 | (structure) | 49 | (structure) |
| 592 | (structure) | 49 | (structure) |
| 593 | (structure) | 49 | (structure) |
| 594 | (structure) | 67 | (structure) |

-continued

| Ex. | Amine (Prep Ex) | Product of Prep. Ex | Product |
|---|---|---|---|
| 595 | | 49 | |
| 596 | | 49 | |
| 597 | | 49 | |
| 598 | | 49 | |
| 599 | | 65 | |

-continued
| Ex. | Amine (Prep Ex) | Product of Prep. Ex | Product |
|---|---|---|---|
| 600 | 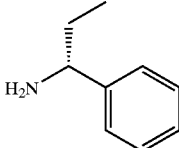 | 60 | 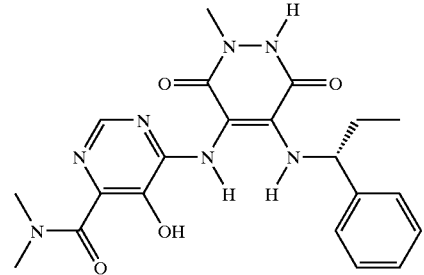 |
| 601 | 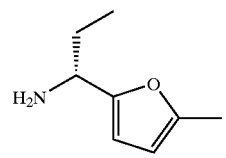 | 49 | 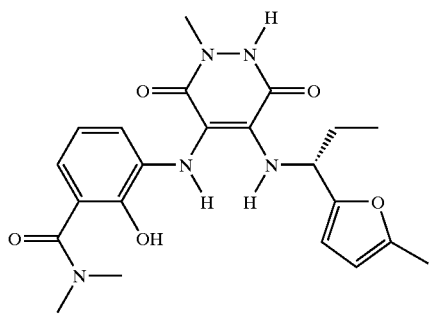 |
| 602 | 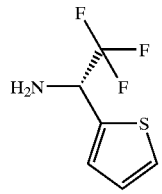 | 49 | 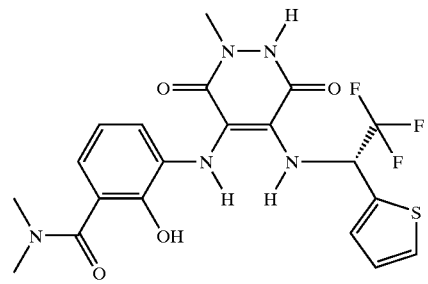 |
| 603 | 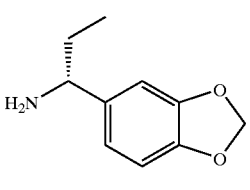 | 49 | 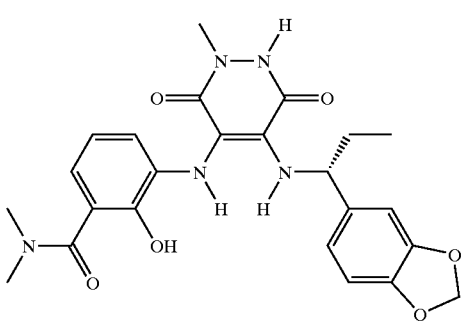 |
| 605 |  | 72 | 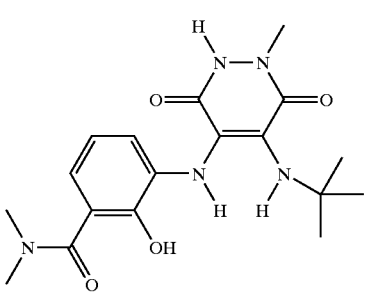 |

-continued
| Ex. | Amine (Prep Ex) | Product of Prep. Ex | Product |
|---|---|---|---|
| 607 | 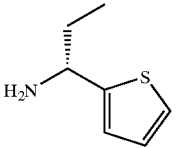 | 72 | 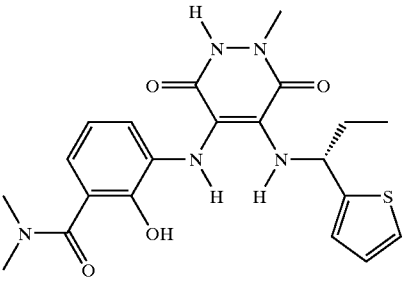 |
| 608 | 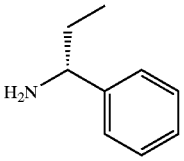 | 87 | 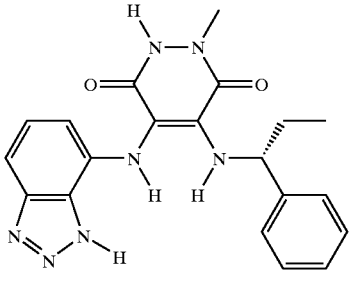 |
| 609 | 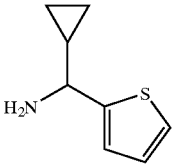 | 72 | 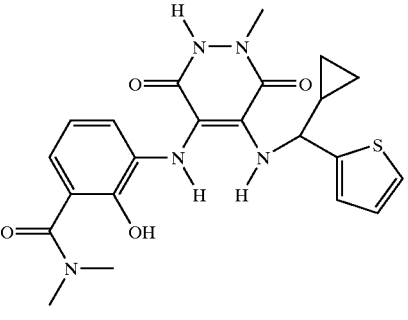 |
| 610 | 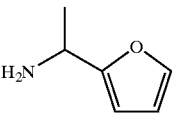 | 72 | 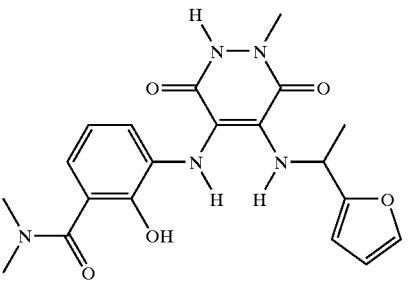 |
| 611 | 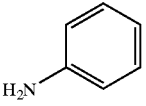 | 72 | 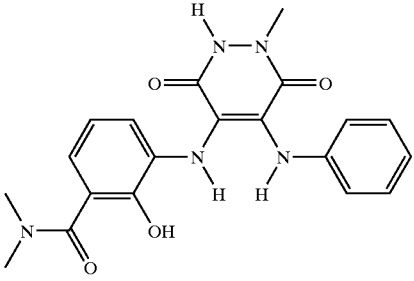 |

-continued

| Ex. | Amine (Prep Ex) | Product of Prep. Ex | Product |
|---|---|---|---|
| 612 | cyclohexylamine | 72 | |
| 613 | cyclopentylamine | 72 | |
| 614 | (S)-1-(thiophen-2-yl)-2,2-dimethylpropan-1-amine | 72 | |
| 615 | (S)-1-phenylpropan-1-amine | 79 | |
| 616 | sec-butylamine (pentan-3-amine) | 72 | |

| Ex. | Amine (Prep Ex) | Product of Prep. Ex | Product |
|---|---|---|---|
| 617 | 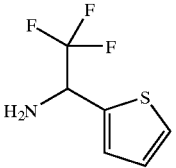 | 72 | 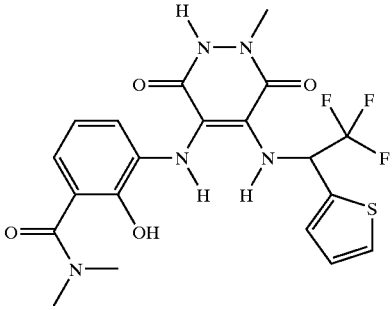 |
| 618 | 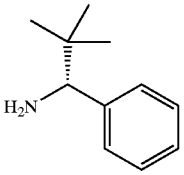 | 72 | 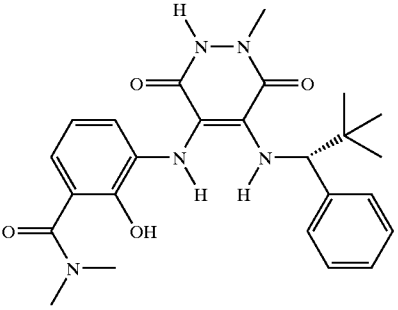 |
| 619 | 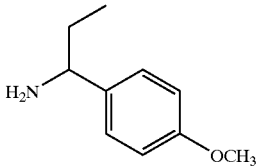 | 72 | 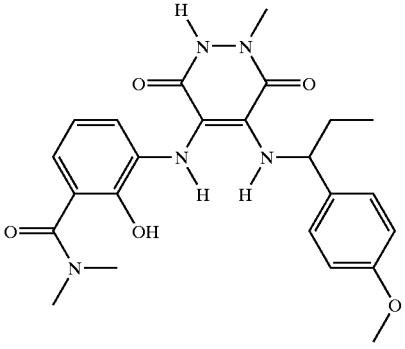 |
| 620 | 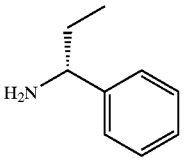 | 80 | 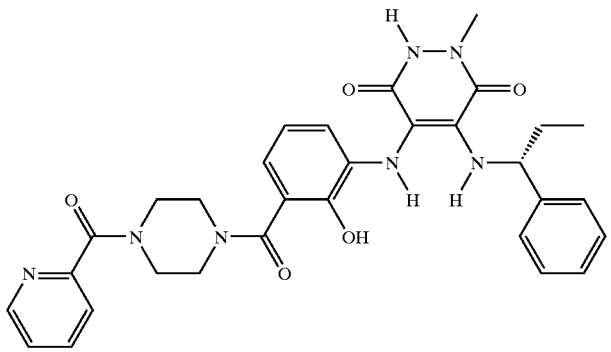 |

-continued

| Ex. | Amine (Prep Ex) | Product of Prep. Ex | Product |
|---|---|---|---|
| 621 | | 81 | |
| 622 | | 82 | |
| 623 | | 72 | |
| 624 | | 73 | |

-continued

| Ex. | Amine (Prep Ex) | Product of Prep. Ex | Product |
|---|---|---|---|
| 625 | (S)-1-phenylpropylamine | 74 | pyridazine-dione with 3-(N-methyl-N-isopropylcarbamoyl)-2-hydroxyphenylamino and (S)-1-phenylpropylamino substituents |
| 626 | (S)-1-(thiophen-2-ylmethyl)propylamine | 72 | pyridazine-dione with 3-(N,N-dimethylcarbamoyl)-2-hydroxyphenylamino and (S)-1-(thiophen-2-ylmethyl)propylamino substituents |
| 627 | (S)-1-phenylpropylamine | 75 | pyridazine-dione with 3-(pyrrolidin-1-ylcarbonyl)-2-hydroxyphenylamino and (S)-1-phenylpropylamino substituents |
| 628 | 4-methylpentan-2-ylamine | 72 | pyridazine-dione with 3-(N,N-dimethylcarbamoyl)-2-hydroxyphenylamino and 4-methylpentan-2-ylamino substituents |
| 629 | (S)-1-phenylpropylamine | 76 | pyridazine-dione with 3-(morpholin-4-ylcarbonyl)-2-hydroxyphenylamino and (S)-1-phenylpropylamino substituents |

| Ex. | Amine (Prep Ex) | Product of Prep. Ex | Product |
|---|---|---|---|
| 630 | | 72 | |
| 631 | | 77 | |
| 632 | | 89 | |
| 633 | | 89 | |
| 634 | | 72 | |

| Ex. | Amine (Prep Ex) | Product of Prep. Ex | Product |
|---|---|---|---|
| 635 | (pent-4-yn-2-ylamine structure) | 72 | (product structure) |
| 636 | (pent-1-yn-3-ylamine structure) | 72 | (product structure) |
| 637 | ((S)-1-phenylpropylamine structure) | 72 | (product structure) |
| 638 | (2,2,2-trifluoro-1-(thiophen-2-yl)ethylamine structure) | 72 | (product structure) |
| 639 | ((S)-cyclopropyl(phenyl)methanamine structure) | 72 | (product structure) |

| Ex. | Amine (Prep Ex) | Product of Prep. Ex | Product |
|---|---|---|---|
| 640 | (S)-1-(3-fluorophenyl)propylamine | 72 | pyridazine-dione bis-amino product with 3-hydroxy-N,N-dimethylbenzamide and (S)-1-(3-fluorophenyl)propyl group |
| 641 | (S)-3,3-dimethylbutan-2-amine | 72 | pyridazine-dione bis-amino product with 3-hydroxy-N,N-dimethylbenzamide and (S)-3,3-dimethylbutan-2-yl group |
| 642 | (S)-3-methylbutan-2-amine | 72 | pyridazine-dione bis-amino product with 3-hydroxy-N,N-dimethylbenzamide and (S)-3-methylbutan-2-yl group |
| 643 | (S)-3-methylbutan-2-amine | 86 | pyridazine-dione bis-amino product with 5-cyano-2-hydroxy-N,N-dimethylbenzamide and (S)-3-methylbutan-2-yl group |
| 644 | (S)-1-phenylpropylamine | 86 | pyridazine-dione bis-amino product with 5-cyano-2-hydroxy-N,N-dimethylbenzamide and (S)-1-phenylpropyl group |

-continued

| Ex. | Amine (Prep Ex) | Product of Prep. Ex | Product |
|---|---|---|---|
| 645 | (S)-1-(thiophen-2-yl)ethylamine | 72 | |
| 646 | (S)-1-(furan-2-yl)propylamine | 72 | |
| 647 | (S)-2-amino-N-isopropyl-3-methylbutanamide | 72 | |
| 648 | (S)-2-amino-N-(1-phenylethyl)butanamide | 72 | |
| 649 | (S)-1-(thiophen-2-yl)propylamine | 85 | |

-continued
| Ex. | Amine (Prep Ex) | Product of Prep. Ex | Product |
|---|---|---|---|
| 650 | 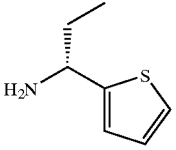 | 84 | 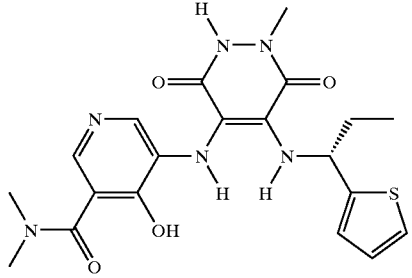 |
| 651 | 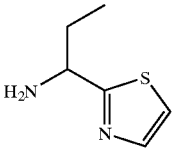 | 72 | 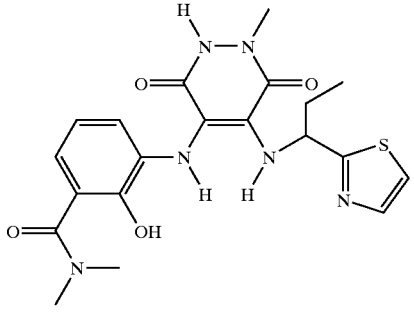 |
| 652 | 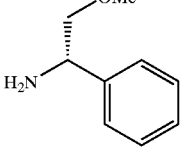 | 72 | 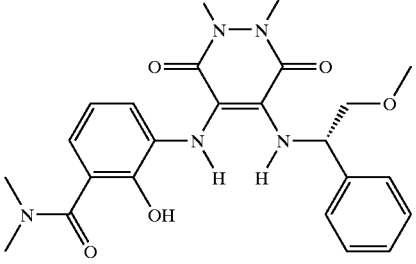 |
| 653 | 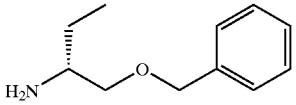 | 72 | 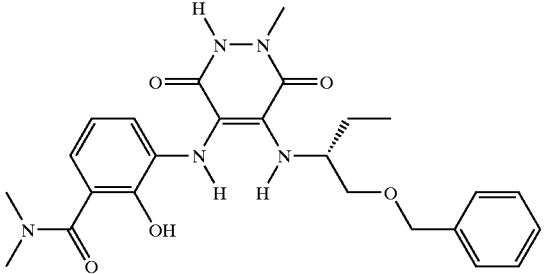 |
| 654 | 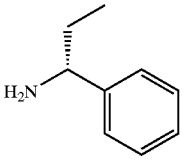 | 78 | 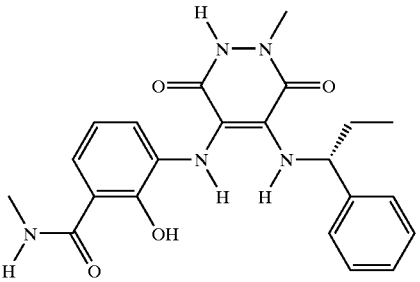 |

-continued

| Ex. | Amine (Prep Ex) | Product of Prep. Ex | Product |
|---|---|---|---|
| 655 | (structure: trans-2-(methoxymethyl)cyclohexylamine) | 72 | (product structure) |
| 656 | (structure: trans-2-methylcyclopentylamine) | 72 | (product structure) |
| 657 | (structure: trans-2-phenylcyclohexylamine) | 72 | (product structure) |
| 658 | (structure: (S)-1-phenylpropylamine) | 90 | (product structure) |
| 659 | (structure: (S)-1-(5-methylfuran-2-yl)propylamine) | 72 | (product structure) |

-continued

| Ex. | Amine (Prep Ex) | Product of Prep. Ex | Product |
|---|---|---|---|
| 660 | (S)-2-amino-3-methyl-1-butanol | 72 | |
| 661 | (S)-2-amino-1-methoxybutane | 72 | |
| 662 | cycloheptylamine | 72 | |
| 663 | (S)-1-(2-thienyl)propylamine | 88 | |
| 664 | (S)-1-phenylpropylamine | 83 | |

-continued

| Ex. | Amine (Prep Ex) | Product of Prep. Ex | Product |
|---|---|---|---|
| 665 | | 72 | |
| 666 | | 72 | |
| 667 | | 72 | |
| 668 | | 94 | |
| 669 | | 94 | |

-continued
| Ex. | Amine (Prep Ex) | Product of Prep. Ex | Product |
|---|---|---|---|
| 670 | 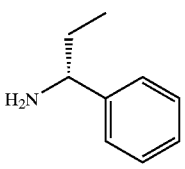 | 109 | 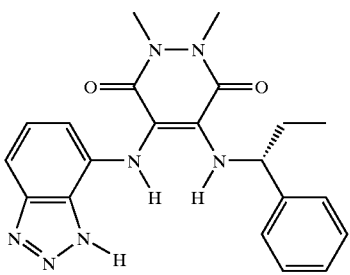 |
| 671 | 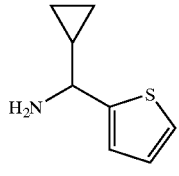 | 94 | 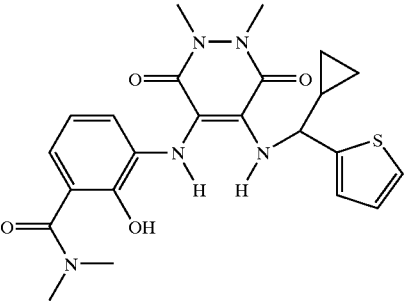 |
| 672 | 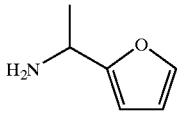 | 94 | 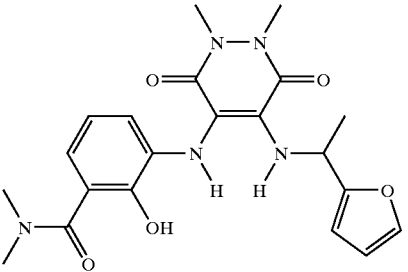 |
| 673 | 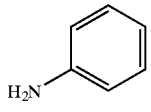 | 94 | 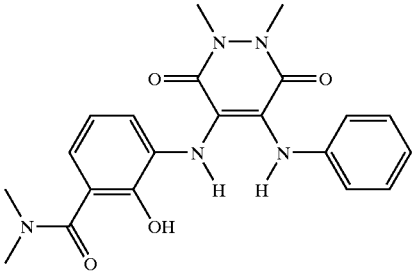 |
| 674 | 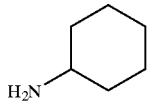 | 94 | 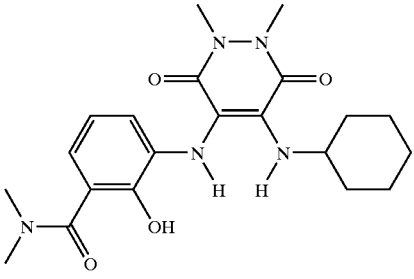 |

-continued
| Ex. | Amine (Prep Ex) | Product of Prep. Ex | Product |
|---|---|---|---|
| 675 | 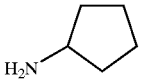 | 94 | 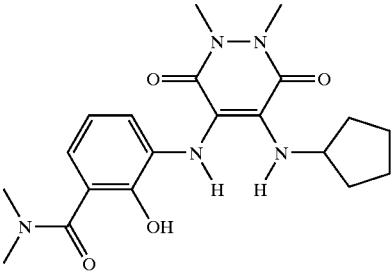 |
| 676 | 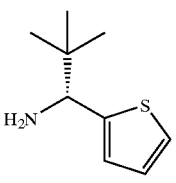 | 94 | 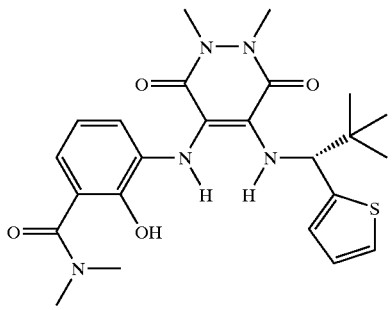 |
| 678 | 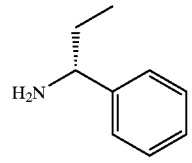 | 101 | 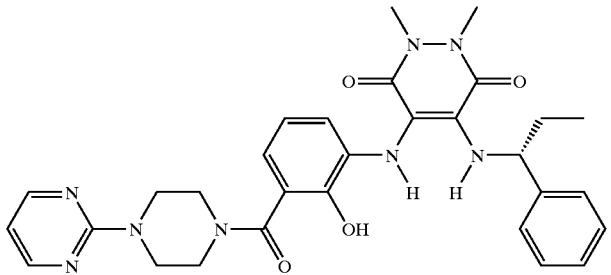 |
| 679 | 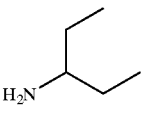 | 94 | 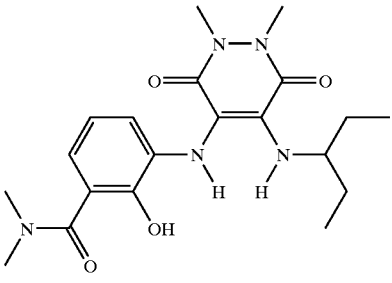 |
| 680 | 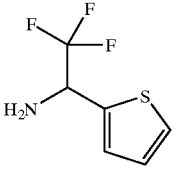 | 94 | 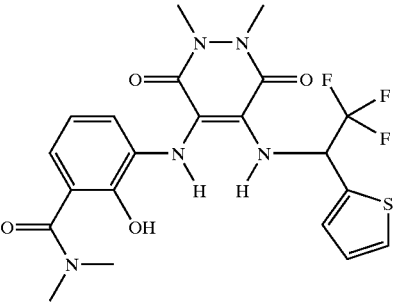 |

-continued

| Ex. | Amine (Prep Ex) | Product of Prep. Ex | Product |
|---|---|---|---|
| 681 | | 94 | |
| 682 | | 94 | |
| 683 | | 102 | |
| 684 | | 103 | |

| Ex. | Amine (Prep Ex) | Product of Prep. Ex | Product |
|---|---|---|---|
| 685 | 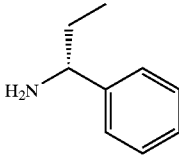 | 104 | 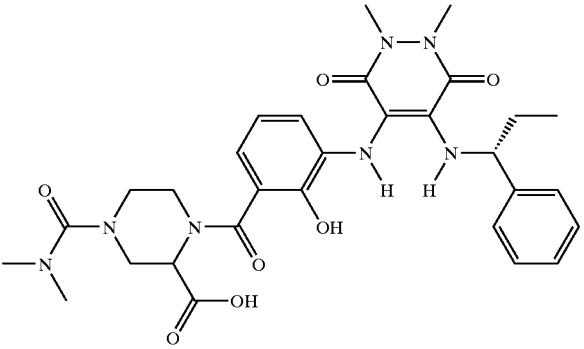 |
| 686 | 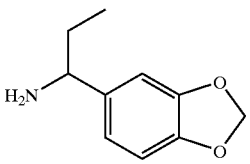 | 94 | 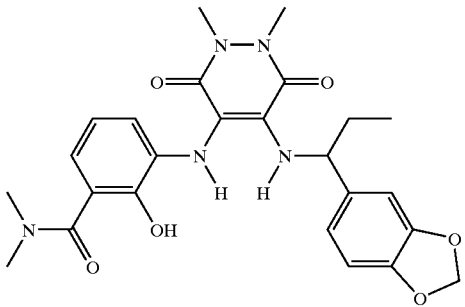 |
| 687 | 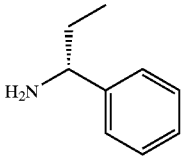 | 95 | 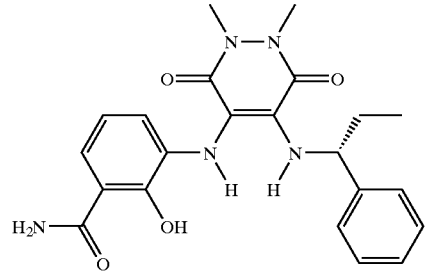 |
| 688 | 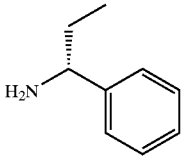 | 96 | 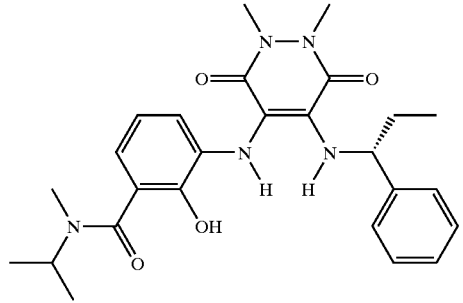 |
| 689 | 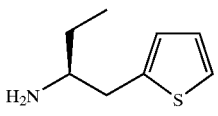 | 94 | 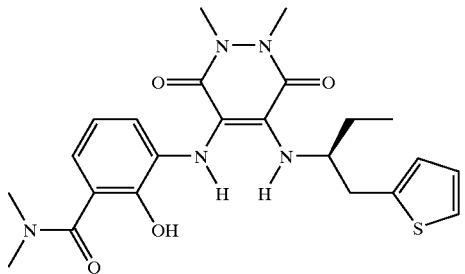 |

-continued

| Ex. | Amine (Prep Ex) | Product of Prep. Ex | Product |
|---|---|---|---|
| 690 | (S)-1-phenylpropylamine | 97 | pyrrolidine-carbonyl phenol pyridazinedione with (S)-1-phenylpropylamino substituent |
| 691 | 4-methylpentan-2-amine | 94 | N,N-dimethylbenzamide phenol pyridazinedione with 4-methylpentan-2-ylamino substituent |
| 692 | (S)-1-phenylpropylamine | 98 | morpholine-carbonyl phenol pyridazinedione with (S)-1-phenylpropylamino substituent |
| 693 | pentan-2-amine | 94 | N,N-dimethylbenzamide phenol pyridazinedione with pentan-2-ylamino substituent |
| 694 | (S)-1-phenylpropylamine | 99 | (S)-3-(hydroxymethyl)pyrrolidine-carbonyl phenol pyridazinedione with (S)-1-phenylpropylamino substituent |

-continued

| Ex. | Amine (Prep Ex) | Product of Prep. Ex | Product |
|---|---|---|---|
| 695 | (structure) | 111 | (structure) |
| 696 | (structure) | 111 | (structure) |
| 697 | (structure) | 94 | (structure) |
| 698 | (structure) | 94 | (structure) |
| 699 | (structure) | 94 | (structure) |

-continued

| Ex. | Amine (Prep Ex) | Product of Prep. Ex | Product |
|---|---|---|---|
| 700 | (structure) | 94 | (structure) |
| 701 | (structure) | 94 | (structure) |
| 702 | (structure) | 94 | (structure) |
| 703 | (structure) | 94 | (structure) |
| 704 | (structure) | 94 | (structure) |

-continued

| Ex. | Amine (Prep Ex) | Product of Prep. Ex | Product |
|---|---|---|---|
| 705 | (S)-sec-butylamine | 94 | |
| 706 | (S)-sec-butylamine | 108 | |
| 707 | (S)-1-phenylpropylamine | 108 | |
| 708 | (S)-1-(thiophen-2-yl)ethylamine | 94 | |
| 709 | (S)-1-(furan-2-yl)propylamine | 94 | |

-continued

| Ex. | Amine (Prep Ex) | Product of Prep. Ex | Product |
|---|---|---|---|
| 710 | | 94 | |
| 711 | | 94 | |
| 712 | | 107 | |
| 713 | | 106 | |
| 714 | | 94 | |

-continued

| Ex. | Amine (Prep Ex) | Product of Prep. Ex | Product |
|---|---|---|---|
| 715 | (S)-1-phenyl-2-methoxyethylamine | 94 | |
| 716 | (S)-1-(benzyloxymethyl)propylamine | 94 | |
| 717 | (S)-1-phenylpropylamine | 100 | |
| 718 | (1S,2S)-2-(methoxymethyl)cyclohexylamine | 94 | |
| 719 | (1S,2S)-2-methylcyclopentylamine | 94 | |

-continued
| Ex. | Amine (Prep Ex) | Product of Prep. Ex | Product |
|---|---|---|---|
| 720 | 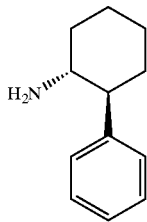 | 94 | 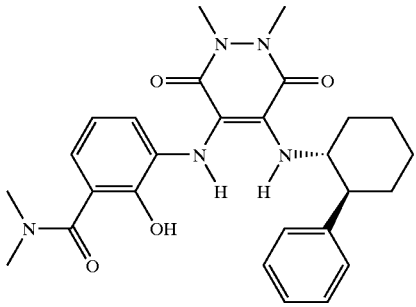 |
| 721 | 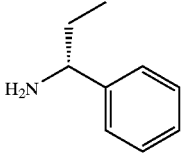 | 112 | 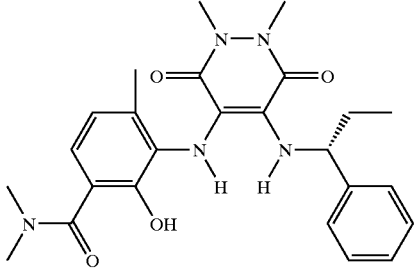 |
| 722 | 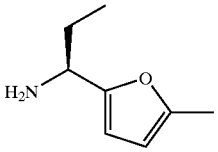 | 94 | 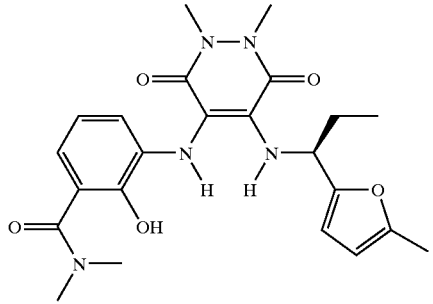 |
| 723 | 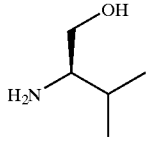 | 94 | 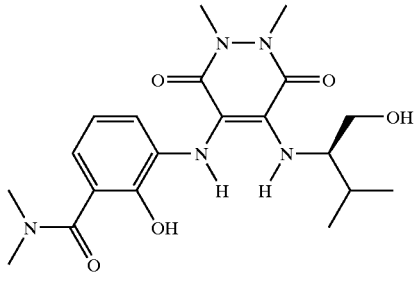 |
| 724 | 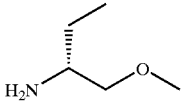 | 94 | 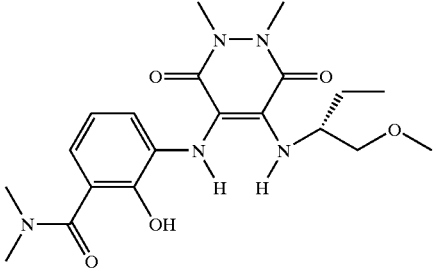 |

-continued

| Ex. | Amine (Prep Ex) | Product of Prep. Ex | Product |
|---|---|---|---|
| 725 | | 94 | |
| 726 | | 110 | |
| 727 | | 105 | |
| 728 | | 94 | |
| 729 | | 94 | |

| Ex. | Amine (Prep Ex) | Product of Prep. Ex | Product |
|---|---|---|---|
| 730 | (chemical structure) | 94 | (chemical structure) |
| 731 | (chemical structure) | 116 | (chemical structure) |
| 732 | (chemical structure) | 116 | (chemical structure) |
| 733 | (chemical structure) | 116 | (chemical structure) |
| 734 | (chemical structure) | 116 | (chemical structure) |

-continued

| Ex. | Amine (Prep Ex) | Product of Prep. Ex | Product |
| --- | --- | --- | --- |
| 735 | (S)-1-(thiophen-2-yl)ethylamine | 116 | |
| 736 | (S)-1-(furan-2-yl)propylamine | 116 | |
| 737 | (S)-1-phenylpropylamine | 119 | |
| 738 | L-valine N-isopropylamide | 116 | |
| 739 | (S)-2-amino-N-(1-phenylethyl)butanamide | 116 | |

-continued

| Ex. | Amine (Prep Ex) | Product of Prep. Ex | Product |
|---|---|---|---|
| 740 | (S)-1-(thiophen-2-yl)propan-1-amine | 120 | |
| 741 | (S)-1-phenylpropan-1-amine | 118 | |
| 742 | (S)-1-(thiophen-2-yl)propan-1-amine | 116 | |
| 743 | pentan-2-amine | 116 | |
| 744 | 1-(furan-2-yl)ethan-1-amine | 116 | |

-continued
| Ex. | Amine (Prep Ex) | Product of Prep. Ex | Product |
|---|---|---|---|
| 745 | 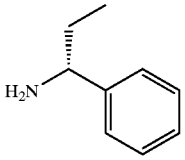 | 117 | 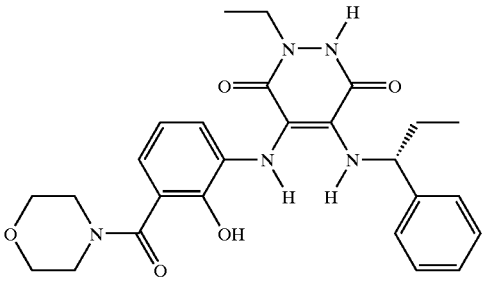 |
| 746 | 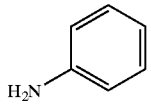 | 116 | 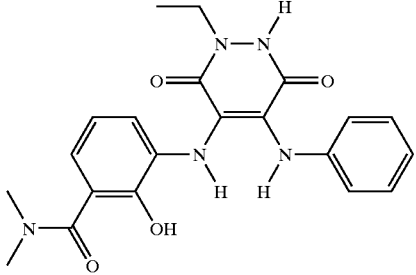 |
| 747 | 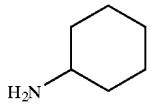 | 116 | 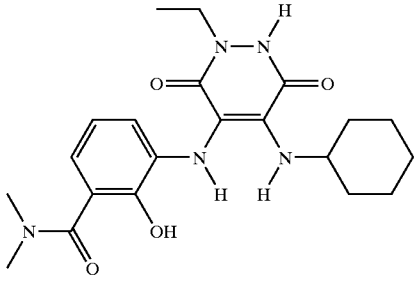 |
| 748 | 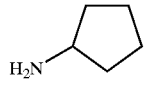 | 116 | 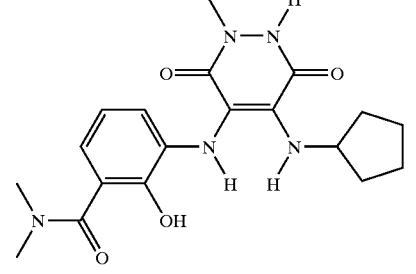 |
| 749 | 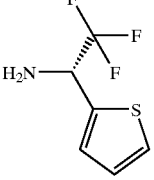 | 116 | 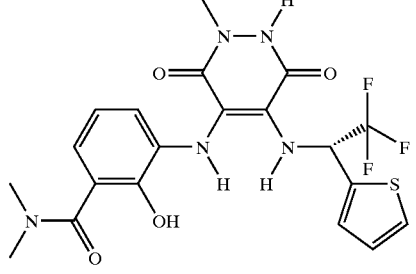 |

-continued

| Ex. | Amine (Prep Ex) | Product of Prep. Ex | Product |
|---|---|---|---|
| 750 | | 116 | |
| 751 | | 126 | |
| 752 | | 126 | |
| 753 | | 126 | |

| Ex. | Amine (Prep Ex) | Product of Prep. Ex | Product |
|---|---|---|---|
| 734 | (structure) | 126 | (structure) |
| 755 | (structure) | 126 | (structure) |
| 756 | (structure) | 126 | (structure) |
| 757 | (structure) | 129 | (structure) |

-continued

| Ex. | Amine (Prep Ex) | Product of Prep. Ex | Product |
|---|---|---|---|
| 758 | | 126 | |
| 759 | | 126 | |
| 760 | | 130 | |
| 761 | | 128 | |

-continued

| Ex. | Amine (Prep Ex) | Product of Prep. Ex | Product |
|---|---|---|---|
| 762 | (S)-1-(thiophen-2-yl)propan-1-amine | 126 | |
| 763 | pentan-2-amine | 126 | |
| 764 | 1-(furan-2-yl)ethan-1-amine | 126 | |
| 765 | (S)-1-phenylethan-1-amine | 127 | |

-continued

| Ex. | Amine (Prep Ex) | Product of Prep. Ex | Product |
|---|---|---|---|
| 766 | aniline | 126 | (structure) |
| 767 | cyclohexylamine | 126 | (structure) |
| 768 | cyclopentylamine | 126 | (structure) |
| 769 | (1S)-2,2,2-trifluoro-1-(thiophen-2-yl)ethylamine | 126 | (structure) |

-continued
| Ex. | Amine (Prep Ex) | Product of Prep. Ex | Product |
|---|---|---|---|
| 770 | 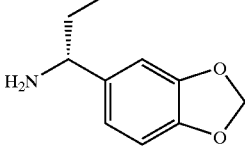 | 126 | 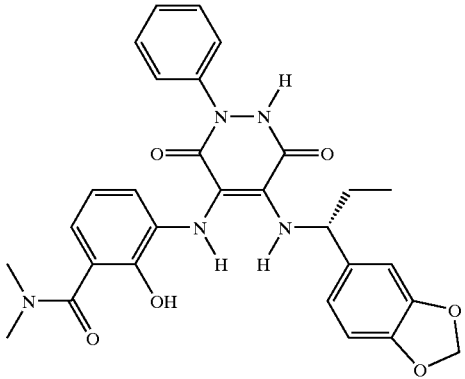 |
| 771 | 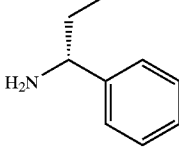 | 131 | 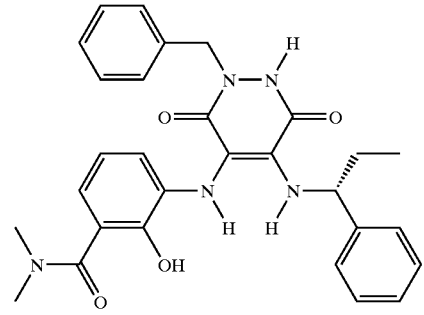 |
| 772 |  | 131 | 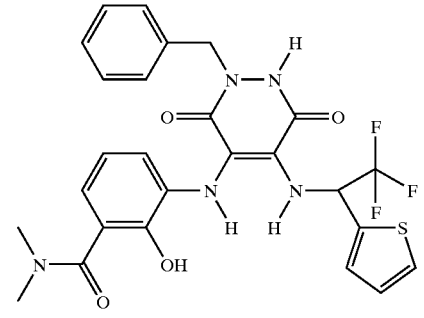 |
| 773 | 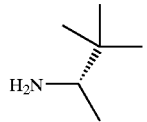 | 131 | 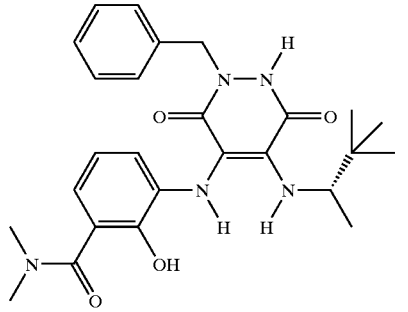 |

-continued

| Ex. | Amine (Prep Ex) | Product of Prep. Ex | Product |
|---|---|---|---|
| 774 | | 131 | |
| 775 | | 131 | |
| 776 | | 131 | |
| 777 | | 133.1 | |

-continued

| Ex. | Amine (Prep Ex) | Product of Prep. Ex | Product |
|---|---|---|---|
| 778 | (structure) | 131 | (structure) |
| 779 | (structure) | 131 | (structure) |
| 780 | (structure) | 133.2 | (structure) |
| 781 | (structure) | 133 | (structure) |

| Ex. | Amine (Prep Ex) | Product of Prep. Ex | Product |
|---|---|---|---|
| 782 | 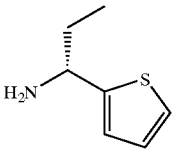 | 131 | 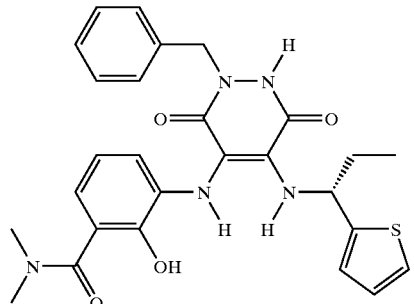 |
| 783 | 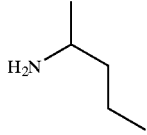 | 131 | 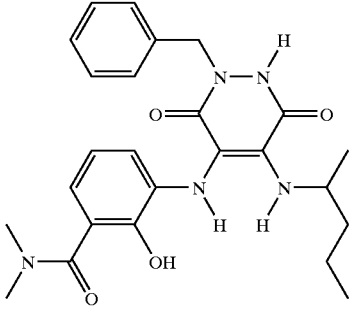 |
| 784 | 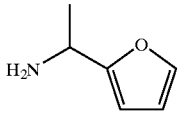 | 131 | 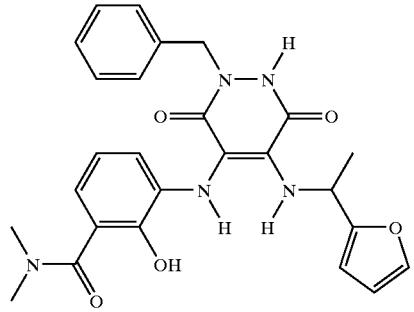 |
| 785 | 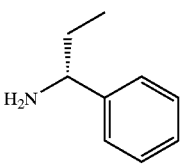 | 132 | 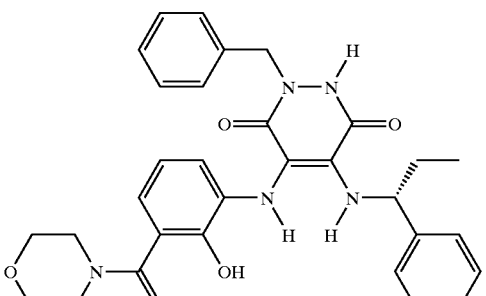 |

-continued

| Ex. | Amine (Prep Ex) | Product of Prep. Ex | Product |
|---|---|---|---|
| 786 | aniline | 131 | (structure) |
| 787 | cyclohexylamine | 131 | (structure) |
| 788 | cyclopentylamine | 131 | (structure) |
| 789 | (S)-2,2,2-trifluoro-1-(thiophen-2-yl)ethanamine | 131 | (structure) |

-continued

| Ex. | Amine (Prep Ex) | Product of Prep. Ex | Product |
|---|---|---|---|
| 790 | | 131 | |
| 791 | | 121 | |
| 792 | | 121 | |
| 793 | | 121 | |

-continued

| Ex. | Amine (Prep Ex) | Product of Prep. Ex | Product |
|---|---|---|---|
| 794 | (structure) | 121 | (structure) |
| 795 | (structure) | 121 | (structure) |
| 796 | (structure) | 121 | (structure) |
| 797 | (structure) | 124 | (structure) |

-continued

| Ex. | Amine (Prep Ex) | Product of Prep. Ex | Product |
|---|---|---|---|
| 798 | | 121 | |
| 799 | | 121 | |
| 800 | | 125 | |
| 801 | | 123 | |

-continued

| Ex. | Amine (Prep Ex) | Product of Prep. Ex | Product |
|---|---|---|---|
| 802 | (S)-1-(thiophen-2-yl)propan-1-amine | 121 | |
| 803 | pentan-2-amine | 121 | |
| 804 | 1-(furan-2-yl)ethan-1-amine | 121 | |
| 805 | (S)-1-phenylpropan-1-amine | 122 | |

-continued

| Ex. | Amine (Prep Ex) | Product of Prep. Ex | Product |
|---|---|---|---|
| 806 | aniline | 121 | |
| 807 | cyclohexylamine | 121 | |
| 808 | cyclopentylamine | 121 | |
| 809 | (S)-2,2,2-trifluoro-1-(thiophen-2-yl)ethylamine | 121 | |

-continued
| Ex. | Amine (Prep Ex) | Product of Prep. Ex | Product |
|---|---|---|---|
| 810 | 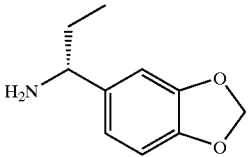 | 121 | 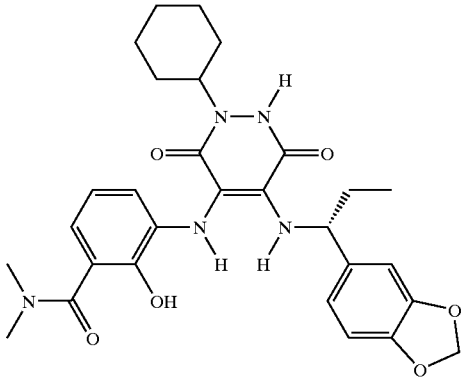 |
| 811 | 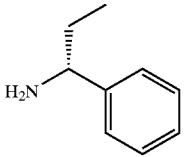 | 45 | 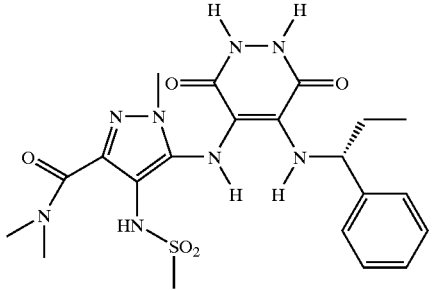 |
| 812 | 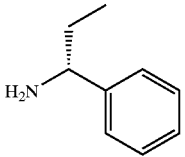 | 46 | 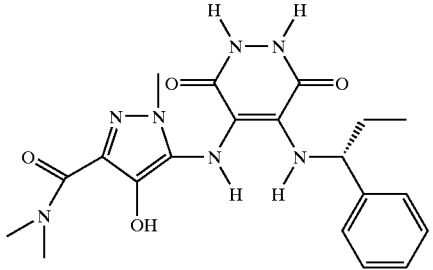 |
| 813 | 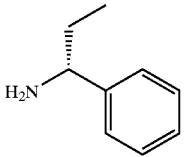 | 47 | 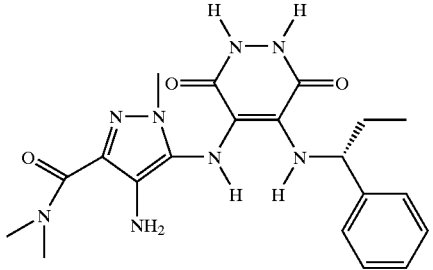 |

-continued

| Ex. | Amine (Prep Ex) | Product of Prep. Ex | Product |
|---|---|---|---|
| 814 | (S)-1-phenylpropylamine | 68 | [structure] |
| 815 | (S)-1-phenylpropylamine | 69 | [structure] |
| 816 | (S)-1-phenylpropylamine | 70 | [structure] |
| 817 | (S)-1-phenylpropylamine | 91 | [structure] |
| 818 | (S)-1-phenylpropylamine | 92 | [structure] |

-continued
| Ex. | Amine (Prep Ex) | Product of Prep. Ex | Product |
|---|---|---|---|
| 819 | 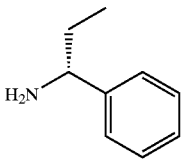 | 93 | 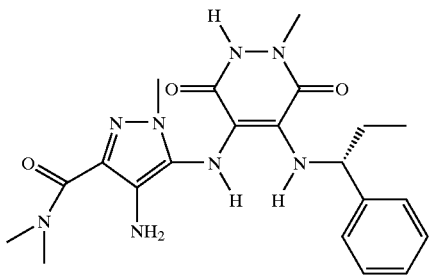 |
| 820 | 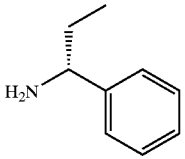 | 113 | 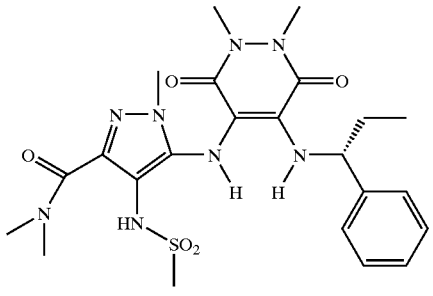 |
| 821 | 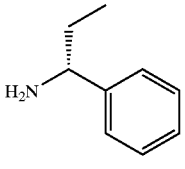 | 114 | 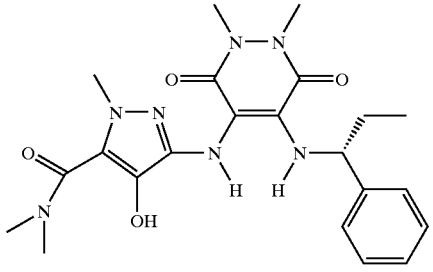 |
| 822 | 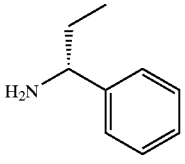 | 115 | 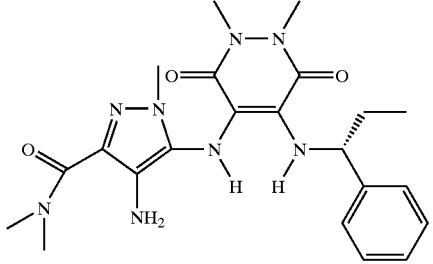 |
| 823 | 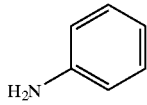 | 71 | 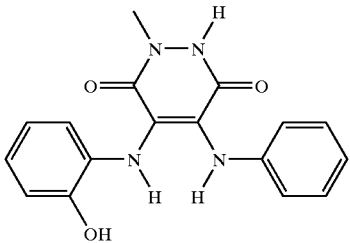 |

-continued

| Ex. | Amine (Prep Ex) | Product of Prep. Ex | Product |
|---|---|---|---|
| 824 | | 71 | |
| 825 | | 71 | |
| 826 | | 71 | |
| 827 | | 71 | |
| 828 | | 71 | |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from the group consisting of:

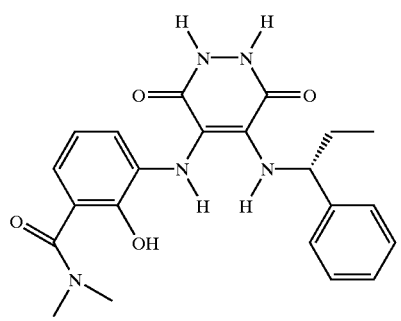

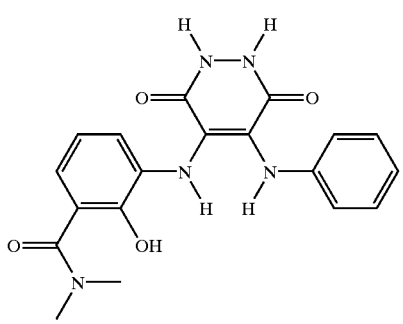

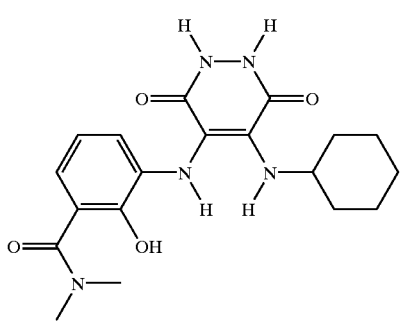

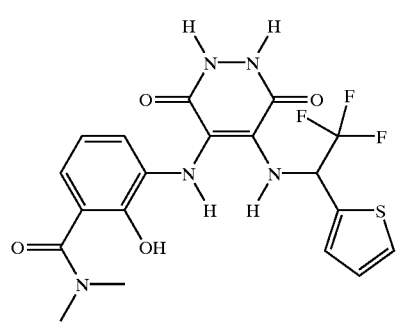

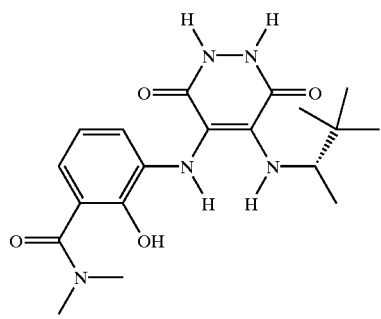

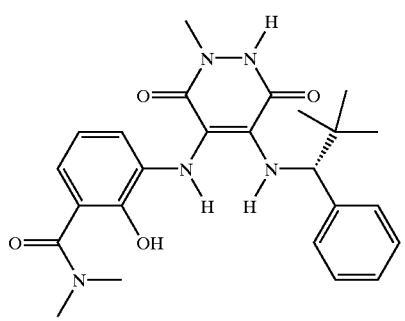

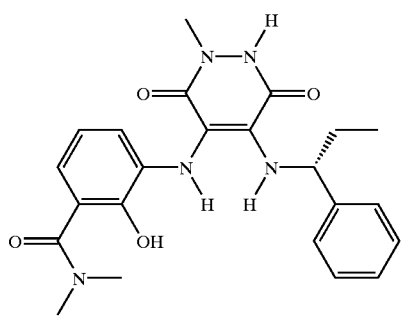

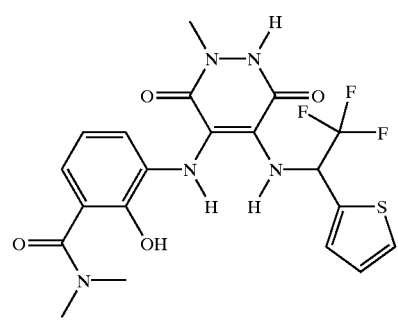

305
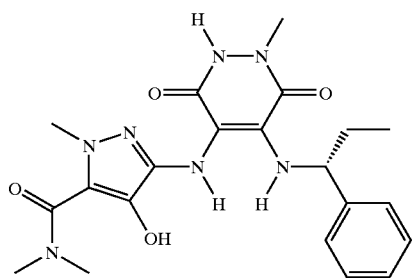
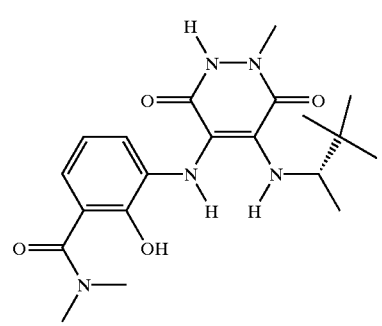
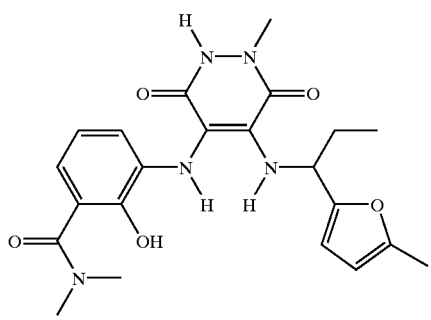
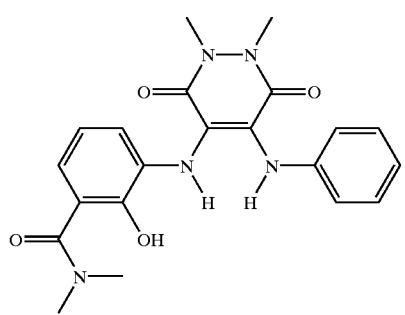
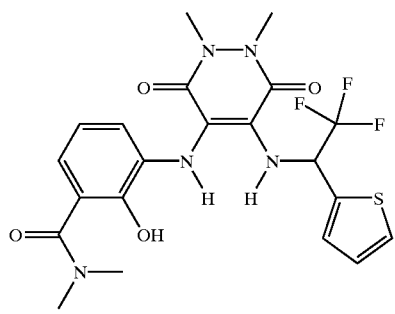
306
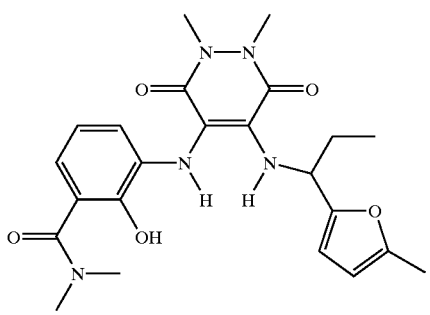
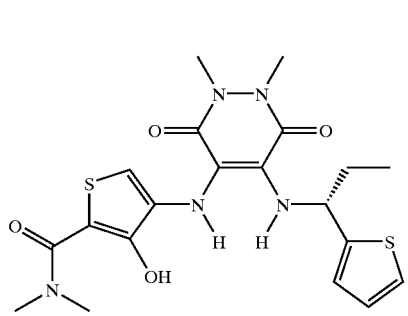
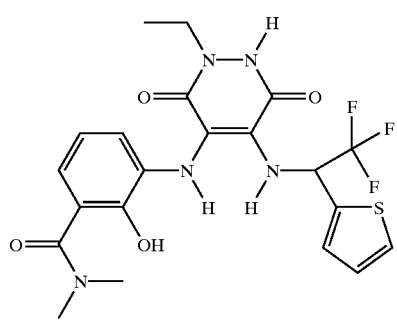
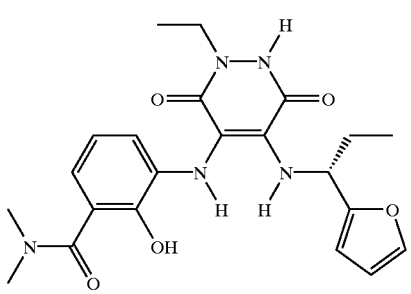
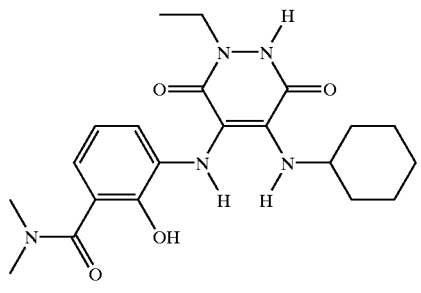

307
-continued
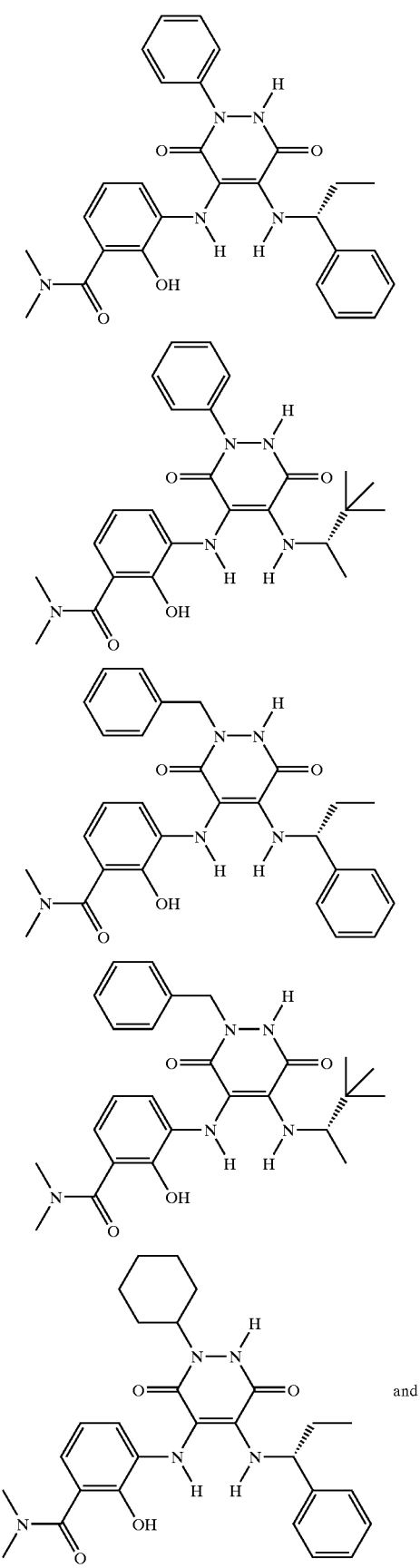
308
-continued
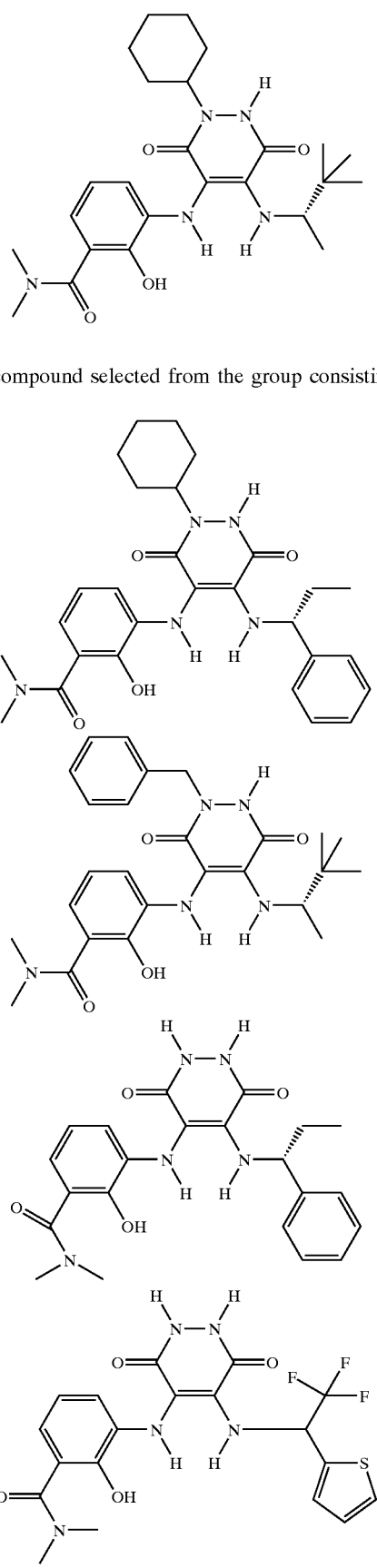
2. A compound selected from the group consisting of:
and 309
-continued
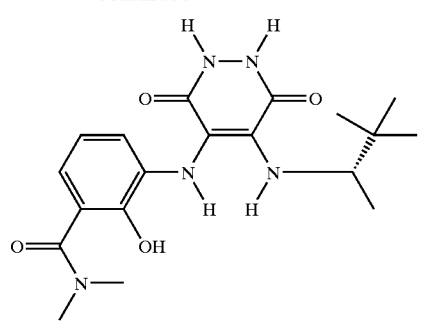
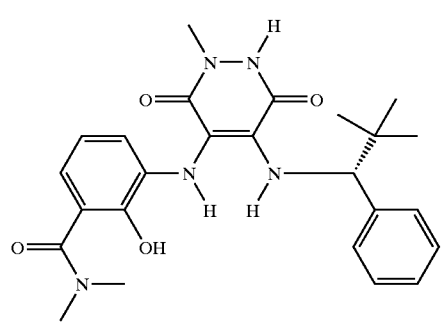
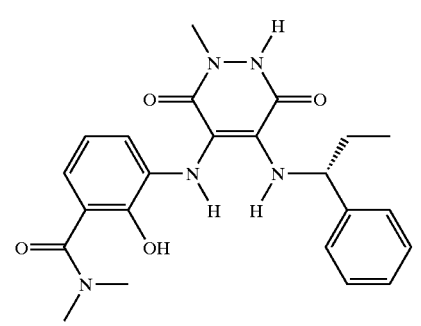
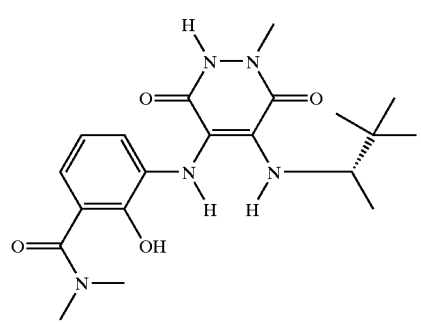
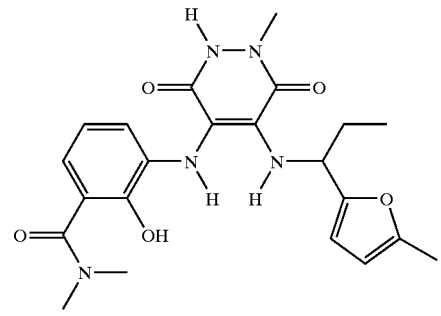
310
-continued
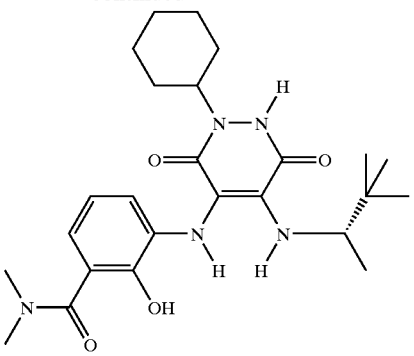
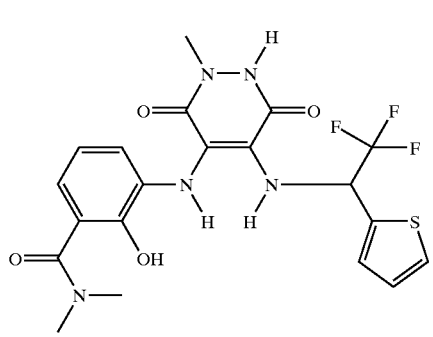
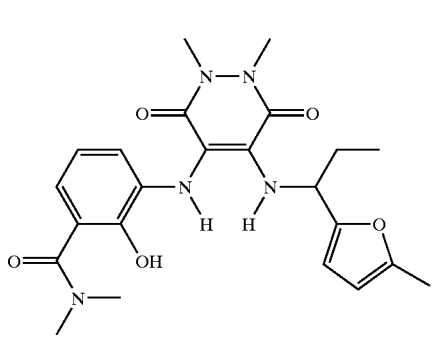
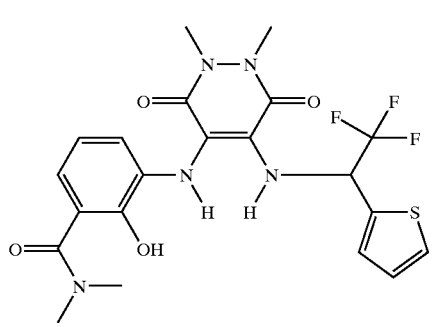
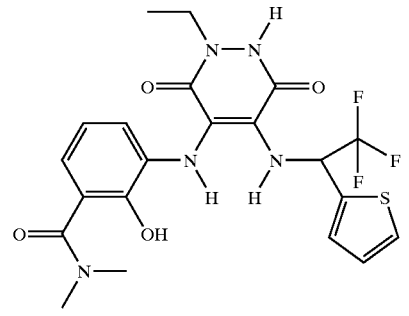

311
-continued
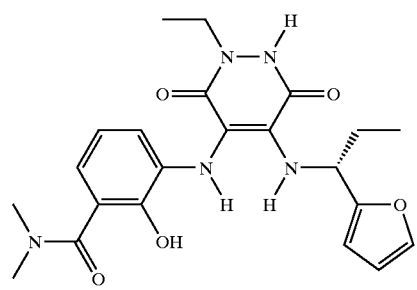
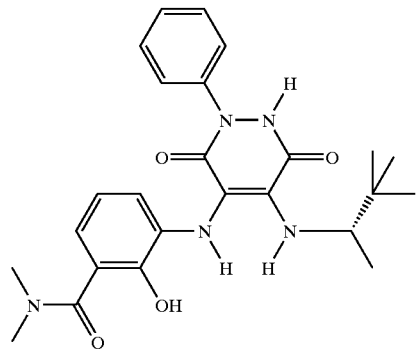
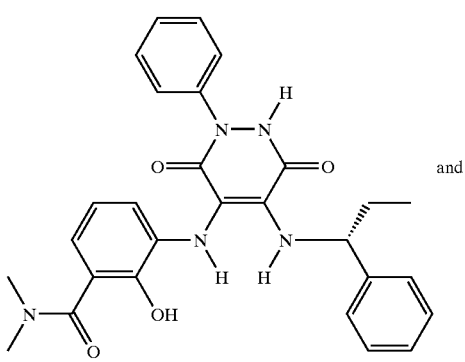
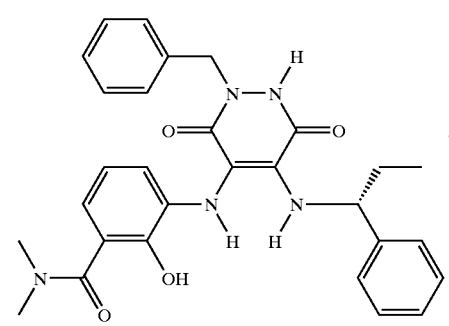
3. A compound selected from the group consisting of:
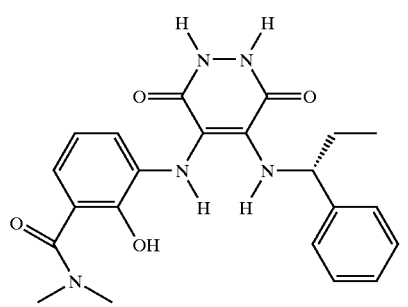
312
-continued
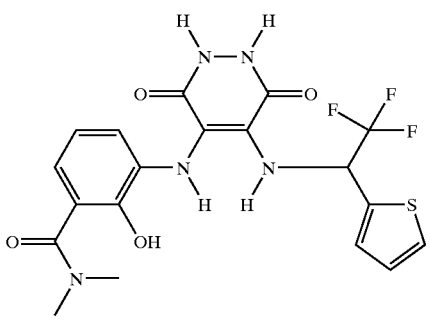
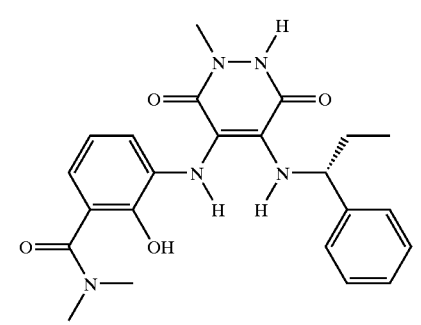
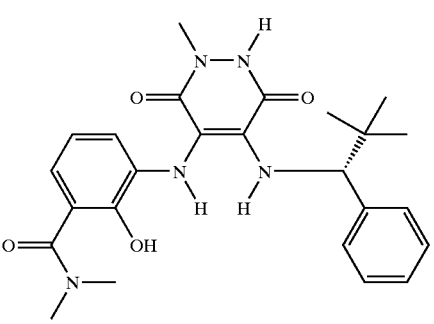
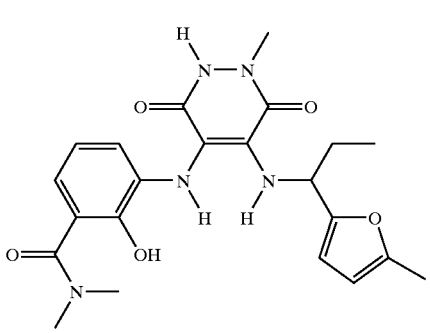
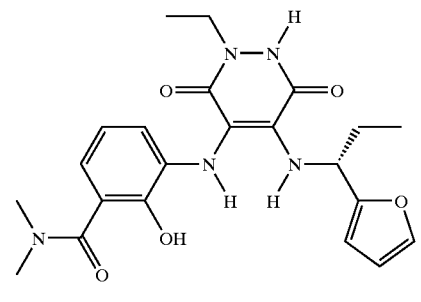
and

313
-continued
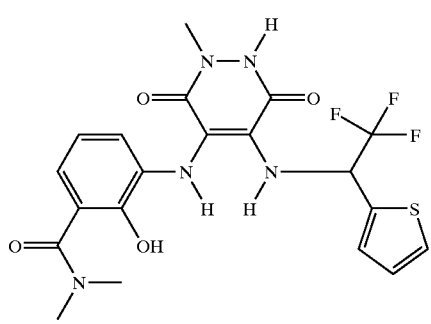
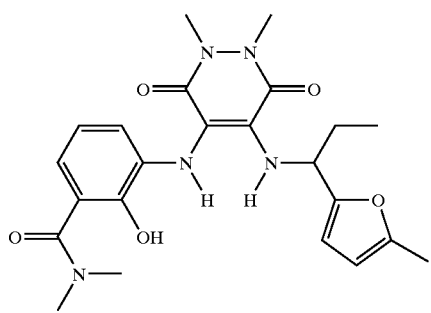
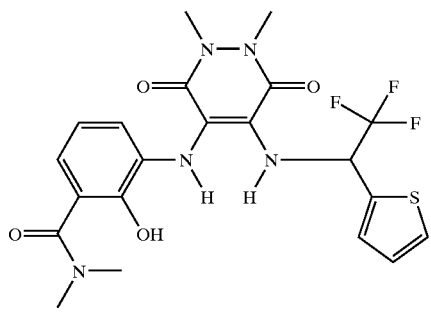
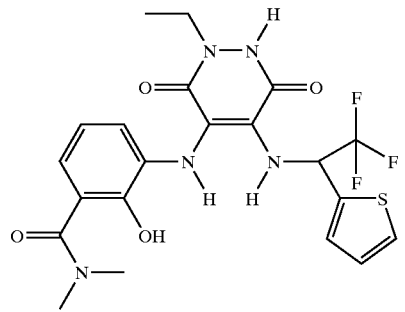
314
-continued
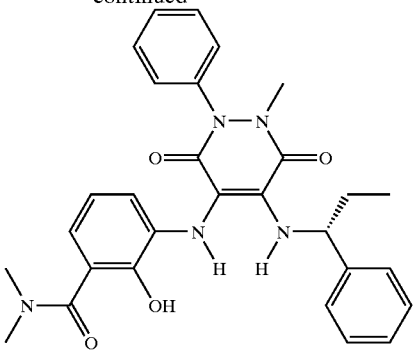
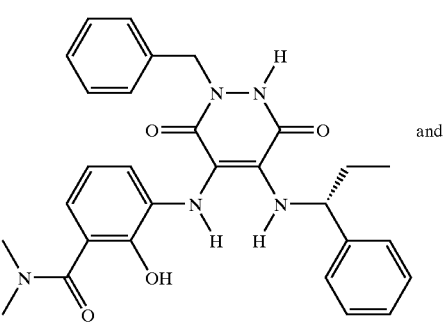
and
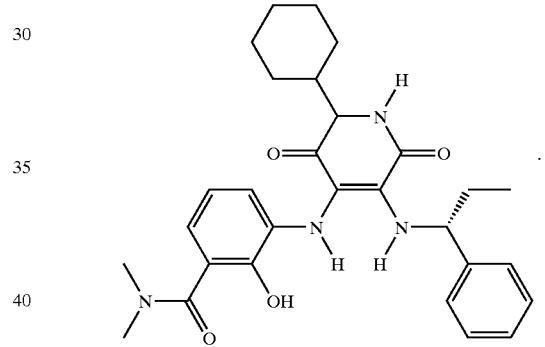
4. A pharmaceutical composition comprising a compound of claim 1 and a pharmaceutically acceptable carrier therefor.
* * * * *